United States Patent
Canich et al.

(10) Patent No.: US 10,550,209 B2
(45) Date of Patent: Feb. 4, 2020

(54) CATALYSTS FOR PRODUCING POLYMERS AND ENHANCED PROPERTIES

(71) Applicant: ExxonMobil Chemical Patents Inc., Baytown, TX (US)

(72) Inventors: Jo Ann M. Canich, Houston, TX (US); Ian C. Stewart, Houston, TX (US); Ilya S. Borisov, Moscow (RU); Bogdan A. Guzeev, Moscow (RU); Dmitry V. Uborsky, Moscow (RU); Alexander Z. Voskoboynikov, Moscow (RU)

(73) Assignee: ExxonMobil Chemical Patents Inc., Baytown, TX (US)

(*) Notice: Subject to any disclaimer, the term of this patent is extended or adjusted under 35 U.S.C. 154(b) by 0 days.

(21) Appl. No.: 15/962,891

(22) Filed: Apr. 25, 2018

(65) Prior Publication Data
US 2018/0244816 A1 Aug. 30, 2018

Related U.S. Application Data

(62) Division of application No. 15/334,144, filed on Oct. 25, 2016, now Pat. No. 9,988,471.

(60) Provisional application No. 62/268,160, filed on Dec. 16, 2015.

(51) Int. Cl.
*C08F 110/06* (2006.01)
*C08F 4/6592* (2006.01)
*C07F 17/00* (2006.01)

(52) U.S. Cl.
CPC .......... *C08F 110/06* (2013.01); *C07F 17/00* (2013.01); *C08F 4/65927* (2013.01)

(58) Field of Classification Search
CPC ...... C08F 10/06; C08F 11/06; C08F 4/65927; C08F 110/06
See application file for complete search history.

(56) References Cited

U.S. PATENT DOCUMENTS

| | | | |
|---|---|---|---|
| 5,459,117 A | 10/1995 | Ewen | |
| 5,627,247 A | 5/1997 | Alt | |
| 5,668,230 A | 9/1997 | Schertl et al. | |
| 6,175,409 B1 | 1/2001 | Nielsen et al. | |
| 6,260,407 B1 | 7/2001 | Petro et al. | |
| 6,294,388 B1 | 9/2001 | Petro | |
| 6,406,632 B1 | 6/2002 | Safir et al. | |
| 6,436,292 B1 | 8/2002 | Petro | |
| 6,454,947 B1 | 9/2002 | Safir et al. | |
| 6,461,515 B1 | 10/2002 | Safir et al. | |
| 6,475,391 B2 | 11/2002 | Safir et al. | |
| 6,491,816 B2 | 12/2002 | Petro | |
| 6,491,823 B1 | 12/2002 | Safir et al. | |
| 8,188,189 B2 | 5/2012 | Sogoh et al. | |
| 2005/0148460 A1 | 7/2005 | Marin et al. | |

FOREIGN PATENT DOCUMENTS

| | | |
|---|---|---|
| EP | 0 672 675 | 7/2002 |
| WO | 99/20664 | 4/1999 |
| WO | 2011/034715 | 3/2011 |
| WO | 2012/134715 | 10/2012 |

OTHER PUBLICATIONS

Coates et al. "Synthesis of Allyl-Terminated Syndiotactic Polypropylene: Macromonomers for the Synthesis of Breanched Polyolefins", Macromolecules, 2005, 38,6259-6268. (Year: 2005).*
Alt, H. et al., "Syndiospezifische Polymerisation von Propylen: 3-, 4-, 3,4-und 4,5-Substituierte Zirkonocenkomplexe des Typs (C13H8-nRnCR'2C5H4)ZrCl2 (n =1,2;R = Alkyl, Aryl; R' = Me,Ph)," Journal of Organometallic Chemistry, 1996, vol. 514, Issues 1-2, pp. 257-270.
Bazinet, P. et al., "Octa- and Nonamethylfluorenyl Complexes of Zr(II), Zr(IV), and Hf(IV) Investigation of Steric and Electronic Effects," Organometallics, 2008, vol. 27, pp. 1267-1274.
Bazinet, P. et al., "Octa and Nonamethylfluorenyl Complexes of Zirconium(IV): Reactive Hydride Derivatives and Reversible Hydrogen Migration between the Metal and the Fluorenyl Ligand," Organometallics, 2009, vol. 28, pp. 2285-2293.
Coskun, N. et al. "An Efficient Catalytic Method for Fulvene Synthesis," Tetrahedron, 2011, vol. 67, pp. 8607-8614.
Demark, S. et al. "Chiral Fluoro Ketones for Catalytic Asymmetric Epoxidation of Alkenes with Oxone," Journal of Organic Chemistry, 2002, vol. 67, p. 3479.
Ewen, J. et al. "Metallocene/Polypropylene Structural Relationships Implications on Polymerization and Stereochemical Control Mechanism," Makromolekulare Chemical, Macromolecular Symposia, 1991, vol. 48-49, pp. 253-295.
Leszczynska, K. et al., "New Route to Alkylaluminum Hydroxides via Hydrolysis of Cyclopentadienylaluminum Complexes," Journal of Organometallic Chemistry, 2007, vol. 692, p. 3907.
Newman, M., et al. "The Synthesis of 6,6'-Diethynyldiphenic Anhydride," Journal of Organic Chemistry, 1971, vol. 36, p. 1398.
Schertl, P., et al. "Synthesis and Polymerisationseigenschaften Substituierter ansaBis(fluorenyliden)komplexe des Zirconiums," Journal of Organometallic Chemistry,1999, vol. 582, pp. 328-337.
Schmid, M., et al. "Unbridged Cyclopentadienyl-Fluorenyl Complexes of Zirconium as Catalysts for Homogeneous Olefin Polymerization," Journal of Organometallic Chemistry, 1995, vol. 501, pp. 101-106.
Siedle, A.R. et al. "A Measure of Metallocene Catalyst Shape Asymmetry," Journal of Molecular Catalysis A: Chemical, 2003, vol. 191, pp. 167-175.

(Continued)

*Primary Examiner* — Caixia Lu
(74) *Attorney, Agent, or Firm* — Catherine L. Bell

(57) ABSTRACT

Disclosed are novel hafnium-based metallocene catalyst compounds with the following characteristics: 1) 4,5-dialkyl substitutions on a fluorenyl ligand, and optionally additional substitutions, 2) a cyclopentadienyl ligand, optionally with substitutions, and 3) a bridging group from group 14 of the Periodic Table. Also disclosed are catalyst systems comprising such catalyst compounds and their uses thereof, and polymers produced using such catalyst systems.

36 Claims, 5 Drawing Sheets

(56) References Cited

OTHER PUBLICATIONS

Siedle, A.R., et al. "Synthesis of Unsymmetrical ansa-fluorenyl metallocenes," Journal of Molecular Catalysis A: Chemical, 2004, vol. 214, pp. 187-198.
Tang, H., et al. "Reactions of Diorganocadmium Compounds with Other Dialkylmetal Compounds and Macrocycles: Synthesis of Organocadmate Anions," Organometallics, 2001, vol. 20, p. 1569.
Tebikie, W., et al. "In Silico Design of C1- and Cs-Symmetric Fluorenyl-Based Metallocene Catalysts for the Synthesis of High Molecular-Weight Polymers from Ethylene/Propylene Copolymerization," Organometallics, 2009, vol. 28, pp. 1383-1390.
Yamamoto, G., et al. "Deamination of 1-Alkyl-9-aminomethyltriptycenes. Participation of a Neighboring 1-Alkyl Substituent," Bulletin of the Chemical Society of Japan, 2006, vol. 79, pp. 1585.

\* cited by examiner

CATALYSTS FOR PRODUCING POLYMERS AND ENHANCED PROPERTIES

CROSS REFERENCE TO RELATED APPLICATIONS

This invention is a divisional of U.S. Ser. No. 15/334,144, filed Oct. 25, 2016, which claims priority to and the benefit of U.S. Ser. No. 62/268,160, filed Dec. 16, 2015.

FIELD OF THE INVENTION

This invention relates to novel hafnium/catalyst compounds comprising 4,5-dialkyl substituted fluorenyl ligands, catalyst systems comprising such and uses thereof, and polymers produced using such catalyst systems.

BACKGROUND OF THE INVENTION

Polyolefins are of great interest in industry as they have many uses in different areas. Polyolefins, such as polyethylene and polypropylene, are used in everything from waxes and plasticizers to films and structural components. Of late, many have been interested in modifying the architecture of such polyolefins in the hopes of obtaining new and better properties.

Vinyl terminated polymers, including homopolymers of polypropylene and copolymers of ethylene and polypropylene, are known to be useful for post-polymerization reactions due to the available ethylenic unsaturation in one polymer, at one chain end or both. Such reactions include addition reactions, such as those used in grafting other ethylenically unsaturated moieties, and further insertion polymerization where the vinyl terminated polymers are copolymerized with other monomers such as α-olefins and/or other insertion polymerizable monomers.

Vinyl chain ends are generally accepted to be more reactive to chain-end functionalization and insertion in subsequent polymerization reactions than are the other types. Such polymers with a high percentage of vinyl terminal bonds would be desirable for use in the preparation of branched polymers. Accordingly, a need exists for catalysts capable of forming polymers with a high percentage of vinyl terminal bonds.

Alt, Helmut G., et al., *Journal of Organometallic Chemistry*, vol. 514, issues 1-2, pp. 257-270 (1996), uses certain 3-, 4-, 3-, 4-, and 4,5-substituted zirconocene complexes of the type $(C_{13}H_{8-n}R_nCR'_2C_5H_4)ZrCl_2$, where n is 1 or 2, R is an alkyl or aryl, and R' is Me or Ph for polypropylene polymerizations. At a polymerization temperature of 62° C., the article reports an activity of 9.3 kg/mmol of catalyst per hour, an Mn of 29,000, and a Tm of 107.9° C. There is no indication, however, that these catalysts produce polymers with vinyl chain ends.

Siedle, A. R., et al., *Journal of Molecular Catalysis A: Chemical*, vol. 191, issue 2, pp. 167-175 (2003) discusses an asymmetry parameter applied to ansa-bridged metallocene catalysts of the type [(ligand 1)-bridge-(ligand 2)MX$_2$ where ligands 1 and 2 are variously substituted cyclopentadienyl, indenyl, or fluorenyl groups connected by, e.g., SiMe$_2$ or C$_2$H$_4$ and where M is Ti, Zr, or Hf, and X is a halogen or alkyl group. The asymmetry parameter is defined as the ratio of the van der Waals area of ligand fragment 1 to that of ligand fragment 2. A series of syndioregulating catalysts were used to polymerize propylene. As the catalyst asymmetry parameter increases, the polypropylenes produced are said to have successively higher syndiotacticity. WO 99/20664 claims a metallocene catalyst of the type [(ligand 1)-bridge-(ligand 2)MX$_2$, where ligand 1 and ligand 2 are different and may include substituted and unsubstituted cyclopentadienyl, indenyl, and fluorenyl groups, the catalyst having an asymmetry parameter of 1.03 to 1.69. WO 99/20664 discloses a catalyst, {flu-CMe$_2$-Cp}ZrCl$_2$, having an asymmetry parameter of 2.09.

Other references of interest include: WO 2012/134715 and US 2005/148460.

The presence of long chain branching may lead to improved processability and some improved end-use properties in certain polymers. For instance, long chain branching may result in polymers exhibiting improved melt elasticity and/or improved shear thinning. Polymers produced using conventional Ziegler-Natta catalysts may have long chain branching, but such conventional processes are often more expensive than newer technologies using metallocene catalysts. Metallocene based polymers, however, typically lack long chain branching.

There is still a need for new and improved metallocene catalyst systems for the polymerization of olefins, in order to achieve specific polymer properties, such as polymers with a high percentage of vinyl terminal bonds and higher molecular weights, and polymers with long chain branching. The present invention provides novel catalyst compounds capable of meeting these needs, catalysts systems comprising such compounds, and processes for the polymerization of olefins using such compounds and systems.

SUMMARY OF THE INVENTION

This invention relates to novel hafnium-based metallocene catalyst compounds with the following characteristics: 1) 4,5-dialkyl substitutions on a fluorenyl ligand, and optionally additional substitutions, 2) a cyclopentadienyl ligand, optionally with substitutions, and 3) a bridging group from group 14 of the Periodic Table. The catalyst compounds may be represented by formula (I):

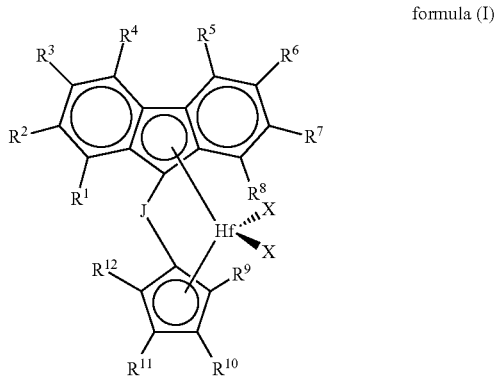

formula (I)

wherein each $R^1$, $R^2$, $R^3$, $R^6$, $R^7$, $R^8$, $R^9$, $R^{10}$, $R^{11}$ and $R^{12}$ is independently hydrogen or a $C_1$ to $C_{10}$ alkyl, and wherein any of $R^1$ and $R^2$, $R^2$ and $R^3$, $R^6$ and $R^7$, and $R^7$ and $R^8$ are optionally bonded together to form a ring structure;

each $R^4$ and $R^5$ is independently a $C_1$ to $C_{10}$ alkyl;

J is $SiR^{13}R^{14}$, $GeR^{13}R^{14}$ or $(CR^{15}R^{16})_x$, where x is 1 or 2; $R^{13}$ and $R^{14}$ are each independently selected from the group consisting of substituted or unsubstituted hydrocarbyl, halocarbyl, and silylcarbyl; $R^{15}$ and $R^{16}$ are each independently selected from the group consisting of hydrogen, substituted or unsubstituted hydrocarbyl, halocarbyl, and silylcarbyl;

and $R^{13}$ and $R^{14}$, or $R^{15}$ and $R^{16}$, when $R^{15}$ and $R^{16}$ are not hydrogen, are optionally bonded together to form a ring structure; and each X is independently a univalent anionic ligand, or two Xs are joined and bound to the metal atom to form a metallocycle ring, or two Xs are joined to form a chelating ligand, a diene ligand, or an alkylidene ligand.

The catalyst compounds may also be represented by formula (II):

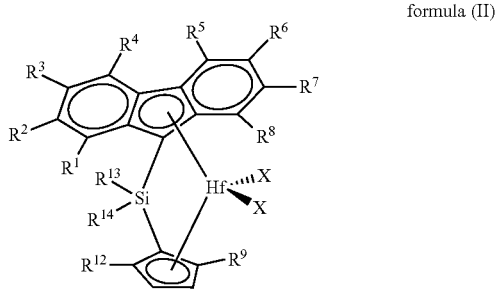

formula (II)

wherein each $R^1$, $R^2$, $R^3$, $R^6$, $R^7$, $R^8$, $R^9$, and $R^{12}$ is independently hydrogen or a $C_1$ to $C_{10}$ alkyl, and wherein any of $R^1$ and $R^2$, $R^2$ and $R^3$, $R^6$ and $R^7$, and $R^7$ and $R^8$ are optionally bonded together to form a ring structure;

each $R^4$ and $R^5$ is independently a $C_1$ to $C_{10}$ alkyl;

each $R^{13}$ and $R^{14}$ is independently selected from the group consisting of substituted or unsubstituted hydrocarbyl, halocarbyl, and silylcarbyl; and each X is independently a univalent anionic ligand, or two Xs are joined and bound to the metal atom to form a metallocycle ring, or two Xs are joined to form a chelating ligand, a diene ligand, or an alkylidene ligand.

The catalyst compounds may also be represented by formula (III):

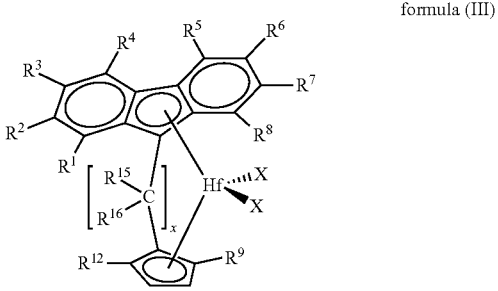

formula (III)

wherein each $R^1$, $R^2$, $R^3$, $R^6$, $R^7$, $R^8$, $R^9$, and $R^{12}$ is independently hydrogen or a $C_1$ to $C_{10}$ alkyl, and wherein any of $R^1$ and $R^2$, $R^2$ and $R^3$, $R^6$ and $R^7$, and $R^7$ and $R^8$ are optionally bonded together to form a ring structure;

each $R^4$ and $R^5$ is independently a $C_1$ to $C_{10}$ alkyl;

x is 1 or 2;

each $R^{15}$ and $R^{16}$ is independently selected from the group consisting of hydrogen, substituted or unsubstituted hydrocarbyl, halocarbyl and silylcarbyl; and $R^{15}$ and $R^{16}$, when $R^{15}$ and $R^{16}$ are not hydrogen, are optionally bonded together to form a ring structure; and each X is independently a univalent anionic ligand, or two Xs are joined and bound to the metal atom to form a metallocycle ring, or two Xs are joined to form a chelating ligand, a diene ligand, or an alkylidene ligand.

This invention also relates to catalyst systems comprising one or more catalyst compounds of formula (I), (II), or (III) in combination with an activator. The catalyst systems may be used to polymerize olefins in a process comprising contacting one or more olefins with a catalyst system comprising one or more catalyst compounds of formula (I), (II), or (III) and an activator.

The invention also relates to a method for making a vinyl terminated syndiotactic polypropylene polymer having at least 50% allyl chain ends and/or 3-alkyl chain ends relative to the total number of unsaturated chain ends, wherein the process comprises contacting propylene with a catalyst system, the catalyst system comprising an activator and at least one metallocene compound represented by formula (IV):

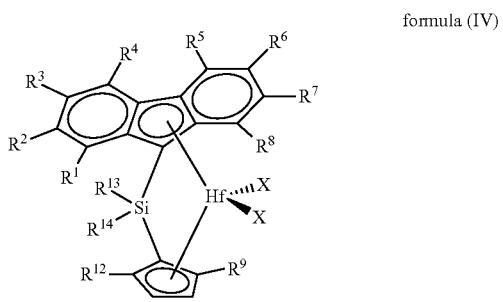

formula (IV)

wherein each $R^1$, $R^2$, $R^3$, $R^6$, $R^7$, $R^8$, $R^9$, and $R^{12}$ is independently hydrogen or a $C_1$ to $C_{10}$ alkyl, and wherein any of $R^1$ and $R^2$, $R^2$ and $R^3$, $R^6$ and $R^7$, and $R^7$ and $R^8$ are optionally bonded together to form a ring structure;

each $R^4$ and $R^5$ is independently a $C_1$ to $C_{10}$ alkyl;

each $R^{13}$ and $R^{14}$ is independently selected from the group consisting of substituted or unsubstituted hydrocarbyl, halocarbyl, and silylcarbyl; and each X is independently a univalent anionic ligand, or two Xs are joined and bound to the metal atom to form a metallocycle ring, or two Xs are joined to form a chelating ligand, a diene ligand, or an alkylidene ligand.

The invention also relates to a syndiotactic propylene homopolymer having: 1) at least 50% allyl chain ends and/or 3-alkyl chain ends relative to the total number of unsaturated chain ends; 2) an Mw of 4000 g/mol or more; and 3) no detectable melting temperature by DSC.

The catalyst compounds disclosed herein are particularly useful for making vinyl terminated polymers with high Mw, such as but not limited to polypropylene homopolymers, ethylene and propylene copolymers, and ethylene propylene diene copolymers or terpolymers (EPDM). The vinyl unsaturation of the polymers made using the catalysts and methods herein may be further enhanced by controlling process conditions, such as through the use of higher reactor temperatures or type of activator.

DETAILED DESCRIPTION OF THE INVENTION

Figure 1:
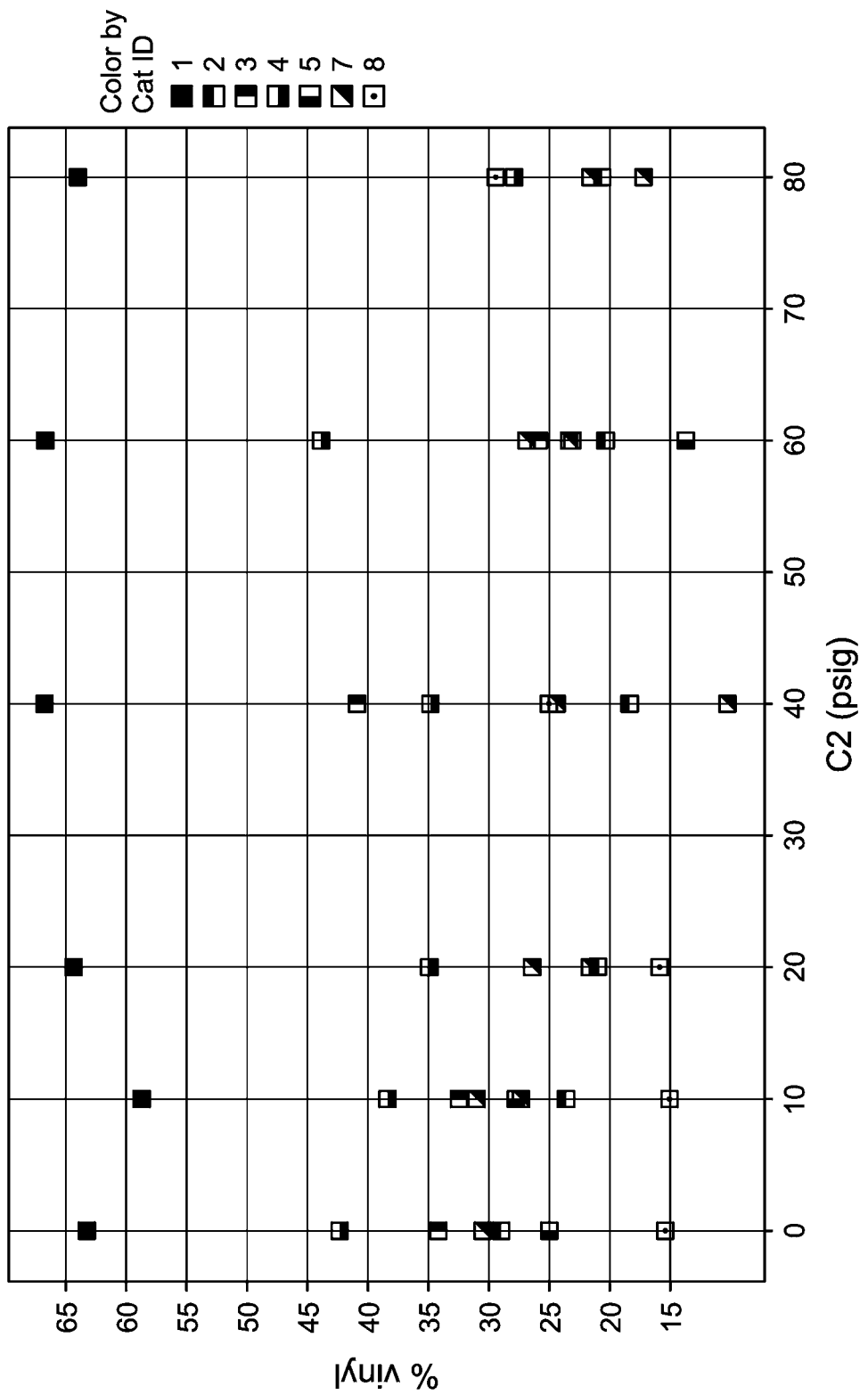
FIG. 1 is a graph of vinyl unsaturation versus reactor ethylene pressure for polymers produced at 70° C. by inventive and comparative catalysts.

For the purposes of this invention and the claims thereto, the new numbering scheme for the Periodic Table Groups is used as described in Chemical and Engineering News, 63(5), pg. 27 (1985). Therefore, a "group 4 metal" is an element from group 4 of the Periodic Table, e.g., Hf, Ti, or Zr.

The following abbreviations may be used herein: Me is methyl, Et is ethyl, Pr is propyl, cPr is cyclopropyl, nPr is n-propyl, iPr is isopropyl, Bu is butyl, nBu is normal butyl, iBu is isobutyl, sBu is sec-butyl, tBu is tert-butyl, Oct is octyl, Ph is phenyl, Bn is benzyl, and MAO is methylalumoxane.

For purposes of this disclosure, "hydrocarbyl radical" is defined to be a $C_1$-$C_{100}$ radical, that may be linear, branched, or cyclic, and when cyclic, aromatic or non-aromatic. Substituted hydrocarbyl radicals are radicals in which at least one hydrogen atom has been substituted with at least one functional group such as $NR^*_2$, $OR^*$, $SeR^*$, $TeR^*$, $PR^*_2$, $AsR^*_2$, $SbR^*_2$, $SR^*$, $BR^*_2$, $SiR^*_3$, $GeR^*_3$, $SnR^*_3$, $PbR^*_3$ and the like or where at least one non-hydrocarbon atom or group has been inserted within the hydrocarbyl radical, such as —O—, —S—, —Se—, —Te—, —N($R^*$)—, =N—, —P($R^*$)—, =P—, —As($R^*$)—, =As—, —Sb($R^*$)—, =Sb—, —B($R^*$)—, =B—, —Si($R^*$)$_2$—, —Ge($R^*$)$_2$—, —Sn($R^*$)$_2$—, —Pb($R^*$)$_2$— and the like, where $R^*$ is independently a hydrocarbyl or halocarbyl radical, and two or more $R^*$ may join together to form a substituted or unsubstituted saturated, partially unsaturated or aromatic cyclic or polycyclic ring structure.

Halocarbyl radicals are radicals in which one or more hydrocarbyl hydrogen atoms have been substituted with at least one halogen (e.g., F, Cl, Br, I) or halogen-containing group (e.g., $CF_3$).

Substituted halocarbyl radicals are radicals in which at least one halocarbyl hydrogen or halogen atom has been substituted with at least one functional group such as $NR^*_2$, $OR^*$, $SeR^*$, $TeR^*$, $PR^*_2$, $AsR^*_2$, $SbR^*_2$, $SR^*$, $BR^*_2$, $SiR^*_3$, $GeR^*_3$, $SnR^*_3$, $PbR^*_3$ and the like or where at least one non-carbon atom or group has been inserted within the halocarbyl radical such as —O—, —S—, —Se—, —Te—, —N($R^*$)—, =N—, —P($R^*$)—, =P—, —As($R^*$)—, =As—, —Sb($R^*$)—, =Sb—, —B($R^*$)—, =B—, —Si($R^*$)$_2$—, —Ge($R^*$)$_2$—, —Sn($R^*$)$_2$—, —Pb($R^*$)$_2$— and the like, where $R^*$ is independently a hydrocarbyl or halocarbyl radical provided that at least one halogen atom remains on the original halocarbyl radical. Additionally, two or more $R^*$ may join together to form a substituted or unsubstituted saturated, partially unsaturated or aromatic cyclic or polycyclic ring structure.

Silylcarbyl radicals (also called silylcarbyls) are groups in which the silyl functionality is bonded directly to the indicated atom or atoms. Examples include $SiH_3$, $SiH_2R^*$, $SiHR^*_2$, $SiR^*_3$, $SiH_2(OR^*)$, $SiH(OR^*)_2$, $Si(OR^*)_3$, $SiH_2(NR^*_2)$, $SiH(NR^*_2)_2$, $Si(NR^*_2)_3$, and the like where $R^*$ is independently a hydrocarbyl or halocarbyl radical and two or more $R^*$ may join together to form a substituted or unsubstituted saturated, partially unsaturated or aromatic cyclic or polycyclic ring structure. Preferred silylcarbyls are of formula $SiR^*_3$. Polar radicals or polar groups are groups in which the heteroatom functionality is bonded directly to the indicated atom or atoms. They include heteroatoms of Groups 13-17 of the Periodic Table either alone or connected to other elements by covalent or other interactions such as ionic, van der Waals forces, or hydrogen bonding.

The term "aryl" or "aryl group" means a six carbon aromatic ring and the substituted variants thereof, including but not limited to, phenyl, 2-methyl-phenyl, xylyl, and 4-bromo-xylyl. Likewise, "heteroaryl" means an aryl group where a ring carbon atom (or two or three ring carbon atoms) has been replaced with a heteroatom, preferably N, O, or S. As used herein, the term "aromatic" also refers to pseudoaromatic heterocycles, which are heterocyclic substituents that have similar properties and structures (nearly planar) to aromatic heterocyclic ligands, but are not by definition aromatic; likewise, the term "aromatic" also refers to substituted aromatics.

As used herein, Mn is number average molecular weight, Mw is weight average molecular weight, and Mz is z average molecular weight, wt % is weight percent, and mol % is mole percent. Molecular weight distribution (MWD), also referred to as polydispersity, is defined to be Mw divided by Mn. Unless otherwise noted, all molecular weight units (e.g., Mw, Mn, Mz) are g/mol.

Unless otherwise noted all melting points (Tm) are DSC second melt.

Room temperature is 23° C. unless otherwise noted.

Catalyst Compounds

This invention relates to a novel group of hafnium-based metallocene catalyst compounds with the following characteristics: 1) 4,5-dialkyl substitutions on a fluorenyl ligand, and optionally with additional substitutions, 2) a cyclopentadienyl ligand, optionally with substitutions, and 3) a bridging group from group 14 of the Periodic Table.

These catalyst compounds are particularly useful for making vinyl terminated polymers with high Mw, such as but not limited to polypropylene homopolymers, ethylene and propylene copolymers, and ethylene propylene diene copolymers or terpolymers (EPDM), including EPDM with long chain branching. For example, catalyst compounds of the invention can produce amorphous polypropylene with a high percentage of vinyl unsaturation. The vinyl unsaturation of the polymers made using the catalysts and methods herein may be further enhanced by controlling process conditions, such as through the use of higher reactor temperatures or type of activator.

The catalyst compounds disclosed herein enable the ability to incorporate in situ long chain branching into the polymers formed. For example, the catalyst compounds may enable long chain branches to be incorporated into linear low density polyethylene (LLDPE), polypropylene, EPDM, or other polymers through incorporation of in situ generated vinyl terminated macromonomer into growing polymer chains. Long chain branches, even at very low concentrations, have a strong impact on polymer melt behavior and thus can favorably affect polymer processing properties.

This hafnium-based metallocene catalyst compounds of the invention have the following characteristics: 1) 4,5-dialkyl substitutions on a fluorenyl ligand, and optionally additional substitutions, 2) a cyclopentadienyl ligand, optionally with substitutions, and 3) a bridging group from group 14 of the Periodic Table. The catalyst compounds may be represented by formula (I):

formula (I)

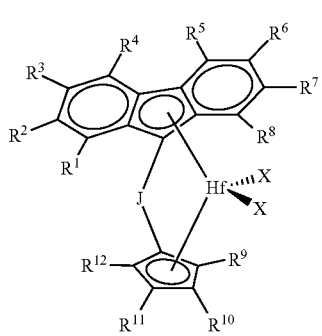

wherein each $R^1$, $R^2$, $R^3$, $R^6$, $R^7$, $R^8$, $R^9$, $R^{10}$, $R^{11}$, and $R^{12}$ is independently hydrogen or a $C_1$ to $C_{10}$ alkyl, and wherein any of $R^1$ and $R^2$, $R^2$ and $R^3$, $R^6$ and $R^7$, and $R^7$ and $R^8$ are optionally bonded together to form a ring structure;

each $R^4$ and $R^5$ is independently a $C_1$ to $C_{10}$ alkyl;

J is $SiR^{13}R^{14}$, $GeR^{13}R^{14}$ or $(CR^{15}R^{16})_x$, where x is 1 or 2; $R^{13}$, $R^{14}$ are each independently selected from the group consisting of substituted or unsubstituted hydrocarbyl, halocarbyl, and silylcarbyl; $R^{15}$ and $R^{16}$ are each independently selected from the group consisting of hydrogen, substituted or unsubstituted hydrocarbyl, halocarbyl and silylcarbyl; and $R^{13}$ and $R^{14}$, or $R^{15}$ and $R^{16}$, when $R^{15}$ and $R^{16}$ are not hydrogen, are optionally bonded together to form a ring structure; and each X is independently a univalent anionic ligand, or two Xs are joined and bound to the metal atom to form a metallocycle ring, or two Xs are joined to form a chelating ligand, a diene ligand, or an alkylidene ligand.

The catalyst compounds may also be represented by formula (II):

formula (II)

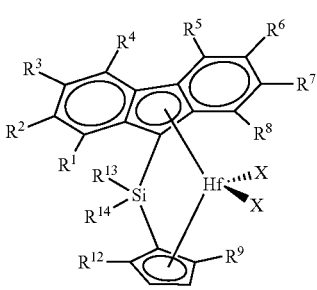

wherein each $R^1$, $R^2$, $R^3$, $R^6$, $R^7$, $R^8$, $R^9$, and $R^{12}$ is independently hydrogen or a $C_1$ to $C_{10}$ alkyl, and wherein any of $R^1$ and $R^2$, $R^2$ and $R^3$, $R^6$ and $R^7$, and $R^7$ and $R^8$ are optionally bonded together to form a ring structure;

each $R^4$ and $R^5$ is independently a $C_1$ to $C_{10}$ alkyl;

each $R^{13}$ and $R^{14}$ is independently selected from the group consisting of substituted or unsubstituted hydrocarbyl, halocarbyl, and silylcarbyl; and each X is independently a univalent anionic ligand, or two Xs are joined and bound to the metal atom to form a metallocycle ring, or two Xs are joined to form a chelating ligand, a diene ligand, or an alkylidene ligand.

The catalyst compounds may also be represented by formula (III):

formula (III)

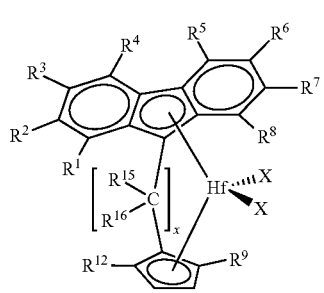

wherein each $R^1$, $R^2$, $R^3$, $R^6$, $R^7$, $R^8$, $R^9$, and $R^{12}$ is independently hydrogen or a $C_1$ to $C_{10}$ alkyl, and wherein any of $R^1$ and $R^2$, $R^2$ and $R^3$, $R^6$ and $R^7$, and $R^7$ and $R^8$ are optionally bonded together to form a ring structure;

each $R^4$ and $R^5$ is independently a $C_1$ to $C_{10}$ alkyl;

x is 1 or 2;

each $R^{15}$ and $R^{16}$ is independently selected from the group consisting of hydrogen, substituted or unsubstituted hydrocarbyl, halocarbyl and silylcarbyl; and $R^{15}$ and $R^{16}$, when $R^{15}$ and $R^{16}$ are not hydrogen, are optionally bonded together to form a ring structure; and each X is independently a univalent anionic ligand, or two Xs are joined and bound to the metal atom to form a metallocycle ring, or two Xs are joined to form a chelating ligand, a diene ligand, or an alkylidene ligand.

This invention also relates to a method for making a vinyl terminated syndiotactic polypropylene polymer having at least 50% allyl chain ends and/or 3-alkyl chain ends relative to the total number of unsaturated chain ends, wherein the process comprises contacting propylene with a catalyst system, the catalyst system comprising an activator and at least one metallocene compound represented by formula (IV):

formula (IV)

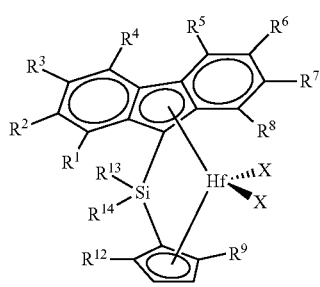

wherein each $R^1$, $R^2$, $R^3$, $R^6$, $R^7$, $R^8$, $R^9$, and $R^{12}$ is independently hydrogen or a $C_1$ to $C_{10}$ alkyl, and wherein any of $R^1$ and $R^2$, $R^2$ and $R^3$, $R^6$ and $R^7$, and $R^7$ and $R^8$ are optionally bonded together to form a ring structure;

each $R^4$ and $R^5$ is independently a $C_1$ to $C_{10}$ alkyl;

each $R^{13}$ and $R^{14}$ is independently selected from the group consisting of substituted or unsubstituted hydrocarbyl, halocarbyl, and silylcarbyl; and each X is independently a univalent anionic ligand, or two Xs are joined and bound to the metal atom to form a metallocycle ring, or two Xs are joined to form a chelating ligand, a diene ligand, or an alkylidene ligand.

The invention also relates to a syndiotactic propylene homopolymer having: 1) at least 50% allyl chain ends and/or 3-alkyl chain ends relative to the total number of unsaturated chain ends; 2) an Mw of 4000 g/mol or more; and 3) no detectable melting temperature by DSC.

In formula (I), $R^4$ and $R^5$ may be independently selected from methyl, ethyl, propyl or butyl or isomers thereof; preferably n-propyl, isopropyl, methyl, or ethyl; even more preferably methyl or ethyl. For example, $R^4$ and $R^5$ may be methyl or $R^4$ and $R^5$ may be ethyl. Alternately, both $R^4$ and $R^5$ are not methyl.

In formula (I), $R^1$, $R^2$, $R^3$, $R^6$, $R^7$, and $R^8$ may be independently selected from hydrogen, or a $C_1$-$C_5$ alkyl, and are preferably hydrogen.

In formula (I), $R^9$, $R^{10}$, and $R^{12}$ may be independently selected from hydrogen or a $C_1$-$C_5$ alkyl; preferably $R^9$ and $R^{12}$ are independently hydrogen or a $C_1$-$C_5$ alkyl and $R^{10}$ and $R^{11}$ are hydrogen; more preferably, $R^9$, $R^{10}$, $R^{11}$, and $R^{12}$ are hydrogen.

In formula (I), J may be $SiR^{13}R^{14}$, with each $R^{13}$ and $R^{14}$ independently selected from substituted or unsubstituted hydrocarbyl, halocarbyl, and silylcarbyl, and $R^{13}$ and $R^{14}$ are optionally bonded together to form a ring structure. For example, $R^{13}$ and $R^{14}$ may be independently selected from methyl, ethyl, propyl, butyl, pentyl, hexyl, heptyl, octyl, nonyl, decyl, phenyl, tolyl, benzyl, and isomers thereof. J may also be selected from dimethylsilylene, diethylsilylene, methylethylsilylene, methylphenylsilylene, diphenylsilylene and dipropylsilylene. In formula (I), $R^{13}$ and $R^{14}$ may be joined together to form a 4, 5, or 6-membered ring structure. J may also be selected from cyclotrimethylenesilylene, cyclotetramethylenesilylene, and cyclopentamethylenesilylene. J may also be $(CR^{15}R^{16})_x$, where x is 1 or 2, $R^{15}$ and $R^{16}$ are each independently selected from hydrogen, substituted or unsubstituted hydrocarbyl, halocarbyl, and silylcarbyl, and $R^{15}$ and $R^{16}$, when not hydrogen, are optionally bonded together to form a ring structure. J may also be selected from dimethylmethylene, diethylmethylene, methylethylmethylene, methylphenylmethylene, diphenylmethylene and dipropylmethylene. J may also be selected from cyclotetramethylene, cyclopentamethylene, and cyclohexamethylene. J may also be ethylene or methylene.

In formula (I), x may be 1 and $R^{15}$ and $R^{16}$ may be independently selected from hydrogen, methyl, ethyl, propyl, butyl, pentyl, hexyl, heptyl, octyl, nonyl, decyl, phenyl, tolyl, benzyl, and isomers thereof. In formula (I), x may be 1 and $R^{15}$ and $R^{16}$ may be joined together to form a 4, 5, or 6-membered ring structure. In formula (I), x may also be 1 or 2 and $R^{15}$ and $R^{16}$ may be hydrogen.

In formula (II) or (III), $R^1$, $R^2$, $R^3$, $R^6$, $R^7$, $R^8$, $R^9$ and $R^{12}$ may be independently selected from hydrogen or a $C_1$-$C_5$ alkyl, preferably hydrogen; $R^4$ and $R^5$ may be independently selected from methyl, ethyl, propyl or butyl or isomers thereof, preferably n-propyl, isopropyl, methyl or ethyl, and more preferably methyl or ethyl.

In formula (II), $R^{13}$ and $R^{14}$ may be independently selected from methyl, ethyl, propyl, butyl, pentyl, hexyl, heptyl, octyl, nonyl, decyl, phenyl, tolyl, benzyl, and isomers thereof, more preferably methyl, ethyl, and phenyl. In formula II, $R^{13}$ and $R^{14}$ may be joined together to form a 4, 5, or 6-membered ring structure.

In formula (III), x may be 1 and $R^{15}$ and $R^{16}$ may be independently selected from hydrogen, methyl, ethyl, propyl, butyl, pentyl, hexyl, heptyl, octyl, nonyl, decyl, phenyl, tolyl, benzyl, and isomers thereof, preferably methyl, ethyl, and phenyl. In formula (III), x may be 1 and $R^{15}$ and $R^{16}$ may be joined together to form a 4, 5, or 6-membered ring structure.

In formula (III), $R^4$ and $R^5$ may be ethyl.

In any of formulas (I), (II), (III), or (IV), each X may be independently selected from methyl, benzyl, or halo where halo includes fluoride, chloride, bromide and iodide. For example, each X may be independently methyl or chloride.

Catalyst compounds that are particularly useful in this invention include one or more of the catalyst compounds represented by formulas Cat ID 1, Cat ID 2, Cat ID 3, and Cat ID 4:

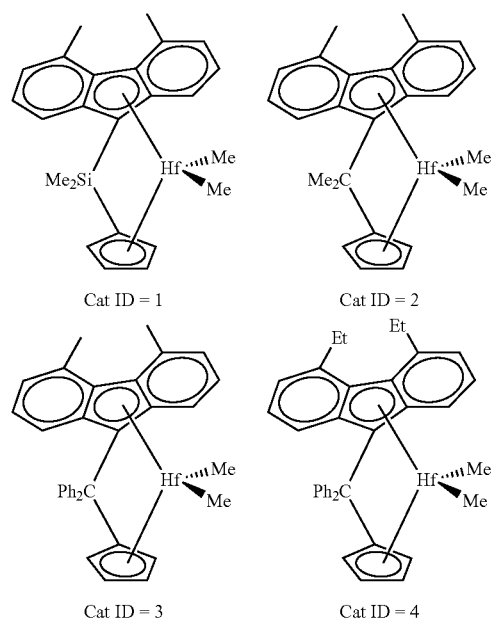

Activators

The terms "cocatalyst" and "activator" are used herein interchangeably and are defined to be any compound which can activate any one of the catalyst compounds described above by converting the neutral catalyst compound to a catalytically active catalyst compound cation. Non-limiting activators, for example, include alumoxanes, aluminum alkyls, ionizing activators, which may be neutral or ionic, and conventional-type cocatalysts. Preferred activators typically include alumoxane compounds, modified alumoxane compounds, and ionizing anion precursor compounds that abstract a reactive, σ-bound, metal ligand making the metal complex cationic and providing a charge-balancing noncoordinating or weakly coordinating anion.

Alumoxane activators may be utilized as an activator. Alumoxanes are generally oligomeric compounds containing —Al(R1)-O— sub-units, where R1 is an alkyl group. Examples of alumoxanes include methylalumoxane (MAO), modified methylalumoxane (MMAO), ethylalumoxane and isobutylalumoxane. Alkylalumoxanes and modified alkylalumoxanes are suitable as catalyst activators, particularly when the abstractable ligand is an alkyl, halide, alkoxide, or amide. Mixtures of different alumoxanes and modified alumoxanes may also be used. A visually clear methylalumoxane may be used. A cloudy or gelled alumoxane can be filtered to produce a clear solution or clear alumoxane can be decanted from the cloudy solution.

When the activator is an alumoxane (modified or unmodified), the maximum amount of activator may be a 5000-fold molar excess Al/M over the catalyst compound (per metal catalytic site). The minimum activator-to-catalyst-compound is a 1:1 molar ratio. Alternate ranges include from 1:1 to 500:1, alternately from 1:1 to 200:1, alternately from 1:1 to 100:1, or alternately from 1:1 to 50:1.

Little or no alumoxane may also be used in the polymerization processes described herein. For example, alumoxane may be present at zero mole %, or the alumoxane may be present at a molar ratio of aluminum to catalyst compound transition metal less than 500:1, less than 300:1, less than 100:1, or less than 1:1.

The term "non-coordinating anion" (NCA) means an anion which either does not coordinate to a cation or which is only weakly coordinated to a cation thereby remaining sufficiently labile to be displaced by a neutral Lewis base. The term NCA is also defined to include multicomponent NCA-containing activators, such as N,N-dimethylanilinium tetrakis(pentafluorophenyl)borate, that contain an acidic cationic group and the non-coordinating anion. The term NCA is also defined to include neutral Lewis acids, such as tris(pentafluorophenyl)boron, that can react with a catalyst to form an activated species by abstraction of an anionic group. An NCA coordinates weakly enough that a neutral Lewis base, such as an olefinically or acetylenically unsaturated monomer can displace it from the catalyst center. Any metal or metalloid that can form a compatible, weakly coordinating complex may be used or contained in the noncoordinating anion. Suitable metals include, but are not limited to, aluminum, gold, and platinum. Suitable metalloids include, but are not limited to, boron, aluminum, phosphorus, and silicon. A stoichiometric activator can be either neutral or ionic. The terms ionic activator, and stoichiometric ionic activator can be used interchangeably. Likewise, the terms neutral stoichiometric activator, and Lewis acid activator can be used interchangeably. The term non-coordinating anion includes neutral stoichiometric activators, ionic stoichiometric activators, ionic activators, and Lewis acid activators.

"Compatible" non-coordinating anions are those which are not degraded to neutrality when the initially formed complex decomposes. Further, the anion will not transfer an anionic substituent or fragment to the cation so as to cause it to form a neutral transition metal compound and a neutral by-product from the anion. Non-coordinating anions useful in this invention are those that are compatible, stabilize the transition metal cation in the sense of balancing its ionic charge at +1, and yet retain sufficient lability to permit displacement during polymerization.

It is within the scope of this invention to use an ionizing or stoichiometric activator, neutral or ionic, such as tri (n-butyl) ammonium tetrakis (pentafluorophenyl) borate, a trisperfluorophenyl boron metalloid precursor or a tris perfluoronaphthyl boron metalloid precursor, polyhalogenated heteroborane anions (WO 98/43983), boric acid (U.S. Pat. No. 5,942,459), or combination thereof. It is also within the scope of this invention to use neutral or ionic activators alone or in combination with alumoxane or modified alumoxane activators.

Boron-containing NCA activators represented by the formula below may be used:

$$(Z)_d^+(A^{d-})$$

wherein Z is (L-H) or a reducible Lewis Acid, L is a neutral Lewis base; H is hydrogen; $(L-H)^+$ is a Bronsted acid; $A^{d-}$ is a non-coordinating anion having the charge d–; and d is an integer from 1 to 3.

When Z is (L-H) such that the cation component is $(L-H)_d+$, the cation component may include Bronsted acids, such as protonated Lewis bases capable of protonating a moiety, such as an alkyl or aryl, from the bulky ligand metallocene containing transition metal catalyst precursor, resulting in a cationic transition metal species. When Z is a reducible Lewis acid it may be represented by the formula: $(Ar_3C^+)$, where Ar is aryl or aryl substituted with a heteroatom, a $C_1$ to $C_{40}$ hydrocarbyl, or a substituted $C_1$ to $C_{40}$ hydrocarbyl, preferably the reducible Lewis acid is represented by the formula: $(Ph_3C^+)$, where Ph is phenyl or phenyl substituted with a heteroatom, a $C_1$ to $C_{40}$ hydrocarbyl, or a substituted $C_1$ to $C_{40}$ hydrocarbyl. The reducible Lewis acid may be triphenyl carbenium.

The anion component $A^{d-}$ may include those having the formula $[M^{k+}Q_n]^{d-}$ wherein k is 1, 2, or 3; n is 1, 2, 3, 4, 5, or 6, preferably 3, 4, 5 or 6; n–k=d; M is an element selected from Group 13 of the Periodic Table of the Elements, preferably boron or aluminum, and Q is independently a hydride, bridged or unbridged dialkylamido, halide, alkoxide, aryloxide, hydrocarbyl, substituted hydrocarbyl, halocarbyl, substituted halocarbyl, and halosubstituted-hydrocarbyl radicals, said Q having up to 20 carbon atoms with the proviso that in not more than one occurrence is Q a halide, and two Q groups may form a ring structure. Each Q may be a fluorinated hydrocarbyl group having 1 to 20 carbon atoms, a fluorinated aryl group, or a pentafluoro aryl group. Examples of suitable $A^{d-}$ components also include diboron compounds as disclosed in U.S. Pat. No. 5,447,895, which is fully incorporated herein by reference.

In any NCAs represented by formula 2 above, the reducible Lewis acid is represented by the formula: $(Ar_3C+)$, where Ar is aryl or aryl substituted with a heteroatom, a $C_1$ to $C_{40}$ hydrocarbyl, or a substituted $C_1$ to $C_{40}$ hydrocarbyl, preferably the reducible Lewis acid is represented by the formula: $(Ph_3C+)$, where Ph is phenyl or phenyl substituted with a heteroatom, a $C_1$ to $C_{40}$ hydrocarbyl, or a substituted $C_1$ to $C_{40}$ hydrocarbyl.

Bulky activators may also be useful herein. A "Bulky activator" as used herein refers to anionic activators represented by the formula:

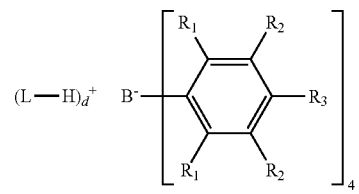

where:
each $R_1$ is, independently, a halide, preferably a fluoride;
each $R_2$ is, independently, a halide, a $C_6$ to $C_{20}$ substituted aromatic hydrocarbyl group or a siloxy group of the formula —O—Si—$R_a$, where $R_a$ is a $C_1$ to $C_{20}$ hydrocarbyl or hydrocarbylsilyl group (preferably $R_2$ is a fluoride or a perfluorinated phenyl group);
each $R_3$ is a halide, $C_6$ to $C_{20}$ substituted aromatic hydrocarbyl group or a siloxy group of the formula —O—Si—$R_a$, where $R_a$ is a $C_1$ to $C_{20}$ hydrocarbyl or hydrocarbylsilyl group (preferably $R_3$ is a fluoride or a $C_6$ perfluorinated aromatic hydrocarbyl group); wherein $R_2$ and $R_3$ can form one or more saturated or unsaturated, substituted or unsubstituted rings (preferably $R_2$ and $R_3$ form a perfluorinated phenyl ring);

L is a neutral Lewis base; $(L-H)^+$ is a Bronsted acid; d is 1, 2, or 3;

wherein the anion has a molecular weight of greater than 1020 g/mol; and wherein at least three of the substituents on the B atom each have a molecular volume of greater than 250 cubic Å, alternately greater than 300 cubic Å, or alternately greater than 500 cubic Å.

"Molecular volume" is used herein as an approximation of spatial steric bulk of an activator molecule in solution. Comparison of substituents with differing molecular volumes allows the substituent with the smaller molecular volume to be considered "less bulky" in comparison to the substituent with the larger molecular volume. Conversely, a substituent with a larger molecular volume may be considered "more bulky" than a substituent with a smaller molecular volume.

Molecular volume may be calculated as reported in "A Simple "Back of the Envelope" Method for Estimating the Densities and Molecular Volumes of Liquids and Solids," Journal of Chemical Education, Vol. 71, No. 11, November 1994, pp. 962-964. Molecular volume (MV), in units of cubic Å, is calculated using the formula: $MV=8.3V_S$, where $V_S$ is the scaled volume. $V_S$ is the sum of the relative volumes of the constituent atoms, and is calculated from the molecular formula of the substituent using the following table of relative volumes. For fused rings, the $V_S$ is decreased by 7.5% per fused ring.

| Element | Relative Volume |
| --- | --- |
| H | 1 |
| 1st short period, Li to F | 2 |
| 2nd short period, Na to Cl | 4 |
| 1st long period, K to Br | 5 |
| 2nd long period, Rb to I | 7.5 |
| 3rd long period, Cs to Bi | 9 |

For a list of possibly useful Bulky activators please see U.S. Pat. No. 8,658,556, which is incorporated by reference herein. Additionally, an NCA activator may be chosen from the activators described in U.S. Pat. No. 6,211,105, which is incorporated by reference herein.

It is also within the scope of this invention to use activators that are a combination of alumoxanes and NCAs (see for example, U.S. Pat. Nos. 5,153,157; 5,453,410; EP 0 573 120; WO 94/07928; and WO 95/14044 which discuss the use of an alumoxane in combination with an ionizing activator).

Optional Scavengers or Co-Activators

In addition to these activator compounds, scavengers or co-activators may be used. Aluminum alkyl or organoaluminum compounds which may be utilized as scavengers or co-activators include, for example, trimethylaluminum, triethylaluminum, triisobutylaluminum, tri-n-hexylaluminum, tri-n-octylaluminum, bis(diisobutylaluminum)oxide, and diethyl zinc.

Optional Support Materials

The catalyst system may comprise an inert support material. Preferably the supported material is a porous support material, for example, talc, and inorganic oxides. Other support materials include zeolites, clays, organoclays, or any other organic or inorganic support material and the like, or mixtures thereof.

The support material may be an inorganic oxide in a finely divided form. Suitable inorganic oxide materials for use in metallocene catalyst systems herein include Groups 2, 4, 13, and 14 metal oxides, such as silica, alumina, and mixtures thereof. Other inorganic oxides that may be employed either alone or in combination with the silica, or alumina are magnesia, titania, zirconia, and the like. Other suitable support materials, however, can be employed, for example, finely divided functionalized polyolefins, such as finely divided polyethylene. Particularly useful supports include magnesia, titania, zirconia, montmorillonite, phyllosilicate, zeolites, talc, clays, and the like. Also, combinations of these support materials may be used, for example, silica-chromium, silica-alumina, silica-titania, and the like. Preferred support materials include $Al_2O_3$, $ZrO_2$, $SiO_2$, and combinations thereof, more preferably $SiO_2$, $Al_2O_3$, or $SiO_2/Al_2O_3$.

The support material, such as an inorganic oxide, may have a surface area in the range of from about 10 to about 700 m$^2$/g, pore volume in the range of from about 0.1 to about 4.0 cc/g and average particle size in the range of from about 5 to about 500 μm. The surface area of the support material may be in the range of from about 50 to about 500 m$^2$/g, pore volume of from about 0.5 to about 3.5 cc/g and average particle size of from about 10 to about 200 μm. Additionally, the surface area of the support material may be in the range is from about 100 to about 400 m$^2$/g, pore volume from about 0.8 to about 3.0 cc/g and average particle size is from about 5 to about 100 μm. The average pore size of the support material useful in the invention is in the range of from 10 to 1000 Å, preferably 50 to about 500 Å, and most preferably 75 to about 350 Å. In some embodiments, the support material is a high surface area, amorphous silica (surface area=300 m$^2$/gm; pore volume of 1.65 cm$^3$/gm).

Polymerization Processes

Monomers useful herein include substituted or unsubstituted $C_2$ to $C_{40}$ alpha olefins, $C_2$ to $C_{20}$ alpha olefins, $C_2$ to $C_{12}$ alpha olefins, and preferably ethylene, propylene, butene, pentene, hexene, heptene, octene, nonene, decene, undecene, dodecene, and isomers thereof. The monomer may comprise propylene and an optional comonomers comprising one or more ethylene or $C_4$ to $C_{40}$ olefins, preferably $C_4$ to $C_{20}$ olefins, or preferably $C_6$ to $C_{12}$ olefins. The $C_4$ to $C_{40}$ olefin monomers may be linear, branched, or cyclic. The $C_4$ to $C_{40}$ cyclic olefins may be strained or unstrained, monocyclic or polycyclic, and may optionally include heteroatoms and/or one or more functional groups. The monomer may comprise ethylene and an optional comonomers comprising one or more $C_3$ to $C_{40}$ olefins, $C_4$ to $C_{20}$ olefins, or $C_6$ to $C_{12}$ olefins. The $C_3$ to $C_{40}$ olefin monomers may be linear, branched, or cyclic. The $C_3$ to $C_{40}$ cyclic olefins may be strained or unstrained, monocyclic or polycyclic, and may optionally include heteroatoms and/or one or more functional groups.

Exemplary $C_2$ to $C_{40}$ olefin monomers and optional comonomers include ethylene, propylene, butene, pentene, hexene, heptene, octene, nonene, decene, undecene, dodecene, norbornene, norbornadiene, dicyclopentadiene, cyclopentene, cycloheptene, cyclooctene, cyclooctadiene, cyclododecene, 7-oxanorbornene, 7-oxanorbornadiene, substituted derivatives thereof, and isomers thereof, preferably hexene, heptene, octene, nonene, decene, dodecene, cyclooctene, 1,5-cyclooctadiene, 1-hydroxy-4-cyclooctene, 1-acetoxy-4-cyclooctene, 5-methylcyclopentene, cyclopentene, dicyclopentadiene, norbornene, norbornadiene, and their respective homologs and derivatives, preferably norbornene, norbornadiene, and dicyclopentadiene.

One or more dienes may be present in the polymer produced herein at up to 10 weight %, preferably at 0.00001 to 1.0 weight %, preferably 0.002 to 0.5 weight %, even more preferably 0.003 to 0.2 weight %, based upon the total weight of the composition. In some embodiments 500 ppm or less of diene is added to the polymerization, preferably 400 ppm or less, preferably or 300 ppm or less. In other embodiments at least 50 ppm of diene is added to the polymerization, or 100 ppm or more, or 150 ppm or more.

Preferred diolefin monomers useful in this invention include any hydrocarbon structure, preferably $C_4$ to $C_{30}$, having at least two unsaturated bonds, wherein at least two of the unsaturated bonds are readily incorporated into a polymer by either a stereospecific or a non-stereospecific catalyst(s). It is further preferred that the diolefin monomers be selected from alpha, omega-diene monomers (i.e., di-vinyl monomers). More preferably, the diolefin monomers are linear di-vinyl monomers, most preferably those containing from 4 to 30 carbon atoms. Examples of preferred dienes include butadiene, pentadiene, hexadiene, heptadiene, octadiene, nonadiene, decadiene, undecadiene, dodecadiene, tridecadiene, tetradecadiene, pentadecadiene, hexadecadiene, heptadecadiene, octadecadiene, nonadecadiene, icosadiene, heneicosadiene, docosadiene, tricosadiene, tetracosadiene, pentacosadiene, hexacosadiene, heptacosadiene, octacosadiene, nonacosadiene, triacontadiene, particularly preferred dienes include 1,6-heptadiene, 1,7-octadiene, 1,8-nonadiene, 1,9-decadiene, 1,10-undecadiene, 1,11-dodecadiene, 1,12-tridecadiene, 1,13-tetradecadiene, and low molecular weight polybutadienes (Mw less than 1000 g/mol). Preferred cyclic dienes include cyclopentadiene, 5-vinyl-2-norbornene, norbornadiene, 5-ethylidene-2-norbornene, divinylbenzene, dicyclopentadiene or higher ring containing diolefins with or without substituents at various ring positions.

Preferred monomers may include 1) propylene alone, or 2) ethylene and propylene together, or 3) ethylene, propylene and 5-ethylidene-2-norbornene together.

Polymerization processes of this invention can be carried out in any manner known in the art. Any suspension, homogeneous, bulk, solution, slurry, or gas phase polymerization process known in the art can be used. Such processes can be run in a batch, semi-batch, or continuous mode. Homogeneous polymerization processes and slurry processes are preferred. A bulk homogeneous process is particularly preferred. A bulk process is defined to be a process where monomer concentration in all feeds to the reactor is 70 volume % or more. Alternately, no solvent or diluent is present or added in the reaction medium (except for the small amounts used as the carrier for the catalyst system or other additives, or amounts typically found with the monomer; e.g., propane in propylene). In another embodiment, the process is a slurry process. As used herein the term "slurry polymerization process" means a polymerization process where a supported catalyst is employed and monomers are polymerized on the supported catalyst particles. At least 95 wt % of polymer products derived from the supported catalyst are in granular form as solid particles (not dissolved in the diluent). Suitable diluents/solvents for polymerization include non-coordinating, inert liquids.

The feed concentration of the monomers and comonomers for the polymerization may be 60 vol % solvent or less, preferably 40 vol % or less, or preferably 20 vol % or less, based on the total volume of the feedstream. Preferably the polymerization is run in a bulk process.

Polymerizations can be run at any temperature and/or pressure suitable to obtain the desired polymers. Typical temperatures and/or pressures include a temperature in the range of from about 0° C. to about 300° C., preferably about 20° C. to about 200° C., preferably about 60° C. to about 180° C., preferably from about 70° C. to about 170° C., preferably from about 80° C. to about 160° C.; and at a pressure in the range of from about 0.35 MPa to about 10 MPa, preferably from about 0.45 MPa to about 6 MPa, or preferably from about 0.5 MPa to about 4 MPa.

Hydrogen may be present in the polymerization reactor at a partial pressure of 0.001 to 50 psig (0.007 to 345 kPa), preferably from 0.01 to 25 psig (0.07 to 172 kPa), more preferably 0.1 to 10 psig (0.7 to 70 kPa).

Other additives may also be used in the polymerization, as desired, such as one or more scavengers, promoters, modifiers, chain transfer agents (such as diethyl zinc), reducing agents, oxidizing agents, hydrogen, aluminum alkyls, or silanes.

In a typical polymerization, the run time of the reaction is up to 300 minutes, preferably in the range of from about 5 to 250 minutes, or preferably from about 10 to 120 minutes. Alternatively, the run time of reaction may preferably be in a range of 5 to 30 minutes when a solution process is employed. The run time of reaction is preferably in a range of 30 to 180 minutes when a slurry or gas phase process is employed. The run time of reaction and reactor residence time are used interchangeably herein.

Vinyl terminated polymers may be obtained by polymerizing one or more monomers in the presence of a catalyst system of the invention. For example, vinyl terminated polymers may be formed by contacting monomers comprising ethylene, propylene and/or butene, and optionally one or more dienes, with a catalyst system according to the invention, thereby forming an EPDM vinyl terminated polymer.

Polyolefin Products

The process described herein may produce propylene homopolymers or propylene copolymers, such as propylene-ethylene and/or propylene-alphaolefin (such as $C_4$ to $C_{20}$) copolymers (such as propylene-hexene copolymers or propylene-octene copolymers) having an Mw/Mn of greater than 1 to 4 or greater than 1 to 3.

Likewise, the polymers produced herein may be homopolymers of ethylene, or copolymers of ethylene preferably having from 0 to 25 mole %, 0.5 to 20 mole %, 1 to 15 mole %, or 3 to 10 mole % of one or more $C_3$ to $C_{20}$ olefin comonomer (preferably $C_3$ to $C_{12}$ alpha-olefin, preferably propylene, butene, hexene, octene, decene, dodecene, preferably propylene, butene, hexene, octene).

Likewise, the polymers produced herein may be ethylene-diene copolymers having from 0 to 25 mole %, 0.5 to 20 mole %, 1 to 15 mole %, or 3 to 10 mole % of one or more $C_6$ to $C_{12}$ non-conjugated diene, such as 1,4-hexadiene or 5-ethylidenebicyclo[2.2.1]hept-2-ene.

The polymers produced herein may have an Mw of 4,000 to 5,000,000 g/mol; 10,000 to 2,000,000 g/mol; 25,000 to 750,000 g/mol; or 50,000 to 500,000 g/mol; and/or an Mw/Mn of 1 to 40, 1.2 to 20, 1.3 to 10, 1.4 to 5, 1.5 to 4, or 1.5 to 3.

The polymers produced herein may have at least 50% allyl chain ends and/or 3-alkyl chain ends, at least 55%, at least 60%, at least 65%, at least 70%, at least 75%, at least 80%, or at least 85% allyl chain ends and/or 3-alkyl chain ends.

An allyl chain end is represented by CH₂CH═CH₂—, as shown in the formula below:

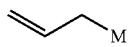

where M represents the polymer chain. "Allylic vinyl group," "allyl chain end," "vinyl chain end," "vinyl termination," "allylic vinyl group," and "vinyl terminated" are used interchangeably in the following description. The number of allyl chain ends, vinylidene chain ends, vinylene chain ends, and other unsaturated chain ends is determined using $^1$H NMR at 120° C. using deuterated tetrachloroethane as the solvent on an at least 250 MHz NMR spectrometer, and in selected cases, confirmed by $^{13}$C NMR. Resconi has reported proton and carbon assignments (neat perdeuterated tetrachloroethane used for proton spectra, while a 50:50 mixture of normal and perdeuterated tetrachloroethane was used for carbon spectra; all spectra were recorded at 100° C. on a BRUKER spectrometer operating at 500 MHz for proton and 125 MHz for carbon) for vinyl terminated oligomers in *J. American Chemical Soc.*, 114, 1992, pp. 1025-1032 that are useful herein. Allyl chain ends are reported as a molar percentage of the total number of moles of unsaturated groups (that is, the sum of allyl chain ends, vinylidene chain ends, vinylene chain ends, and the like).

A 3-alkyl chain end (where the alkyl is a $C_1$ to $C_{38}$ alkyl), also referred to as a "3-alkyl vinyl end group" or a "3-alkyl vinyl termination," is represented by the formula:

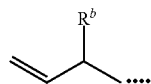

3-alkyl vinyl end group where "••••" represents the polyolefin chain and $R^b$ is a $C_1$ to $C_{38}$ alkyl group, or a $C_1$ to $C_{20}$ alkyl group, such as methyl, ethyl, propyl, butyl, pentyl, hexyl, heptyl, octyl, nonyl, decyl, undecyl, dodecyl, and the like. The amount of 3-alkyl chain ends is determined using $^{13}$C NMR as set out below.

$^1$H NMR is used to determine polymer end-group unsaturation. $^1$H NMR data is collected at either room temperature or 120° C. (for purposes of the claims, 120° C. shall be used) in a 5 mm probe using a Varian spectrometer with a $^1$H frequency of 250 MHz, 400 MHz, or 500 MHz (for the purpose of the claims, a proton frequency of 500 MHz is used and the polymer sample is dissolved in 1,1,2,2-tetrachloroethane-$d_2$ (TCE-$d_2$) and transferred into a 5 mm glass NMR tube). Data are recorded using a maximum pulse width of 45° C., 5 seconds between pulses and signal averaging 120 transients. Spectral signals are integrated and the number of unsaturation types per 1000 carbons is calculated by multiplying the different groups by 1000 and dividing the result by the total number of carbons. The chemical shift regions for the olefin types are defined to be between the following spectral regions.

| Unsaturation Type | Region (ppm) | Number of hydrogens per structure |
|---|---|---|
| Vinyl | 4.98-5.13 | 2 |
| Vinylidene (VYD) | 4.69-4.88 | 2 |
| Vinylene | 5.31-5.55 | 2 |
| Trisubstituted | 5.11-5.30 | 1 |

The polymer produced herein may be a propylene homopolymer, or a copolymer of ethylene and propylene, where in the copolymer comprises from 0.1 to 50 wt % ethylene and having: 1) at least 50%, 60%, or 70% allyl chain ends and/or 3-alkyl chain ends relative to the total number of unsaturated chain ends; 2) an Mw of 4000, 5000, or 10,000 g/mol or more; and 3) a $g'_{vis}$ of 0.90 or less.

The polymer produced herein may be a syndiotactic propylene homopolymer having: 1) at least 50%, 60%, or 70% allyl chain ends and/or 3-alkyl chain ends relative to the total number of unsaturated chain ends; 2) an Mw of 4000, 5000, or 10,000 g/mol or more; and 3) having no detectable melting temperature by DSC.

The polymer produced herein may be an ethylene-propylene copolymer, preferably having 50 wt % or more propylene, or a syndiotactic propylene polymer having: 1) a branching index ($g'_{vis}$) of 0.90, 0.87, 0.85, 0.80, 0.75, or 0.70 or less, as determined by GPC; 2) at least 50%, 60%, 65%, 70%, 75%, 80%, 85%, or 90% allyl chain ends and/or 3-alkyl chain ends; 3) an Mw from 3,000 to 500,000 g/mol, 5,000 to 300,000 g/mol, 10,000 to 200,000 g/mol, or 20,000 to 100,000 g/mol. The branching index ($g'_{vis}$) may be determined by GPC as described in USSN 2006/0173123, particularly pages 24-25.

The polymers prepared herein may be functionalized by reacting a heteroatom containing group with the polymer with or without a catalyst. Examples include catalytic hydrosilylation, ozonolysis, hydroformylation, or hydroamination, sulfonation, halogenation, hydrohalogenation, hydroboration, epoxidation, or Diels-Alder reactions with polar dienes, Friedel-Crafts reactions with polar aromatics, maleation with activators such as free radical generators (e.g., peroxides). The functionalized polymers can be used in oil additives, as anti-fogging or wetting additives, adhesion promoters, and many other applications. Preferred uses include additives for lubricants and or fuels. Preferred heteroatom containing groups include, amines, aldehydes, alcohols, acids, anhydrides, sulphonates, particularly succinic acid, maleic acid and maleic anhydride.

Other uses of the functionalized polymers include as plasticizers, surfactants for soaps, detergents, fabric softeners, antistatics, etc. Preferred heteroatom containing groups include, amines, aldehydes, alcohols, acids, anhydrides, and sulphonates, particularly succinic acid, maleic acid and maleic anhydride.

The polymers produced herein may be functionalized as described in U.S. Pat. No. 6,022,929; A. Toyota, T. Tsutsui, and N. Kashiwa, Polymer Bulletin 48, 213-219, 2002; and J. Am. Chem. Soc., 1990, 112, 7433-7434.

Blends

The polymers produced herein may be combined with one or more additional polymers prior to being formed into a film, molded part or other article. Useful polymers for a blend include polyethylene, isotactic polypropylene, highly isotactic polypropylene, syndiotactic polypropylene, random copolymer of propylene and ethylene, and/or butene, and/or hexene, polybutene, ethylene vinyl acetate, LDPE, LLDPE, HDPE, ethylene vinyl acetate, ethylene methyl acrylate, copolymers of acrylic acid, polymethylmethacrylate or any other polymers polymerizable by a high-pressure free radical process, polyvinylchloride, polybutene-1, isotactic polybutene, ABS resins, ethylene-propylene rubber (EPR), vulcanized EPR, EPDM, block copolymer, styrenic block copolymers, polyamides, polycarbonates, PET resins, cross linked polyethylene, copolymers of ethylene and vinyl alcohol (EVOH), polymers of aromatic monomers such as polystyrene, poly-1 esters, polyacetal, polyvinylidine fluoride, polyethylene glycols, and/or polyisobutylene.

The polymer, preferably polypropylene, may be present in the blends, at from 10 to 99 wt %, 20 to 95 wt %, 30 to 90 wt %, 40 to 90 wt %, 50 to 90 wt %, 60 to 90 wt %, or 70 to 90 wt %, based upon the weight of the polymers in the blend.

The blends described above may be produced by mixing the polymers of the invention with one or more polymers (as described above), by connecting reactors together in series to make reactor blends or by using more than one catalyst in the same reactor to produce multiple species of polymer. The polymers can be mixed together prior to being put into the extruder or may be mixed in an extruder.

The blends may be formed using conventional equipment and methods, such as by dry blending the individual components and subsequently melt mixing in a mixer, or by mixing the components together directly in a mixer, such as, for example, a Banbury mixer, a Haake mixer, a Brabender internal mixer, or a single or twin-screw extruder, which may include a compounding extruder and a side-arm extruder used directly downstream of a polymerization process, which may include blending powders or pellets of the resins at the hopper of the film extruder. Additionally, additives may be included in the blend, in one or more components of the blend, and/or in a product formed from the blend, such as a film, as desired. Such additives are well known in the art, and can include, for example: fillers; antioxidants (e.g., hindered phenolics such as IRGANOX™ 1010 or IRGANOX™ 1076 available from Ciba-Geigy); phosphites (e.g., IRGAFOS' 168 available from Ciba-Geigy); anti-cling additives; tackifiers, such as polybutenes, terpene resins, aliphatic and aromatic hydrocarbon resins, alkali metal and glycerol stearates, and hydrogenated rosins; UV stabilizers; heat stabilizers; anti-blocking agents; release agents; anti-static agents; pigments; colorants; dyes; waxes; silica; fillers; talc; and the like.

Applications

Specifically, any of the foregoing polymers, such as the foregoing polypropylenes or blends thereof, may be used in a variety of end-use applications. The polymers described herein may be useful in making pipes, films, blow molded articles, and rotomolded articles. Methods for producing pipes from polyethylenes are well known in the art. Any size extruder suitable for extruding the multimodal polyethylene for forming a pipe can be used. Additional applications include, for example, mono- or multi-layer blown, extruded, and/or shrink films. These films may be formed by any number of well known extrusion or coextrusion techniques, such as a blown bubble film processing technique, wherein the composition can be extruded in a molten state through an annular die and then expanded to form a uni-axial or biaxial orientation melt prior to being cooled to form a tubular, blown film, which can then be axially slit and unfolded to form a flat film. Films may be subsequently unoriented, uniaxially oriented, or biaxially oriented to the same or different extents. One or more of the layers of the film may be oriented in the transverse and/or longitudinal directions to the same or different extents.

Experimental

The following materials were used as received: 2.5 M nBuLi in hexanes (Chemetall GmbH), 1.6 M nBuLi in hexanes (Aldrich), HfCl$_4$ (Strem), tetrahydrofuran (THF, Merck), diethyl ether (Merck), ethyl acetate (Merck), methanol (Merck), ethanol (Merck), pentane (Aldrich), hexane (Merck), heptane (Aldrich), toluene (Merck), dichloromethane (Merck or Aldrich), dichlorodimethylsilane (Merck), 2.7 M CH3MgBr in diethyl ether (Aldrich), P2O5 (Merck), polyphosphoric acid (Aldrich), Na$_2$SO$_4$ (Akzo Nobel), 5% Pd/C (Aldrich), hydrogen gas (Linde), silica gel 60 (40-63 um; Merck), Celite 503 (Aldrich), CDCl$_3$ (Deutero GmbH).

Methylcyclohexane (Merck) was freshly distilled over sodium metal. Pentane (Merck) was freshly distilled over P$_4$O$_{10}$. Diethyl ether and tetrahydrofuran for air-free reactions were freshly distilled over benzophenone ketyl. Hexane, heptane and toluene for air-free reactions were freshly distilled over CaH$_2$ (Merck). 6,6'-Dimethylbiphenyl-2,2'-dicarboxylic acid was prepared from 3-methylantranilic acid (Aldrich) as described in [*J. Organomet. Chem.*, 2002, 67, 3479]. Cyclopentadienylsodium was prepared as described in [*J. Organomet. Chem.*, 2007, 692, 3907]. 6,6'-Diethylbiphenyl-2,2'-dicarboxylic acid was prepared in a multistep synthesis starting from 2-ethylaniline (Merck) as described in [*Bull. Chem. Soc. Jpn.*, 2006, 79, 1585; 1 *Organomet. Chem.*, 1971, 36, 1398]. 1,1'-(Cyclopenta-2,4-dien-1-ylidenemethylene)dibenzene and 5-(1-methylethydene)cyclopenta-1,3-diene were prepared as described in [*Tetrahedron*, 2011, 67, 8607-8614]. Dimethylmagnesium was prepared from MeMgCl as described in *Organometallics*, 2001, 20, 1569.

Example 1—Preparation of [Dimethylsilylene(4,5-dimethylfluoren-9-yl)(cyclopentadienyl)]-hafniumdimethyl (Cat ID 1)

4,5-Dimethylfluoren-9-one

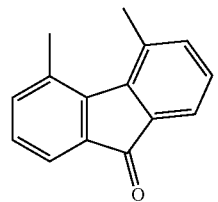 [SMILES: Cc1cccc2c1-c1c(C)cccc1C2=O]

A mixture of 200 g of polyphosphoric acid and 15.0 g of 6,6'-dimethylbiphenyl-2,2'-dicarboxylic acid was heated at 140° C. for 24 h. The resulting mixture was cooled to room temperature and poured into 1000 ml of water, and the obtained mixture was filtered. The obtained precipitate was dissolved in 300 ml of dichloromethane; the formed solution was washed with water, dried over Na$_2$SO$_4$, and then evaporated to dryness. The residue was purified by flash chromatography on silica gel 60 (40-63 um, eluent: dichloromethane). This procedure gave 5.15 g of a solid.

4,5-Dimethylfluorene

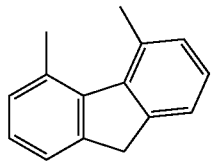

A solution of 12.4 g of 4,5-dimethylfluoren-9-one in a mixture of 200 ml of methanol, 100 ml of ethyl acetate and 10 ml of acetic acid was stirred under pressure of hydrogen (120 psi) in the presence of 5% Pd/C (2.00 g) until gas absorption is complete. The resulting mixture was filtered, and the filtrate was evaporated to dryness. The residue was purified by flash chromatography on silica gel 60 (40-63 um, eluent: hexane). This procedure gave 10.8 g of a solid.

(4,5-Dimethylfluorenyl)dimethylchlorosilane

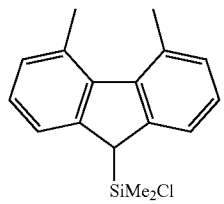

To a solution of 12.9 g of 4,5-dimethylfluorene in 150 ml of diethyl ether, 26.7 ml (66.5 mmol) of 2.5 M nBuLi in hexanes was added. The resulting mixture was stirred overnight and then evaporated to dryness. The obtained powder was added in small portions to a solution of 17.1 g of dichlorodimethylsilane in 500 ml of hexane. After that the mixture was stirred for 1 hour and filtered. The formed filtrate was evaporated to dryness in vacuum, and the residue was distilled using a Kugelrohr apparatus (b.p. 165° C./0.1 mbar). This procedure gave 14.8 g of a colorless oil.

(4,5-Dimethylfluoren-1-yl)(cyclopentadien-2,4-yl)dimethylsilane

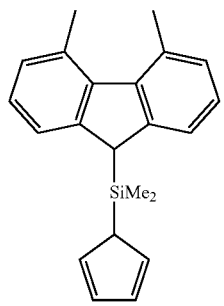

To a solution of 2.00 g of (4,5-dimethylfluorenyl)dimethylchlorosilane in 30 ml of THF, a solution of 0.67 g of cyclopentadienylsodium in 15 ml of THF was added. The resulting mixture was immediately evaporated to dryness, and crude product was extracted with 50 ml of hexane. This extract was filtered, and the filtrate was evaporated to dryness. This procedure gave 2.00 g of a colorless oil.

[Dimethylsilylene(4,5-dimethylfluoren-9-yl)(cyclopentadienyl)]hafniumdimethyl (Cat ID 1)

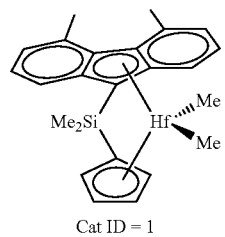

Cat ID = 1

To a solution of 2.00 g of (4,5-dimethylfluoren-1-yl)(cyclopentadien-2,4-yl)dimethylsilane in a mixture of 20 ml of diethyl ether and 20 ml of hexane cooled to 0° C., 5.00 ml of 2.5 M nBuLi in hexanes was added. The resulting mixture was stirred for 12 hours and then cooled to −50° C. Further on, 2.02 g of HfCl$_4$ was added, and this mixture was stirred for 24 hours at room temperature. The formed precipitate was separated, washed with diethyl ether/hexane mixture, and dried in vacuum. After that it was dissolved in 100 ml of toluene, and 23.5 ml (63.0 mmol) of 2.7 M CH$_3$MgBr in diethyl ether was added. This mixture was stirred in a glass pressure vessel for 12 hours at 100° C. The reaction mixture was evaporated to dryness, and crude product was extracted with 3×30 ml of hot methylcyclohexane. The combined extract was filtered, and the filtrate was evaporated to dryness. The residue was washed with n-pentane and dried in vacuum. This procedure gave 350 mg of a powder.

Anal. calc. for C$_{24}$H$_{28}$HfSi: C, 55.11; H, 5.40. Found: C, 55.00; H, 5.44.

$^1$H NMR (C$_6$D$_6$): δ 7.31 (d, J=8.3 Hz, 2H, 3,6-H in fluorenyl), 7.15 (d, J=6.8 Hz, 2H, 1,8-H in fluorenyl), 6.95 (dd, J=8.3 Hz, J=6.8 Hz, 2H, 2,7-H in fluorenyl), 6.32 (m, 2H, 3,4-H in cyclopentadienyl), 5.36 (m, 2H, 2,5-H in cyclopentadienyl), 2.75 (s, 6H, 4,5-Me), 0.63 (s, 6H, Me$_2$Si), −1.33 (s, 6H, Me$_2$Hf).

Example 2—Preparation of [dimethylmethylene(4,5-dimethylfluoren-9-yl)(cyclopentadienyl)] hafniumdimethyl (Cat ID 2)

(4,5-Dimethylfluoren-9-yl)(cyclopentadien-2,4/1,3-yl)dimethylmethane

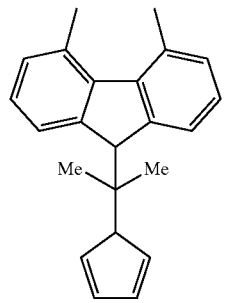 [SMILES: Cc1cccc2c1-c1c(C)cccc1C2C(C)(C)C1C=CC=C1]

To a solution of 6.00 g of 4,5-dimethylfluorene in 60 ml of THF cooled to −20° C., 12.5 ml of 2.5 M nBuLi in hexanes was added. The resulting mixture was stirred overnight and then cooled to −80° C. Further on, a solution of 3.30 g of 5-(1-methylethylidene)cyclopenta-1,3-diene was added for 30 min, and the formed mixture was stirred for 12 hours at room temperature. After that 100 ml of water was added, and THF was evaporated in vacuum. Crude product was extracted from the residue with 2×50 ml diethyl ether. The organic phase was separated, dried over $Na_2SO_4$, and evaporated to dryness. This procedure gave 8.70 g of an oil.

[Dimethylmethylene(4,5-dimethylfluoren-9-yl)(cyclopentadienyl)]hafniumdimethyl (Cat ID 2)

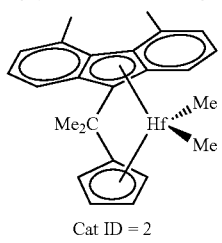

Cat ID = 2

To a solution of 3.00 g of (4,5-dimethylfluoren-9-yl)(cyclopentadien-2,4-yl)dimethylmethane in a mixture of 20 ml of diethyl ether and 20 ml of hexane cooled to 0° C., 8.80 ml of 2.5 M nBuLi in hexanes was added. The resulting mixture was stirred for 12 hours and cooled to −50° C. Then 3.20 g of $HfCl_4$ was added, and the formed mixture was stirred for 24 hours at room temperature. The resulting precipitate was separated, washed with diethyl ether/hexane mixture, and then dried in vacuum. After that it was dissolved in 200 ml of toluene, 37.0 ml of 2.7 M MeMgBr in diethyl ether was added, and the obtained mixture was stirred in a glass pressure vessel for 12 hours at 100° C. The formed mixture was evaporated to dryness, and crude product was extracted with 3×40 ml of hot methylcyclohexane. The combined extract was filtered, evaporated to about 30 ml, and then was left for crystallization. The precipitated crystals were separated and dried in vacuum. This procedure gave 3.20 g of product.

Anal. calc. for $C_{25}H_{28}Hf$: C, 59.23; H, 5.57. Found: C, 59.17; H, 5.60.

$^1H$ NMR ($C_6D_6$): δ 7.56 (d, J=8.8 Hz, 2H, 1,8-H in fluorenyl), 7.07 (d, J=6.8 Hz, 2H, 3,6-H in fluorene), 6.90 (dd, J=8.8 Hz, J=6.8 Hz, 2H, 2,7-H in fluorenyl), 6.02 (m, 2H, 3,4-H in cyclopentadienyl), 5.24 (m, 2H, 2,5-H in cyclopentadienyl), 2.68 (s, 6H, 4,5-Me), 1.87 (s, 6H, $Me_2C$), −1.29 (s, 6H, $Me_2Hf$).

Example 3—Preparation of [diphenylmethylene(4,5-dimethylfluoren-9-yl)(cyclopentadienyl)]hafniumdimethyl (Cat ID 3)

(4,5-Dimethylfluoren-9-yl)(cyclopentadien-2,4/1,3-yl)diphenylmethane

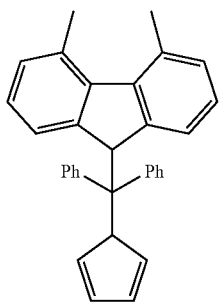 [SMILES: Cc1cccc2c1-c1c(C)cccc1C2C(c1ccccc1)(c1ccccc1)C1C=CC=C1]

2.5 M n-Butyllithium in hexanes (49.8 mL, 125 mmol, 2.0 equivalent) was added at −10° C. to a solution of 4,5-dimethylfluorene (12.1 g, 62.5 mmol, 1.0 equivalent) in THF (130 mL). The resultant solution was stirred for 15 minutes at −10° C., then at ambient temperature for 45 minutes. Then 1,1′-(Cyclopenta-2,4-dien-1-ylidenemethylene)dibenzene (18.6 g, 81.2 mmol, 1.3 equivalent) was quickly added and the reaction was stirred for 1 hour. The reaction was diluted with diethyl ether (1 L) and 1N HCl (500 mL). The layers were separated and the organic layer was dried over sodium sulfate and concentrated under reduced pressure onto silica gel (20 g). The residue was purified over silica gel (100 g), eluting with a gradient of 0 to 3% ethyl acetate in heptanes. The product was triturated with methanol (25 mL), resulting in 2.4 g of solid product.

[Diphenylmethylene(4,5-dimethylfluoren-9-yl)(cyclopentadienyl)]hafniumdichloride

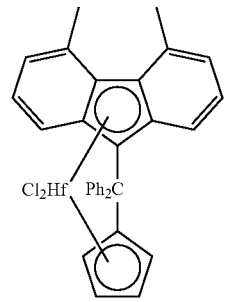

(4,5-Dimethylfluoren-9-yl)(cyclopentadien-2,4/1,3-yl)diphenylmethane (0.98 g) in 10 ml diethylether was cooled to −30° C. n-Butyl lithium (1.6 M in hexanes, 3.2 ml, 5.08 mmol) was added and the reaction was allowed to stir overnight at room temperature. The slurry was then concentrated under dry nitrogen flow, and the solid residue was triturated with pentane and filtered. The residue, dilithium (4,5-dimethylfluoren-9-yl)(cyclopentadien-2,4/1,3-yl)diphenylmethane-2($Et_2O$) was washed with pentane and dried. About 1.135 g of the salt was isolated.

Dilithium(4,5-dimethylfluoren-9-yl)(cyclopentadien-2,4/1,3-yl)diphenylmethane-2($Et_2O$) (1.135 g) was dissolved in 10 ml diethylether, and cooled to −35° C. To this, $HfCl_4$ (0.62 g) was added and the mixture was stirred at room temperature overnight. The mixture was then concentrated under a flow of dry nitrogen. The solid residue was triturated with dichloromethane and then filtered. A solution was concentrated yielding 1.24 g of solid, [diphenylmethylene (4,5-dimethylfluoren-9-yl)(cyclopentadienyl)]hafniumdichloride.

[Diphenylmethylene(4,5-dimethylfluoren-9-yl)(cyclopentadienyl)]hafniumdimethyl (Cat ID 3)

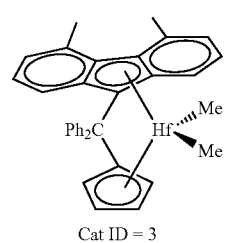

Cat ID = 3

[Diphenylmethylene(4,5-dimethylfluoren-9-yl)(cyclopentadienyl)]hafniumdichloride (0.2 g) was added to 4 ml THF. Dimethyl magnesium (20 mg) was added, and the mixture was heated to 60° C. and stirred for 18 hours. Afterwards, it was cooled and concentrated under a flow of dry nitrogen. The residue was triturated with pentane and filtered. The pentane solution was concentrated under a dry nitrogen flow and was identified as the product with minor impurities. The solid was washed with toluene and concentrated to yield 0.16 g of [Diphenylmethylene(4,5-dimethylfluoren-9-yl)(cyclopentadienyl)]hafniumdimethyl.

$^1$H NMR (C$_6$D$_6$): δ 7.78 (m, 2H), 7.68 (m, 2H), 7.23 (m, 2H), 7.07 (m, 2H), 6.98 (m, 2H), 6.9 (m, 2H), 6.60 (m, 2H), 6.47 (m, 2H), 6.06 (m, 2H), 5.47 (m, 2H), 2.75 (s, 6H), −1.37 (s, 6H).

Example 4—Preparation of [diphenylmethylene(4,5-diethylfluoren-9-yl)(cyclopentadienyl)]hafniumdimethyl (Cat ID 4)

4,5-Diethylfluoren-9-one

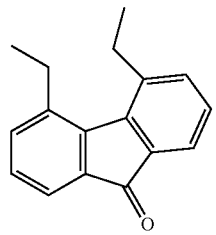 [SMILES: CCc1cccc2c1-c1c(CC)cccc1C2=O]

A mixture of 200 g of polyphosphoric acid and 13.0 g of 6,6'-diethylbiphenyl-2,2'-dicarboxylic acid was heated for 24 hours at 140° C. The resulting mixture was cooled to room temperature, poured into 1000 ml of water, and crude product was extracted with dichloromethane (2×200 ml). The organic phase was separated, washed with water, dried over Na2SO4, and then evaporated to dryness. All the volatiles were evaporated to dryness. The residue was purified by flash chromatography on silica gel 60 (40-63 um, eluent: dichloromethane). This procedure gave 6.90 g of a yellowish oil.

4,5-Diethylfluorene

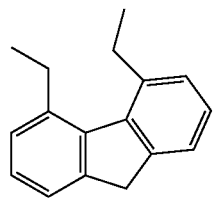 [SMILES: CCc1cccc2c1-c1c(CC)cccc1C2]

A solution of 8.00 g of 4,5-diethylfluoren-9-one in a mixture of 120 ml of methanol, 60 ml of ethyl acetate and 6 ml of acetic acid was stirred under pressure of hydrogen (120 psi) in the presence of 5% Pd/C (1.20 g) until gas absorption was complete. The resulting mixture was filtered, and the filtrate was evaporated to dryness, yielding 7.50 g of product.

(4,5-Diethylfluoren-9-yl)(cyclopentadien-2,4/1,3-yl)diphenylmethane

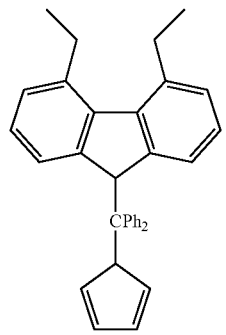

To a solution of 4.00 g of 4,5-diethylfluorene in 30 ml of diethyl ether cooled to 0° C., 7.20 ml of 2.5 M nBuLi in hexanes was added. The resulting mixture was stirred overnight and then evaporated to dryness. The residue was dissolved in 30 ml of diethyl ether, 4.15 g of 1,1'-(cyclopenta-2,4-dien-1-ylidenemethylene)dibenzene was added, and the formed mixture was stirred for 24 h. After that, 30 ml of water was added; the organic phase was separated, dried over Na$_2$SO$_4$, and evaporated to dryness. The residue was recrystallized from 40 ml of hot ethanol. The formed precipitate was separated, washed with ethanol, and dried in vacuum, yielding 5.20 g of solid.

[Diphenylmethylene(4,5-diethylfluoren-9-yl)(cyclopentadienyl)]hafniumdimethyl (Cat ID 4)

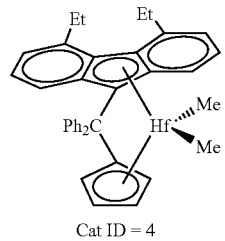

Cat ID = 4

To a solution of 3.00 g of (5,6-diethylfluoren-1-yl)(cyclopentadien-2,4-yl)diphenylmethane in a mixture of 15 ml of diethyl ether and 15 ml of hexane cooled to 0° C. 5.30 ml (6.60 mmol) of 2.5 M nBuLi in hexanes was added. The resulting mixture was stirred for 12 hours and cooled to −50° C. Then 2.11 g of HfCl$_4$ was added, and the formed mixture was stirred for 24 hours at room temperature. The resulting precipitate was separated, washed with diethylether/hexane mixture, and dried in vacuum. After that it was dissolved in 120 ml of toluene, 24.5 ml of 2.7 M MeMgBr in diethyl ether was added, and this mixture was stirred in a glass pressure vessel for 12 hours at 100° C. The reaction mixture was evaporated to dryness, and crude product was extracted 3×30 ml of hot methylcyclohexane. The combined extract was filtered and evaporated to dryness. The residue was washed with diethylether/n-pentane mixture and dried in vacuum, yielding 530 mg of powder.

Anal. calc. for C$_{37}$H$_{36}$Hf: C, 67.42; H, 5.50. Found: C, 67.45; H, 5.56.

$^1$H NMR (C$_6$D$_6$): δ 7.79 (m, 2H), 7.64 (m, 2H), 7.20 (m, 2H), 7.10 (m, 2H), 6.99 (m, 2H), 6.91 (m, 2H), 6.71 (m, 2H), 6.49 (m, 2H), 6.06 (m, 2H), 5.51 (m, 2H), 3.30-3.39 (m, 2H), 3.04-3.14 (m, 2H), 1.33 (t, 6H), −1.38 (s, 6H).

Polymerization Reactions

Activation of the pre-catalysts was either by methylalumoxane (MAO, 10 wt % in toluene, Albemarle Corp.), or dimethylanilinium tetrakisperfluorophenylborate (Boulder Scientific and Albemarle Corp). MAO was used as a 0.5 wt % or 1.0 wt % in toluene solution. Micromoles of MAO reported in the experimental section are based on the micromoles of aluminum in MAO. The formula weight of MAO is 58.0 grams/mole. When used, the molar ratio of MAO to pre-catalyst was 500. Dimethylanilinium tetrakisperfluorophenylborate was typically used as a 5 mmol/L solution in toluene. When used, the molar ratio of activator to pre-catalyst was 1.1.

For polymerization runs using dimethylanilinium tetrakisperfluorophenylborate, tri-n-octylaluminum (TnOAl, Neat, AkzoNobel) was also used as a scavenger prior to introduction of the activator and pre-catalyst into the reactor. TnOAl was typically used as a 5 mmol/L solution in toluene.

Polymerizations were conducted in an inert atmosphere drybox using autoclave reactors. The reactor internal volume was 23.5 mL for the ethylene, ethylene/octene, and ethylene/ENB runs, and 22.5 mL for the propylene and ethylene/propylene runs.

Ethylene Polymerization (PE) or Ethylene/1-Octene Copolymerization (EO)

The reactor was prepared as described above, and then purged with ethylene. For MAO activated runs, toluene (5 ml for PE and 4.9 ml for EO), 1-octene (100 μL when used), and activator (MAO) were added via syringe at room temperature and atmospheric pressure. The reactor was then brought to process temperature (80° C.) and charged with ethylene to process pressure (75 psig=618.5 kPa or 200 psig=1480.3 kPa) while stirring at 800 RPM. The pre-catalyst solution (0.25 umol pre-catalyst) was then added via syringe to the reactor at process conditions.

For dimethylanilinium tetrakisperfluorophenylborate activated runs, toluene, 1-octene (100 μL when used) and scavenger (TnOAl, 0.5 μmol) were added via syringe at room temperature and atmospheric pressure. The reactor was then brought to process temperature (80° C.) and charged with ethylene to process pressure (75 psig=618.5 kPa or 200 psig=1480.3 kPa) while stirring at 800 RPM. The activator solution, followed by the pre-catalyst solution, was injected via syringe to the reactor at process conditions. Ethylene was allowed to enter the autoclaves during polymerization to maintain reactor gauge pressure (+/−2 psig). Reactor temperature was monitored and typically maintained within +/−1° C. Polymerizations were halted by addition of approximately 50 psi O$_2$/Ar (5 mole % O$_2$) gas mixture to the autoclave for approximately 30 seconds. The polymerizations were quenched after a predetermined cumulative amount of ethylene had been added (maximum quench pressure of 20 psid ethylene uptake for PE and 20 psid ethylene uptake at 75 psig C2 or 14 psid ethylene uptake at 200 psig C2 for EO) or for a maximum of 30 minutes polymerization time. Afterwards, the reactors were cooled and vented. Polymers were isolated after the solvent was removed in-vacuo. Yields reported include total weight of polymer and residual catalyst. Ethylene homopolymerization runs are summarized in Table 1, and ethylene/1-octene copolymerization runs are summarized in Table 2.

Ethylene/ENB Copolymerization (E-ENB)

The reactor was prepared as described above, and then purged with ethylene. Isohexane (4.6 ml), ENB (50 uL) and scavenger (TnOAl, 0.075 μmol) were added via syringe at room temperature and atmospheric pressure. The reactor was then brought to process temperature (T=100° C.) and charged with ethylene to process pressure (100 psig=790.8 kPa) while stirring at 800 RPM. The activator solution (dimethylanilinium tetrakisperfluorophenylborate in toluene), followed by the pre-catalyst solution (0.08 umol pre-catalyst), were injected via syringe to the reactor at process conditions. About 336 uL of toluene was used, for a total volume in the reactor of about 5.0 mL. Ethylene was allowed to enter (through the use of computer controlled solenoid valves) the autoclaves during polymerization to maintain reactor gauge pressure (+/−2 psig). Reactor temperature was monitored and typically maintained within +/−1° C. Polymerizations were halted by addition of approximately 50 psi CO2/Ar (50/50 mol %) gas mixture to the autoclaves for approximately 30 seconds. The polymerizations were quenched after a predetermined cumulative amount of ethylene had been added (maximum quench value of 20 psid) or for a maximum of 30 minutes polymerization time. The reactors were cooled and vented. A toluene solution of 0.5 g Irgaphos168+0.5 g Irganox1076 in 20 ml toluene (50 uL) was added after quench, but prior to drying the polymer. The polymers were isolated after the solvent was removed in-vacuo. The actual polymerization time (quench time) and yields are reported in Table 3. Reported yields include total weight of polymer, residual catalyst and antioxidant.

Propylene Polymerization (PP)

The reactor was prepared as described above, then heated to 40° C., and then purged with propylene gas at atmospheric pressure. For dimethylanilinium tetrakisperfluorophenylborate activated runs, isohexanes, liquid propylene (1.0 mL) and scavenger (TnOAl, 0.5 μmol) were added via syringe. The reactor was then brought to process temperature (70, 100, 110 or 115° C.) while stirring at 800 RPM. The activator solution, followed by the pre-catalyst solution, were injected via syringe to the reactor at process conditions. Reactor temperature was monitored and typically maintained within +/−1° C. Polymerizations were halted by addition of approximately 50 psi O$_2$/Ar (5 mole % O$_2$) gas mixture to the autoclaves for approximately 30 seconds. The polymerizations were quenched based on a predetermined pressure loss of 8 psid (maximum quench value) for experiments in Table 4 and from 5 to 20 psid for experiments in Table 5 (maximum quench value in psid) or for a maximum of 30 or 45 minutes polymerization time (maximum reaction time in minutes). The reactors were cooled and vented. The polymers were isolated after the solvent was removed in-vacuo. The actual quench time (s) and quench value (psi) are reported. Yields reported include total weight of polymer and residual catalyst. Propylene homopolymerization examples are reported in Tables 4 and 5.

Ethylene-Propylene Copolymerization (EP)

The reactor was prepared as described above, then heated to 40° C. and then purged with ethylene gas at atmospheric pressure. The listed ethylene pressure (10, 20, 40, 60 or 80 psid) was then added to the reactor. Isohexanes and scavenger (TnOAl, 0.5 μmol) were added via syringe. The stirrers were then started and maintained at 800 RPM. Liquid propylene (1.0 ml) was then injected into the reactor. The reactor was then brought to process temperature (70° C.). The activator (dimethylanilinium tetrakisperfluorophenylborate) solution followed by the pre-catalyst solution, was injected via syringe to the reactor at process conditions. Reactor temperature was monitored and typically maintained within +/−1° C. Polymerizations were halted by addition of approximately 50 psi O$_2$/Ar (5 mole % O$_2$) gas mixture to the autoclaves for approximately 30 seconds. The polymerizations were quenched based on a predetermined pressure loss (from 5 to 20 psid quench value) or for a maximum of 45 minutes polymerization time. The reactors were cooled and vented. The polymer was isolated after the solvent was removed in-vacuo. The quench time (s) and max quench value (psi) are reported in Table 5 for each run.

Yields reported include total weight of polymer and residual catalyst. Ethylene/propylene copolymerization examples are collected in Table 5.

For the comparative examples, the comparative compounds used include:

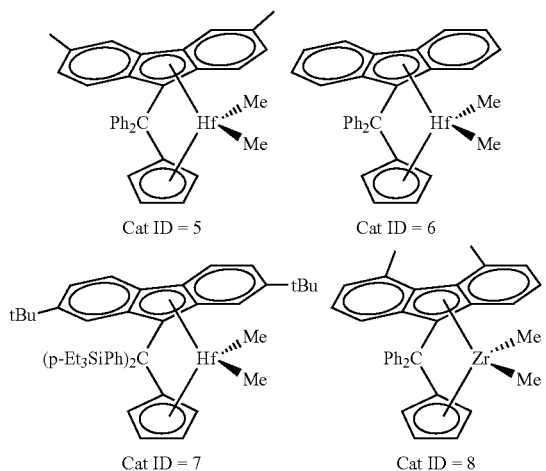

Polymer Characterization

For analytical testing, polymer sample solutions were prepared by dissolving polymer in 1,2,4-trichlorobenzene (TCB, 99+% purity from Sigma-Aldrich) containing 2,6-di-tert-butyl-4-methylphenol (BHT, 99% from Aldrich) at 165° C. in a shaker oven for approximately 3 hours. The typical concentration of polymer in solution was between 0.1 to 0.9 mg/mL with a BHT concentration of 1.25 mg BHT/mL of TCB. Samples were cooled to 135° C. for testing.

High temperature size exclusion chromatography was performed using an automated "Rapid GPC" system as described in U.S. Pat. Nos. 6,491,816; 6,491,823; 6,475,391; 6,461,515; 6,436,292; 6,406,632; 6,175,409; 6,454,947; 6,260,407; and 6,294,388; each of which is incorporated herein by reference. Molecular weights (weight average molecular weight (Mw) and number average molecular weight (Mn)) and molecular weight distribution (MWD=Mw/Mn), which is also sometimes referred to as the polydispersity (PDI) of the polymer, were measured by Gel Permeation Chromatography using a Symyx Technology GPC equipped with evaporative light scattering detector ("ELSD") and calibrated using polystyrene standards (Polymer Laboratories: Polystyrene Calibration Kit S-M-10: Mp (peak Mw) between 5000 and 3,390,000). Samples (250 μL of a polymer solution in TCB were injected into the system) were run at an eluent flow rate of 2.0 mL/minute (135° C. sample temperatures, 165° C. oven/columns) using three Polymer Laboratories: PLgel 10 μm Mixed-B 300×7.5 mm columns in series. No column spreading corrections were employed. Numerical analyses were performed using Epoch® software available from Symyx Technologies. The molecular weights obtained are relative to linear polystyrene standards. Molecular weight data is reported in Tables 1, 2, 3, 4, and 5 under the headings Mn, Mw and PDI as defined above. PDI values marked with an astrick indicate that this method was used for Mn, Mw and PDI values.

Alternatively, molecular weights (weight average molecular weight (Mw) and number average molecular weight (Mn)) and molecular weight distribution (MWD=Mw/Mn), which is also sometimes referred to as the polydispersity (PDI) of the polymer, were measured by Gel Permeation Chromatography using a Symyx Technology GPC equipped with dual wavelength infrared detector and calibrated using polystyrene standards (Polymer Laboratories: Polystyrene Calibration Kit S-M-10: Mp (peak Mw) between 580 and 3,039,000). Samples (250 μL of a polymer solution in TCB were injected into the system) were run at an eluent flow rate of 2.0 mL/minute (135° C. sample temperatures, 165° C. oven/columns) using three Polymer Laboratories: PLgel 10 μm Mixed-B 300×7.5 mm columns in series. No column spreading corrections were employed. Numerical analyses were performed using Automation Studio software available from Freeslate. The molecular weights obtained are relative to linear polystyrene standards. Molecular weight data is reported in Tables 1, 2, 3, 4, and 5 under the headings Mn, Mw and PDI as defined above. PDI values not marked with an asterisk indicate that this method was used for Mn, Mw and PDI values.

Differential Scanning calorimetry (DSC) measurements were performed on a TA-Q100 instrument to determine the melting point of the polymers. Samples were pre-annealed at 220° C. for 15 minutes and then allowed to cool to room temperature overnight. The samples were then heated to 220° C. at a rate of 100° C./minute and then cooled at a rate of 50° C./minute. Melting points were collected during the heating period. The results are reported in the Tables 1, 2, and 3 under the heading, Tm (° C.). The polypropylene and ethylene-propylene copolymer produced (see Tables 4 and %) are largely amorphous polyolefins. Most exhibited no crystallinity, and the few that did, had low delta H crystallization values (7 J/g or less).

Samples for infrared analysis were prepared by depositing the stabilized polymer solution onto a silanized wafer (Part number S10860, Symyx). By this method, approximately between 0.12 and 0.24 mg of polymer is deposited on the wafer cell. The samples were subsequently analyzed on a Brucker Equinox 55 FTIR spectrometer equipped with Pikes' MappIR specular reflectance sample accessory. Spectra, covering a spectral range of 5000 $cm^{-1}$ to 500 $cm^{-1}$, were collected at a 2 $cm^{-1}$ resolution with 32 scans.

For ethylene-1-octene copolymers, the wt % octene in the copolymer was determined via measurement of the methyl deformation band at ~1375 $cm^{-1}$. The peak height of this band was normalized by the combination and overtone band at ~4321 $cm^{-1}$, which corrects for path length differences. The normalized peak height was correlated to individual calibration curves from 1H NMR data to predict the wt % octene content within a concentration range of ~2 to 35 wt % for octene. Typically, $R^2$ correlations of 0.98 or greater are achieved. These numbers are reported in Table 2 under the heading C8 wt %).

For ethylene-propylene copolymers, the wt % ethylene was determined via measurement of the methylene rocking band (~770 $cm^{-1}$ to 700 $cm^{-1}$). The peak area of this band was normalized by sum of the band areas of the combination and overtone bands in the 4500 $cm^{-1}$ to 4000 $cm^{-1}$ range. The normalized band area was then correlated to a calibration curve from $^{13}C$ NMR data to predict the wt % ethylene within a concentration range of ~5 to 40 wt %. Typically, $R^2$ correlations of 0.98 or greater were achieved. These numbers are reported in Table 5 under the heading $C_2$ wt %.

For ethylene-ENB copolymers, polymer composition analysis was determined by $^1H$ NMR using a Varian DD2 500 MHz instrument run with a single 30° flip angle RF pulse, 512 scans with a delay of 15 seconds between pulses. The polymer sample was dissolved in heated $d_2$-1,1,2,2-tetrachloroethane and signal collection took place at 120° C.

For calculation of ENB:

$I_{major}$=Integral of major ENB species from 5.2-5.4 ppm
$I_{minor}$=Integral of minor ENB species from 4.6-5.12 ppm
$I_{eth}$=(Integral of —$CH_2$— from 0-3 ppm)

| Peak Assignments | Intensity of species | MOLE % | WEIGHT % |
|---|---|---|---|
| Olef: 5.3 and 5.1 ppm ENB | ENB = $I_{major}$ + $I_{minor}$ | ENB*100/total | ENB*120*100/total wt |
| EP: 3-0 ppm | EP = ($I_{eth}$ − 11*ENB)/2 | EP*100/total | EP*14*100/total wt | total = (ENB + EP)
total wt = (ENB*120 + EP*14)

For some samples, polymer end-group analysis was determined by $^1$H NMR using a Varian Unity+400 MHz instrument run with a single 30° flip angle, RF pulse. 120 pulses with a delay of 8 seconds between pulses were signal averaged. The polymer sample was dissolved in heated $d_2$-1,1,2,2-tetrachloroethane and signal collection took place at 120° C. Vinylenes were measured as the number of vinylenes per 1000 carbon atoms using the resonances between 5.55-5.31 ppm. Trisubstituted end-groups ("trisubs") were measured as the number of trisubstituted groups per 1000 carbon atoms using the resonances between 5.30-5.11 ppm. Vinyl end-groups were measured as the number of vinyls per 1000 carbon atoms using the resonances between 5.13-4.98 ppm. Vinylidene end-groups were measured as the number of vinylidenes per 1000 carbon atoms using the resonances between 4.88-4.69 ppm.

The values reported in Tables 4 and 5 are % vinylene, % trisubstituted (% trisub), % vinyl and % vinylidene, where the percentage is relative to the total olefinic unsaturation per 1000 carbon atoms.

Polymerization results are also reported in Tables 1 to 5 below. The following abbreviations are used herein: PE=polyethylene, EO=ethylene-1-octene copolymer, ENB=ethylene-ethylidenenorbornene copolymer, PP=polypropylene, EP=ethylene-propylene copolymer; CPE=comparative polyethylene, CEO=comparative ethylene-1-octene copolymer, CENB=comparative ethylene-ethylidenenorbornene copolymer, CPP=comparative polypropylene, CEP=comparative ethylene-propylene copolymer. Examples starting with a "C" as in CPP and CEP are comparative examples. "Cat ID" identifies the pre-catalyst used in the experiment. Corresponding numbers identifying the pre-catalyst are located in the synthetic experimental section. "Act ID" identifies the activator used. "A" corresponds to dimethylanilinium tetrakisperfluorophenylborate, and "B" corresponds to MAO. "Cat (μmol)" is the amount of pre-catalyst added to the reactor. For all experiments using MAO as the activator, the molar ratio of activator/pre-catalyst was 500. For all experiments using borate activators (A), the molar ratio of activator/pre-catalyst was 1.1. T(° C.) is the polymerization temperature which was typically maintained within +/−1° C. "Yield" is polymer yield, and is not corrected for catalyst residue (or antioxidant if added). "Quench time (s)" is the actual duration of the polymerization run in seconds. "Quench Value (psid)" for ethylene based polymerization runs (except EP) is the set maximum amount of ethylene uptake (conversion) for the experiment. If a polymerization quench time is less than the maximum time set, then the polymerization ran until the set maximum value of ethylene uptake was reached. For propylene homopolymerization runs and ethylene-propylene copolymeriztion runs, quench value indicates the maximum set pressure loss (conversion) of propylene (for PP) or propylene and ethylene (for EP), during the polymerization. Quench time is the actual time of the polymerization run in seconds. Activity is reported as grams polymer per mmol of catalyst per hour.

TABLE 1

Polymerization Examples Producing Polyethylene

| Ex # | Cat ID | Act ID | Quench Time (s) | Yield (g) | Activity (g P/mmol cat · hr) | Mn | Mw | PDI | Tm (° C.) |
|---|---|---|---|---|---|---|---|---|---|
| PE-1  | 1 | A | 17   | 0.0912 | 791,133   | 1,391,159 | 2,621,710 | 1.88  | 136.1 |
| PE-2  | 1 | A | 27   | 0.0828 | 449,932   | 1,334,992 | 2,517,369 | 1.89  | 136.2 |
| PE-3  | 1 | A | 16   | 0.0947 | 857,660   | 1,108,370 | 2,406,614 | 2.17  | 136.4 |
| PE-4  | 1 | B | 225  | 0.0440 | 28,160    | 768,687   | 1,404,407 | 1.83  | 135.3 |
| PE-5  | 1 | B | 361  | 0.0540 | 21,540    | 791,154   | 1,324,253 | 1.67  | 135.2 |
| PE-6  | 1 | B | 301  | 0.0520 | 24,877    | 820,382   | 1,434,818 | 1.75  | 135.4 |
| PE-7  | 2 | A | 170  | 0.0489 | 41,494    | 1,483,077 | 2,553,753 | 1.72  | 136.2 |
| PE-8  | 2 | A | 1802 | 0.0716 | 5,721     | 1,655,755 | 2,822,352 | 1.70  | 136.3 |
| PE-9  | 2 | A | 176  | 0.0455 | 37,248    | 1,505,384 | 2,513,903 | 1.67  | 136.1 |
| PE-10 | 2 | B | 462  | 0.0250 | 7,792     | 447,637   | 867,469   | 1.94  | 134.9 |
| PE-11 | 2 | B | 524  | 0.0350 | 9,618     | 527,603   | 1,014,173 | 1.92  | 134.9 |
| PE-12 | 2 | B | 513  | 0.0330 | 9,263     | 594,527   | 1,001,863 | 1.69  | 134.6 |
| PE-13 | 3 | A | 18   | 0.1001 | 814,373   | 2,337,392 | 3,756,324 | 1.61* | 135.3 |
| PE-14 | 3 | A | 23   | 0.0801 | 512,640   | 2,352,584 | 2,856,265 | 1.21* | 134.0 |
| PE-15 | 3 | A | 15   | 0.0932 | 871,481   | 2,876,181 | 4,620,414 | 1.61* | 135.1 |
| PE-16 | 4 | A | 33   | 0.0910 | 398,298   | 2,362,572 | 3,925,347 | 1.66  | 135.2 |
| PE-17 | 4 | A | 23   | 0.0858 | 541,895   | 2,046,427 | 3,497,406 | 1.71  | 134.1 |
| PE-18 | 4 | A | 141  | 0.0862 | 88,034    | 1,782,431 | 3,405,459 | 1.91  | 133.8 |
| PE-19 | 4 | B | 470  | 0.0520 | 15,932    | 663,898   | 1,097,249 | 1.65  | 135.4 |
| PE-20 | 4 | B | 375  | 0.0430 | 16,512    | 671,791   | 1,127,249 | 1.68  | 135.3 |
| PE-21 | 4 | B | 460  | 0.0590 | 18,470    | 658,341   | 1,147,485 | 1.74  | 134.7 |
| CPE-1 | 5 | A | 134  | 0.0810 | 86,980    | 2,813,996 | 3,875,109 | 1.38* | 133.6 |
| CPE-2 | 5 | A | 35   | 0.0860 | 351,818   | 2,802,129 | 4,176,917 | 1.49* | 136.2 |
| CPE-3 | 5 | A | 13   | 0.0927 | 1,034,791 | 1,952,583 | 3,225,994 | 1.65* | 133.3 |

*Rapid GPC system was used.

TABLE 2

Polymerization examples producing ethylene-octene copolymer

| Ex# | Cat ID | Act ID | C2 (psig) | Quench Time (s) | Yield (g) | Activity (g P/mmol cat · hr) | Mn | Mw | PDI | C8 (wt %) | Tm (° C.) |
|---|---|---|---|---|---|---|---|---|---|---|---|
| EO-1 | 1 | A | 75 | 1048 | 0.0657 | 9,024 | 545,785 | 1,393,938 | 2.55 | 19.1 | 94.9 |
| EO-2 | 1 | A | 75 | 665 | 0.0633 | 13,717 | 483,509 | 1,290,383 | 2.67 | 19.7 | 93.7 |
| EO-3 | 1 | A | 75 | 580 | 0.0708 | 17,581 | 445,168 | 1,280,461 | 2.88 | 20.5 | 93.6 |
| EO-4 | 1 | A | 200 | 20 | 0.1540 | 1,114,372 | 771,513 | 1,818,698 | 2.36 | 9.2 | 111.7 |
| EO-5 | 1 | A | 200 | 51 | 0.1554 | 443,121 | 689,333 | 1,756,995 | 2.55 | 8.7 | 111.4 |
| EO-6 | 1 | A | 200 | 23 | 0.1518 | 934,154 | 720,177 | 1,875,261 | 2.60 | 9.5 | 111.1 |
| EO-7 | 1 | B | 75 | 252 | 0.0410 | 23,429 | 792,725 | 1,326,953 | 1.67 | 11.4 | 103.0 |
| EO-8 | 1 | B | 75 | 374 | 0.0500 | 19,251 | 930,361 | 1,475,482 | 1.59 | 12.3 | 102.0 |
| EO-9 | 1 | B | 75 | 309 | 0.0490 | 22,835 | 828,629 | 1,391,685 | 1.68 | 12.1 | 102.6 |
| EO-10 | 1 | B | 200 | 211 | 0.0540 | 36,853 | 1,082,862 | 1,801,933 | 1.66 | 4.6 | 120.5 |
| EO-11 | 1 | B | 200 | 366 | 0.0850 | 33,443 | 1,109,917 | 1,964,526 | 1.77 | 5.5 | 116.9 |
| EO-12 | 1 | B | 200 | 340 | 0.0930 | 39,388 | 1,205,331 | 2,007,520 | 1.67 | 5.0 | 117.0 |
| EO-13 | 2 | A | 75 | 1802 | 0.0309 | 2,470 | 867,816 | 1,558,501 | 1.80 | 23.4 | 80.1 |
| EO-14 | 2 | A | 75 | 1802 | 0.0318 | 2,542 | 1,000,042 | 1,747,151 | 1.75 | 21.6 | 82.0 |
| EO-15 | 2 | A | 75 | 1803 | 0.0317 | 2,532 | 878,166 | 1,555,923 | 1.77 | 22.2 | 80.3 |
| EO-16 | 2 | A | 200 | 275 | 0.0840 | 44,033 | 1,156,637 | 2,098,940 | 1.81 | 10.3 | 106.1 |
| EO-17 | 2 | A | 200 | 348 | 0.0822 | 34,014 | 1,302,909 | 2,196,593 | 1.69 | 10.4 | 106.1 |
| EO-18 | 2 | A | 200 | 377 | 0.0828 | 31,652 | 1,341,548 | 2,241,367 | 1.67 | 10.7 | 106.6 |
| EO-19 | 2 | B | 75 | 466 | 0.0350 | 10,815 | 530,165 | 922,526 | 1.74 | 17.1 | 60.6 |
| EO-20 | 2 | B | 75 | 495 | 0.0330 | 9,600 | 537,687 | 868,603 | 1.62 | 16.7 | 93.0 |
| EO-21 | 2 | B | 75 | 495 | 0.0390 | 11,345 | 611,349 | 979,425 | 1.60 | 15.7 | 92.4 |
| EO-22 | 2 | B | 200 | 148 | 0.0310 | 30,162 | 795,718 | 1,348,200 | 1.69 | 8.8 | 111.2 |
| EO-23 | 2 | B | 200 | 174 | 0.0350 | 28,966 | 842,639 | 1,418,155 | 1.68 | 7.2 | 111.9 |
| EO-24 | 2 | B | 200 | 156 | 0.0330 | 30,462 | 815,743 | 1,394,090 | 1.71 | 7.4 | 111.6 |
| EO-25 | 3 | A | 75 | 215 | 0.1262 | 84,564 | 219,041 | 1,408,950 | 6.43* | 34.3 | |
| EO-26 | 3 | A | 75 | 200 | 0.1268 | 91,433 | 412,105 | 1,766,806 | 4.29* | 31.5 | |
| EO-27 | 3 | A | 75 | 208 | 0.1235 | 85,336 | 3,662,377 | 5,032,475 | 1.37* | 27.3 | |
| EO-28 | 3 | A | 200 | 27 | 0.2046 | 1,099,343 | 167,150 | 2,359,916 | 14.12* | 25.8 | |
| EO-29 | 3 | A | 200 | 10 | 0.1854 | 2,810,274 | 1,193,050 | 2,813,951 | 2.36* | 15.2 | 102.7 |
| EO-30 | 3 | A | 200 | 10 | 0.1902 | 2,766,545 | 1,052,069 | 2,922,326 | 2.78* | 16.8 | 101.2 |
| EO-31 | 4 | A | 75 | 292 | 0.1196 | 59,037 | 270,045 | 1,642,275 | 6.08 | 29.6 | 98.1 |
| EO-32 | 4 | A | 75 | 308 | 0.1219 | 56,918 | 718,739 | 2,743,888 | 3.82 | 22.3 | 107.3 |
| EO-33 | 4 | A | 75 | 272 | 0.1179 | 62,533 | 240,827 | 1,555,279 | 6.46 | 32.8 | 97.4 |
| EO-34 | 4 | A | 200 | 37 | 0.1986 | 783,518 | 125,514 | 1,579,178 | 12.58 | 27.8 | 101.7 |
| EO-35 | 4 | A | 200 | 7 | 0.1688 | 3,574,588 | 1,135,354 | 2,704,862 | 2.38 | 13.2 | 103.3 |
| EO-36 | 4 | A | 200 | 34 | 0.1953 | 839,499 | 165,151 | 2,150,718 | 13.02 | 21.0 | 108.8 |
| EO-37 | 4 | B | 75 | 316 | 0.0410 | 18,684 | 735,892 | 1,233,479 | 1.68 | 19.0 | 89.2 |
| EO-38 | 4 | B | 75 | 332 | 0.0470 | 20,386 | 760,413 | 1,217,169 | 1.60 | 19.4 | 88.4 |
| EO-39 | 4 | B | 75 | 328 | 0.0490 | 21,512 | 764,212 | 1,312,165 | 1.72 | 19.9 | 87.4 |
| EO-40 | 4 | B | 200 | 260 | 0.0960 | 53,169 | 1,189,814 | 2,102,463 | 1.77 | 10.6 | 107.1 |
| EO-41 | 4 | B | 200 | 262 | 0.1020 | 56,061 | 1,256,731 | 2,141,465 | 1.70 | 9.7 | 107.6 |
| EO-42 | 4 | B | 200 | 243 | 0.0950 | 56,296 | 997,360 | 2,074,382 | 2.08 | 9.9 | 107.1 |
| CEO- | 5 | A | 75 | 234 | 0.1208 | 74,338 | 341,670 | 1,361,377 | 3.98* | 35.0 | |
| CEO- | 5 | A | 75 | 400 | 0.1181 | 42,505 | 482,310 | 1,958,443 | 4.06* | 34.5 | |
| CEO- | 5 | A | 75 | 270 | 0.1245 | 66,474 | 312,342 | 1,559,646 | 4.99* | 35.1 | |
| CEO- | 5 | A | 200 | 30 | 0.1799 | 875,189 | 837,534 | 2,994,987 | 3.58* | 20.5 | |
| CEO- | 5 | A | 200 | 27 | 0.2047 | 1,091,733 | 293,101 | 2,445,712 | 8.34* | 21.6 | |
| CEO- | 5 | A | 200 | 10 | 0.1983 | 2,913,796 | 1,009,865 | 2,427,714 | 2.40* | 16.6 | |

*Rapid GPC system was used.

TABLE 3

Polymerization examples producing ethylene-ENB copolymer

| Ex# | Cat ID | Quench Time (s) | Yield (g) | Activity (g P/mmol cat · hr) | Mn | Mw | PDI | Tm (° C.) | ENB (wt %) |
|---|---|---|---|---|---|---|---|---|---|
| ENB-1 | 1 | 50 | 0.084 | 75,600 | 340,574 | 747,652 | 2.20 | 86.2 | 12.7 |
| ENB-2 | 1 | 54 | 0.079 | 65,833 | 412,103 | 769,056 | 1.87 | 87.4 | |
| ENB-3 | 1 | 62 | 0.084 | 60,968 | 349,391 | 751,954 | 2.15 | 85.5 | 13.3 |
| ENB-4 | 1 | 47 | 0.079 | 75,638 | 376,700 | 700,630 | 1.86 | 91.0 | |
| ENB-5 | 1 | 43 | 0.080 | 83,721 | 298,191 | 660,276 | 2.21 | 92.0 | |
| ENB-6 | 1 | 41 | 0.075 | 82,317 | 316,389 | 661,025 | 2.09 | 92.1 | |
| ENB-7 | 2 | 91 | 0.063 | 31,154 | 384,718 | 833,282 | 2.17 | 71.2 | |
| ENB-8 | 2 | 75 | 0.068 | 40,800 | 449,219 | 939,147 | 2.09 | 67.1 | 8.9 |
| ENB-9 | 2 | 99 | 0.063 | 28,636 | 404,539 | 858,737 | 2.12 | 74.2 | |
| ENB-10 | 2 | 79 | 0.068 | 38,734 | 424,562 | 917,469 | 2.16 | 68.4 | 7.6 |
| ENB-11 | 2 | 102 | 0.062 | 27,353 | 432,798 | 850,147 | 1.96 | 75.1 | |
| ENB-12 | 2 | 92 | 0.060 | 29,348 | 434,042 | 836,041 | 1.93 | 75.9 | |

TABLE 3-continued

Polymerization examples producing ethylene-ENB copolymer

| Ex# | Cat ID | Quench Time (s) | Yield (g) | Activity (g P/mmol cat · hr) | Mn | Mw | PDI | Tm (° C.) | ENB (wt %) |
|---|---|---|---|---|---|---|---|---|---|
| ENB-13 | 3 | 331 | 0.052 | 7,069 | 511,231 | 1,134,946 | 2.22 | 78.2 | |
| ENB-14 | 3 | 420 | 0.055 | 5,893 | 475,510 | 1,276,750 | 2.69 | 80.7 | |
| ENB-15 | 3 | 356 | 0.052 | 6,573 | 629,291 | 1,280,669 | 2.04 | 81.4 | |
| ENB-16 | 3 | 290 | 0.058 | 9,000 | 583,626 | 1,272,630 | 2.18 | 82.2 | 10.1 |
| ENB-17 | 3 | 263 | 0.054 | 9,240 | 607,568 | 1,155,375 | 1.90 | 79.7 | 8.9 |
| ENB-18 | 3 | 195 | 0.054 | 12,462 | 575,136 | 1,149,622 | 2.00 | 80.6 | |
| ENB-19 | 4 | 154 | 0.052 | 15,195 | 622,026 | 1,160,853 | 1.87 | 79.9 | |
| ENB-20 | 4 | 150 | 0.055 | 16,500 | 724,101 | 1,254,974 | 1.73 | 79.7 | |
| ENB-21 | 4 | 181 | 0.056 | 13,923 | 608,355 | 1,249,951 | 2.05 | 81.4 | |
| ENB-22 | 4 | 108 | 0.050 | 20,833 | 642,409 | 1,172,825 | 1.83 | 79.0 | |
| ENB-23 | 4 | 104 | 0.057 | 24,663 | 626,636 | 1,035,496 | 1.65 | 85.3 | |
| ENB-24 | 4 | 61 | 0.061 | 45,000 | 582,298 | 974,007 | 1.67 | 88.8 | 12.6 |
| CENB-1 | 5 | 120 | 0.066 | 24,750 | 659,327 | 1,585,335 | 2.40 | 62.7 | |
| CENB-2 | 5 | 120 | 0.069 | 25,875 | 645,312 | 1,700,010 | 2.63 | 71.1 | 10.2 |
| CENB-3 | 5 | 294 | 0.067 | 10,255 | 567,900 | 1,485,211 | 2.62 | 69.5 | 20.0 |
| CENB-4 | 5 | 134 | 0.066 | 22,164 | 529,616 | 1,335,595 | 2.52 | 66.0 | |
| CENB-5 | 5 | 127 | 0.053 | 18,780 | 653,979 | 1,441,344 | 2.20 | 73.5 | |
| CENB-6 | 5 | 145 | 0.052 | 16,138 | 740,984 | 1,410,113 | 1.90 | 75.0 | |
| CENB-7 | 7 | 324 | 0.086 | 11,944 | 1,191,874 | 2,397,759 | 2.01 | 75.2 | 16.1 |
| CENB-8 | 7 | 277 | 0.089 | 14,458 | 1,144,088 | 2,141,240 | 1.87 | 77.3 | 11.8 |
| CENB-9 | 7 | 292 | 0.079 | 12,175 | 1,134,572 | 2,343,532 | 2.07 | 77.5 | |
| CENB-10 | 7 | 356 | 0.086 | 10,871 | 1,004,872 | 2,475,191 | 2.46 | 77.7 | |
| CENB-11 | 7 | 121 | 0.076 | 28,264 | 960,283 | 1,705,963 | 1.78 | 82.3 | |
| CENB-12 | 7 | 132 | 0.079 | 26,932 | 1,019,346 | 1,769,125 | 1.74 | 79.2 | |

TABLE 4

Polymerization examples producing polypropylene

| Ex # | Cat ID | Cat (umol) | Iso-hexane (uL) | Toluene (uL) | T (C.) | Max Rxn Time (mm) | Quench Time (s) | Yield (g) | Activity (g P/mmol cat · hr) | Mn | Mw | PDI | total unsat/ 1000 C. | % vinylene | % trisub | % vinyl | % vinylidene |
|---|---|---|---|---|---|---|---|---|---|---|---|---|---|---|---|---|---|
| PP-1 | 1 | 0.025 | 3895 | 205 | 70 | 30 | 1801 | 0.0458 | 3,662 | 46,238 | 76,840 | 1.66 | | | | | |
| PP-2 | 1 | 0.025 | 3895 | 205 | 70 | 30 | 1802 | 0.0493 | 3,939 | 56,882 | 87,796 | 1.54 | 0.72 | 6 | 8 | 60 | 26 |
| PP-3 | 1 | 0.025 | 3895 | 205 | 70 | 30 | 1801 | 0.0465 | 3,717 | 55,712 | 86,025 | 1.54 | | | | | |
| PP-4 | 1 | 0.025 | 3895 | 205 | 100 | 30 | 1801 | 0.0262 | 2,095 | 8,597 | 13,928 | 1.62 | | | | | |
| PP-5 | 1 | 0.025 | 3895 | 205 | 100 | 30 | 1802 | 0.0238 | 1,902 | 7,468 | 12,462 | 1.67 | 3.81 | 2 | 4 | 74 | 20 |
| PP-6 | 1 | 0.025 | 3895 | 205 | 100 | 30 | 1802 | 0.0217 | 1,734 | 7,281 | 11,934 | 1.64 | | | | | |
| PP-7 | 1 | 0.100 | 3690 | 410 | 100 | 45 | 460 | 0.0710 | 5,557 | 5,406 | 11,128 | 2.06 | | | | | |
| PP-8 | 1 | 0.100 | 3690 | 410 | 100 | 45 | 465 | 0.0740 | 5,729 | 6,408 | 11,958 | 1.87 | 4.00 | 1 | 3 | 77 | 19 |
| PP-9 | 1 | 0.100 | 3690 | 410 | 100 | 45 | 456 | 0.0670 | 5,289 | 4,693 | 9,566 | 2.04 | | | | | |
| PP-10 | 1 | 0.100 | 3690 | 410 | 100 | 45 | 438 | 0.0720 | 5,918 | 4,971 | 10,810 | 2.17 | | | | | |
| PP-11 | 1 | 0.100 | 3690 | 410 | 110 | 45 | 421 | 0.0660 | 5,644 | 3,457 | 6,785 | 1.96 | | | | | |
| PP-12 | 1 | 0.100 | 3690 | 410 | 110 | 45 | 481 | 0.0650 | 4,865 | 3,103 | 5,856 | 1.89 | | | | | |
| PP-13 | 1 | 0.100 | 3690 | 410 | 110 | 45 | 449 | 0.0670 | 5,372 | 3,274 | 6,774 | 2.07 | | | | | |
| PP-14 | 1 | 0.100 | 3690 | 410 | 110 | 45 | 471 | 0.0670 | 5,121 | 3,261 | 6,036 | 1.85 | 6.26 | 1 | 4 | 78 | 17 |
| PP-15 | 1 | 0.100 | 3690 | 410 | 115 | 45 | 513 | 0.0650 | 4,561 | 2,511 | 4,550 | 1.81 | 8.34 | 1 | 3 | 79 | 18 |
| PP-16 | 1 | 0.100 | 3690 | 410 | 115 | 45 | 463 | 0.0600 | 4,665 | 2,481 | 4,413 | 1.78 | | | | | |
| PP-17 | 1 | 0.100 | 3690 | 410 | 115 | 45 | 434 | 0.0620 | 5,143 | 2,716 | 4,944 | 1.82 | | | | | |
| PP-18 | 1 | 0.100 | 3690 | 410 | 115 | 45 | 468 | 0.0640 | 4,923 | 2,415 | 4,486 | 1.86 | | | | | |
| PP-19 | 2 | 0.025 | 3895 | 205 | 70 | 30 | 1801 | 0.0601 | 4,805 | 113,853 | 181,438 | 1.59 | | | | | |
| PP-20 | 2 | 0.025 | 3895 | 205 | 70 | 30 | 1801 | 0.0669 | 5,348 | 116,448 | 199,737 | 1.72 | 0.57 | 10 | 11 | 30 | 49 |
| PP-21 | 2 | 0.025 | 3895 | 205 | 70 | 30 | 1802 | 0.0582 | 4,651 | 121,345 | 204,691 | 1.69 | | | | | |
| PP-22 | 2 | 0.025 | 3895 | 205 | 100 | 30 | 1803 | 0.0115 | 918 | 21,917 | 36,496 | 1.67 | | | | | |
| PP-23 | 2 | 0.025 | 3895 | 205 | 100 | 30 | 1801 | 0.0150 | 1,199 | 22,258 | 35,996 | 1.62 | | | | | |
| PP-24 | 2 | 0.025 | 3895 | 205 | 100 | 30 | 1802 | 0.0100 | 799 | 21,364 | 33,977 | 1.59 | | | | | |
| PP-25 | 2 | 0.100 | 3690 | 410 | 100 | 45 | 2700 | 0.0420 | 560 | 20,561 | 33,930 | 1.65 | | | | | |
| PP-26 | 2 | 0.100 | 3690 | 410 | 100 | 45 | 2700 | 0.0450 | 600 | 20,080 | 35,446 | 1.77 | 1.71 | 6 | 6 | 49 | 39 |
| PP-27 | 2 | 0.100 | 3690 | 410 | 100 | 45 | 2701 | 0.0390 | 520 | 16,704 | 31,203 | 1.87 | | | | | |
| PP-28 | 2 | 0.100 | 3690 | 410 | 100 | 45 | 2700 | 0.0420 | 560 | 18,279 | 33,268 | 1.82 | | | | | |
| PP-29 | 2 | 0.100 | 3690 | 410 | 110 | 45 | 2701 | 0.0290 | 387 | 13,367 | 21,906 | 1.64 | | | | | |
| PP-30 | 2 | 0.100 | 3690 | 410 | 110 | 45 | 2701 | 0.0270 | 360 | 13,524 | 22,448 | 1.66 | | | | | |
| PP-31 | 2 | 0.100 | 3690 | 410 | 110 | 45 | 2701 | 0.0270 | 360 | 11,366 | 20,519 | 1.81 | | | | | |
| PP-32 | 2 | 0.100 | 3690 | 410 | 110 | 45 | 2701 | 0.0250 | 333 | 12,209 | 21,910 | 1.79 | | | | | |
| PP-33 | 2 | 0.100 | 3690 | 410 | 115 | 45 | 2701 | 0.0190 | 253 | 8,698 | 15,403 | 1.77 | | | | | |
| PP-34 | 2 | 0.100 | 3690 | 410 | 115 | 45 | 2701 | 0.0200 | 267 | 9,638 | 16,378 | 1.70 | | | | | |
| PP-35 | 2 | 0.100 | 3690 | 410 | 115 | 45 | 2700 | 0.0180 | 240 | 8,896 | 15,513 | 1.74 | | | | | |
| PP-36 | 2 | 0.100 | 3690 | 410 | 115 | 45 | 2701 | 0.0200 | 267 | 8,472 | 15,397 | 1.82 | | | | | |
| PP-37 | 3 | 0.025 | 3895 | 205 | 70 | 30 | 1467 | 0.0644 | 6,321 | 242,077 | 358,612 | 1.48* | 0.66 | 26 | 35 | 23 | 17 |

TABLE 4-continued

Polymerization examples producing polypropylene

| Ex # | Cat ID | Cat (umol) | Iso-hex-ane (uL) | Tolu-ene (uL) | T (C.) | Max Rxn Time (mm) | Quench Time (s) | Yield (g) | Activity (g P/mmol cat · hr) | Mn | Mw | PDI | total unsat/ 1000 C. | % vinyl-ene | % trisub | % vinyl | % vinyl-idene |
|---|---|---|---|---|---|---|---|---|---|---|---|---|---|---|---|---|---|
| PP-38 | 3 | 0.025 | 3895 | 205 | 70 | 30 | 1801 | 0.0539 | 4,309 | 260,364 | 387,546 | 1.49* | 0.50 | 34 | 14 | 24 | 28 |
| PP-39 | 3 | 0.025 | 3895 | 205 | 100 | 30 | 1368 | 0.0630 | 6,633 | 37,607 | 55,686 | 1.48* | 1.35 | 11 | 17 | 53 | 19 |
| PP-41 | 3 | 0.025 | 3895 | 205 | 100 | 30 | 1638 | 0.0533 | 4,685 | 31,533 | 46,250 | 1.47* | 1.09 | 8 | 6 | 69 | 17 |
| PP-42 | 3 | 0.100 | 3790 | 310 | 100 | 45 | 201 | 0.1032 | 18,511 | 26,915 | 42,424 | 1.58* | 1.26 | 3 | 0 | 77 | 20 |
| PP-43 | 3 | 0.100 | 3790 | 310 | 100 | 45 | 214 | 0.1179 | 19,834 | 30,866 | 47,579 | 1.54* | 1.21 | 4 | 4 | 72 | 20 |
| PP-44 | 3 | 0.100 | 3790 | 310 | 100 | 45 | 166 | 0.0817 | 17,697 | 32,446 | 49,989 | 1.54* | | | | | |
| PP-45 | 3 | 0.100 | 3790 | 310 | 100 | 45 | 187 | 0.0979 | 18,857 | 29,467 | 45,445 | 1.54* | | | | | |
| PP-46 | 3 | 0.100 | 3690 | 410 | 100 | 45 | 248 | 0.0990 | 14,371 | 24,332 | 47,626 | 1.96 | 1.31 | 6 | 5 | 71 | 18 |
| PP-47 | 3 | 0.100 | 3690 | 410 | 100 | 45 | 253 | 0.1000 | 14,229 | 20,851 | 46,079 | 2.21 | | | | | |
| PP-48 | 3 | 0.100 | 3690 | 410 | 100 | 45 | 224 | 0.0840 | 13,500 | 25,447 | 50,789 | 2.00 | | | | | |
| PP-49 | 3 | 0.100 | 3690 | 410 | 100 | 45 | 259 | 0.0950 | 13,205 | 23,058 | 45,702 | 1.98 | | | | | |
| PP-50 | 3 | 0.100 | 3690 | 410 | 110 | 45 | 241 | 0.0940 | 14,041 | 14,097 | 28,833 | 2.05 | 1.89 | 3 | 3 | 76 | 18 |
| PP-51 | 3 | 0.100 | 3690 | 410 | 110 | 45 | 221 | 0.0920 | 14,986 | 14,507 | 30,196 | 2.08 | | | | | |
| PP-52 | 3 | 0.100 | 3690 | 410 | 110 | 45 | 215 | 0.0900 | 15,070 | 14,277 | 31,031 | 2.17 | | | | | |
| PP-53 | 3 | 0.100 | 3690 | 410 | 110 | 45 | 218 | 0.0870 | 14,367 | 14,269 | 29,060 | 2.04 | | | | | |
| PP-54 | 3 | 0.100 | 3690 | 410 | 115 | 45 | 238 | 0.0920 | 13,916 | 12,109 | 22,335 | 1.84 | | | | | |
| PP-55 | 3 | 0.100 | 3690 | 410 | 115 | 45 | 238 | 0.0930 | 14,067 | 10,839 | 20,759 | 1.92 | 2.51 | 3 | 2 | 77 | 17 |
| PP-56 | 3 | 0.100 | 3690 | 410 | 115 | 45 | 226 | 0.0820 | 13,062 | 11,483 | 21,945 | 1.91 | | | | | |
| PP-57 | 3 | 0.100 | 3690 | 410 | 115 | 45 | 215 | 0.0660 | 11,051 | 12,072 | 23,149 | 1.92 | | | | | |
| PP-58 | 3 | 0.120 | 3748 | 352 | 110 | 45 | 181 | 0.1171 | 19,420 | 15,545 | 25,659 | 1.65* | 2.19 | 4 | 4 | 75 | 17 |
| PP-59 | 3 | 0.120 | 3748 | 352 | 110 | 45 | 156 | 0.1052 | 20,231 | 17,055 | 27,875 | 1.63* | | | | | |
| PP-60 | 3 | 0.120 | 3748 | 352 | 110 | 45 | 169 | 0.1127 | 20,006 | 16,981 | 27,603 | 1.63* | 2.08 | 4 | 1 | 76 | 18 |
| PP-61 | 3 | 0.120 | 3748 | 352 | 110 | 45 | 151 | 0.0965 | 19,122 | 17,866 | 28,532 | 1.60* | | | | | |
| PP-62 | 3 | 0.140 | 3706 | 394 | 115 | 45 | 144 | 0.1159 | 20,696 | 12,012 | 19,807 | 1.65* | 2.83 | 3 | 4 | 76 | 17 |
| PP-63 | 3 | 0.140 | 3706 | 394 | 115 | 45 | 149 | 0.1195 | 20,693 | 11,853 | 19,615 | 1.65* | 2.68 | 2 | 0 | 80 | 18 |
| PP-64 | 3 | 0.140 | 3706 | 394 | 115 | 45 | 140 | 0.1083 | 19,835 | 10,912 | 18,361 | 1.68* | | | | | |
| PP-65 | 3 | 0.140 | 3706 | 394 | 115 | 45 | 148 | 0.1092 | 18,986 | 11,285 | 18,466 | 1.64* | | | | | |
| PP-66 | 4 | 0.025 | 3895 | 205 | 70 | 30 | 1802 | 0.0412 | 3,293 | 148,334 | 256,830 | 1.73 | | | | | |
| PP-67 | 4 | 0.025 | 3895 | 205 | 70 | 30 | 1801 | 0.0448 | 3,582 | 146,069 | 244,922 | 1.68 | 0.46 | 13 | 9 | 43 | 35 |
| PP-68 | 4 | 0.025 | 3895 | 205 | 70 | 30 | 1803 | 0.0363 | 2,899 | 146,190 | 240,227 | 1.64 | | | | | |
| PP-69 | 4 | 0.025 | 3895 | 205 | 100 | 30 | 1801 | 0.0251 | 2,006 | 27,639 | 43,958 | 1.59 | | | | | |
| PP-70 | 4 | 0.025 | 3895 | 205 | 100 | 30 | 1801 | 0.0276 | 2,207 | 23,327 | 39,530 | 1.69 | | | | | |
| PP-71 | 4 | 0.025 | 3895 | 205 | 100 | 30 | 1801 | 0.0289 | 2,311 | 23,193 | 37,667 | 1.62 | 1.66 | 6 | 8 | 67 | 19 |
| PP-72 | 4 | 0.100 | 3690 | 410 | 100 | 45 | 385 | 0.0750 | 7,013 | 19,133 | 34,498 | 1.80 | | | | | |
| PP-73 | 4 | 0.100 | 3690 | 410 | 100 | 45 | 413 | 0.0840 | 7,322 | 20,238 | 35,033 | 1.73 | 1.43 | 4 | 3 | 78 | 15 |
| PP-74 | 4 | 0.100 | 3690 | 410 | 100 | 45 | 408 | 0.0680 | 6,000 | 21,140 | 39,289 | 1.86 | | | | | |
| PP-75 | 4 | 0.100 | 3690 | 410 | 100 | 45 | 419 | 0.0780 | 6,702 | 17,946 | 32,638 | 1.82 | | | | | |
| PP-76 | 4 | 0.100 | 3690 | 410 | 110 | 45 | 387 | 0.0790 | 7,349 | 12,512 | 22,125 | 1.77 | | | | | |
| PP-77 | 4 | 0.100 | 3690 | 410 | 110 | 45 | 395 | 0.0810 | 7,382 | 12,319 | 23,162 | 1.88 | 2.29 | 3 | 3 | 80 | 14 |
| PP-78 | 4 | 0.100 | 3690 | 410 | 110 | 45 | 362 | 0.0740 | 7,359 | 12,618 | 21,714 | 1.72 | | | | | |
| PP-80 | 4 | 0.100 | 3690 | 410 | 115 | 45 | 376 | 0.0660 | 6,319 | 9,499 | 16,288 | 1.71 | | | | | |
| PP-81 | 4 | 0.100 | 3690 | 410 | 115 | 45 | 389 | 0.0760 | 7,033 | 8,718 | 16,714 | 1.92 | 2.85 | 2 | 3 | 81 | 14 |
| PP-82 | 4 | 0.100 | 3690 | 410 | 115 | 45 | 371 | 0.0590 | 5,725 | 8,500 | 15,716 | 1.85 | | | | | |
| PP-83 | 4 | 0.100 | 3690 | 410 | 115 | 45 | 400 | 0.0640 | 5,760 | 8,495 | 16,286 | 1.92 | | | | | |
| CPP-1 | 5 | 0.100 | 3690 | 410 | 100 | 45 | 106 | 0.1710 | 58,075 | 81,754 | 166,050 | 2.03 | 0.50 | 12 | 4 | 36 | 48 |
| CPP-2 | 5 | 0.025 | 3895 | 205 | 100 | 30 | 562 | 0.0666 | 17,053 | 149,325 | 218,995 | 1.47* | 0.54 | 19 | 18 | 15 | 48 |
| CPP-3 | 5 | 0.080 | 3832 | 268 | 100 | 45 | 126 | 0.1748 | 62,379 | 94,271 | 151,197 | 1.60* | 0.61 | 10 | 10 | 33 | 47 |
| CPP-4 | 5 | 0.025 | 3895 | 205 | 100 | 30 | 559 | 0.0685 | 17,652 | 154,163 | 224,874 | 1.46* | 0.65 | 11 | 21 | 23 | 45 |
| CPP-5 | 5 | 0.080 | 3832 | 268 | 100 | 45 | 118 | 0.1600 | 61,017 | 104,515 | 162,175 | 1.55* | 0.72 | 8 | 17 | 28 | 47 |
| CPP-6 | 5 | 0.100 | 3790 | 310 | 110 | 45 | 89 | 0.1759 | 71,311 | 50,772 | 83,127 | 1.64* | 0.74 | 12 | 0 | 42 | 46 |
| CPP-7 | 5 | 0.100 | 3690 | 410 | 110 | 45 | 105 | 0.1860 | 63,771 | 45,107 | 98,604 | 2.19 | 0.78 | 11 | 9 | 40 | 40 |
| CPP-8 | 5 | 0.120 | 3748 | 352 | 115 | 45 | 102 | 0.1529 | 44,927 | 41,255 | 66,402 | 1.61* | 0.88 | 7 | 0 | 45 | 48 |
| CPP-9 | 5 | 0.025 | 3895 | 205 | 70 | 30 | 634 | 0.0974 | 22,136 | 855,536 | 1,231,099 | 1.44* | 0.88 | 6 | 28 | 32 | 34 |
| CPP-10 | 5 | 0.100 | 3690 | 410 | 115 | 45 | 103 | 0.1640 | 57,320 | 31,028 | 71,043 | 2.29 | 0.91 | 9 | 7 | 45 | 40 |
| CPP-11 | 5 | 0.100 | 3790 | 310 | 110 | 45 | 91 | 0.1769 | 70,214 | 48,806 | 80,007 | 1.64* | 0.92 | 11 | 9 | 39 | 41 |
| CPP-12 | 5 | 0.120 | 3748 | 352 | 115 | 45 | 88 | 0.1676 | 56,878 | 36,447 | 61,036 | 1.67* | 1.12 | 8 | 6 | 45 | 41 |
| CPP-13 | 5 | 0.025 | 3895 | 205 | 70 | 30 | 641 | 0.0844 | 18,948 | 942,680 | 1,313,975 | 1.39* | 2.02 | 10 | 43 | 27 | 19 |
| CPP-14 | 6 | 0.080 | 3752 | 348 | 100 | 45 | 107 | 0.1900 | 79,907 | 105,004 | 217,130 | 2.07 | 0.52 | 10 | 11 | 35 | 44 |
| CPP-15 | 6 | 0.080 | 3752 | 348 | 110 | 45 | 97 | 0.1580 | 73,299 | 63,872 | 135,550 | 2.12 | 0.59 | 8 | 14 | 36 | 42 |
| CPP-16 | 6 | 0.080 | 3752 | 348 | 115 | 45 | 103 | 0.1460 | 63,786 | 58,220 | 107,249 | 1.84 | 0.82 | 9 | 13 | 35 | 43 |
| CPP-17 | 7 | 0.080 | 3752 | 348 | 100 | 45 | 149 | 0.1430 | 43,188 | 136,290 | 259,066 | 1.90 | 0.44 | 9 | 7 | 41 | 43 |
| CPP-18 | 7 | 0.060 | 3814 | 286 | 110 | 45 | 174 | 0.1184 | 40,898 | 90,873 | 140,793 | 1.55* | 0.56 | 11 | 5 | 32 | 52 |
| CPP-19 | 7 | 0.080 | 3752 | 348 | 110 | 45 | 136 | 0.1210 | 40,037 | 82,945 | 150,717 | 1.82 | 0.61 | 8 | 12 | 36 | 44 |
| CPP-20 | 7 | 0.060 | 3814 | 286 | 110 | 45 | 175 | 0.1117 | 38,232 | 93,333 | 143,950 | 1.54* | 0.62 | 15 | 8 | 29 | 48 |
| CPP-21 | 7 | 0.040 | 3876 | 224 | 100 | 45 | 249 | 0.0992 | 35,798 | 157,179 | 250,895 | 1.60* | 0.63 | 9 | 13 | 24 | 54 |
| CPP-22 | 7 | 0.060 | 3814 | 286 | 115 | 45 | 182 | 0.0930 | 30,676 | 67,400 | 104,636 | 1.55* | 0.76 | 12 | 7 | 34 | 47 |
| CPP-23 | 7 | 0.080 | 3752 | 348 | 115 | 45 | 140 | 0.1160 | 37,286 | 59,972 | 111,756 | 1.86 | 0.80 | 8 | 16 | 40 | 36 |
| CPP-24 | 7 | 0.060 | 3814 | 286 | 115 | 45 | 232 | 0.0892 | 23,069 | 74,492 | 112,638 | 1.51* | 0.82 | 10 | 12 | 33 | 45 |
| CPP-25 | 7 | 0.040 | 3876 | 224 | 100 | 45 | 280 | 0.1016 | 32,657 | 174,695 | 264,209 | 1.51* | 0.83 | 5 | 19 | 24 | 52 |

*Rapid GPC system was used

TABLE 5

Polymerization examples producing polypropylene or ethylene-propylene copolymers

| Ex # | Cat ID | Cat (umol) | C2 (psig) | Isohexane (uL) | Toluene (uL) | Quench Value (psid) | Quench Time (s) | Yield (g) | Activity (g P/mmol cat · hr) | Mn | Mw | PDI | C2 (wt %) | total unsat/ 1000 C. | % vinylene | % trisub | % vinyl | % vinylidene |
|---|---|---|---|---|---|---|---|---|---|---|---|---|---|---|---|---|---|---|
| PP-84 | 1 | 0.040 | 0 | 3832 | 268 | 5 | 936 | 0.0470 | 4,519 | 42,141 | 69,263 | 1.64 | | | | | | |
| PP-85 | 1 | 0.040 | 0 | 3832 | 268 | 5 | 960 | 0.0520 | 4,875 | 46,588 | 78,382 | 1.68 | | | | | | |
| PP-86 | 1 | 0.040 | 0 | 3832 | 268 | 5 | 941 | 0.0520 | 4,973 | 43,176 | 76,050 | 1.76 | | | | | | |
| PP-87 | 1 | 0.040 | 0 | 3832 | 268 | 5 | 938 | 0.0520 | 4,989 | 43,579 | 74,727 | 1.71 | | 0.76 | 3 | 9 | 63 | 25 |
| EP-1 | 1 | 0.025 | 10 | 3875 | 205 | 5 | 531 | 0.0460 | 12,475 | 50,816 | 90,205 | 1.78 | 6.5 | | | | | |
| EP-2 | 1 | 0.025 | 10 | 3875 | 205 | 5 | 562 | 0.0540 | 13,836 | 59,091 | 96,009 | 1.62 | 7.1 | | | | | |
| EP-3 | 1 | 0.025 | 10 | 3875 | 205 | 5 | 486 | 0.0550 | 16,296 | 58,276 | 98,116 | 1.68 | 7.8 | 0.58 | 2 | 10 | 59 | 29 |
| EP-4 | 1 | 0.025 | 10 | 3875 | 205 | 5 | 449 | 0.0500 | 16,036 | 50,468 | 89,738 | 1.78 | 8.2 | | | | | |
| EP-5 | 1 | 0.025 | 20 | 3855 | 205 | 5 | 198 | 0.0500 | 36,364 | 68,056 | 118,980 | 1.75 | 15.6 | | | | | |
| EP-6 | 1 | 0.025 | 20 | 3855 | 205 | 5 | 226 | 0.0590 | 37,593 | 72,598 | 121,045 | 1.67 | 14.3 | 0.56 | 0 | 18 | 64 | 18 |
| EP-7 | 1 | 0.025 | 20 | 3855 | 205 | 5 | 227 | 0.0570 | 36,159 | 65,629 | 117,986 | 1.80 | 15.8 | | | | | |
| EP-8 | 1 | 0.025 | 20 | 3855 | 205 | 5 | 228 | 0.0580 | 36,632 | 69,711 | 118,662 | 1.84 | 15.5 | | | | | |
| EP-9 | 1 | 0.025 | 40 | 3835 | 205 | 5 | 99 | 0.0590 | 85,818 | 110,181 | 181,267 | 1.65 | 29.1 | | | | | |
| EP-10 | 1 | 0.025 | 40 | 3835 | 205 | 5 | 114 | 0.0690 | 87,158 | 99,136 | 178,943 | 1.81 | 24.4 | 0.42 | 2 | 0 | 67 | 31 |
| EP-11 | 1 | 0.025 | 40 | 3835 | 205 | 5 | 117 | 0.0670 | 82,462 | 101,315 | 179,684 | 1.77 | 27.0 | | | | | |
| EP-12 | 1 | 0.025 | 40 | 3835 | 205 | 5 | 143 | 0.0670 | 67,469 | 86,072 | 157,959 | 1.84 | 24.0 | | | | | |
| EP-13 | 1 | 0.025 | 60 | 3815 | 205 | 5 | 81 | 0.0830 | 147,556 | 106,100 | 205,666 | 1.94 | 32.3 | | | | | |
| EP-14 | 1 | 0.025 | 60 | 3815 | 205 | 5 | 89 | 0.0900 | 145,618 | 111,422 | 209,358 | 1.88 | 34.6 | | | | | |
| EP-15 | 1 | 0.025 | 60 | 3815 | 205 | 5 | 71 | 0.0800 | 162,254 | 133,950 | 224,785 | 1.68 | 37.1 | 0.42 | 0 | 5 | 67 | 29 |
| EP-16 | 1 | 0.025 | 60 | 3815 | 205 | 5 | 88 | 0.0860 | 142,364 | 116,186 | 217,379 | 1.87 | 34.2 | | | | | |
| EP-17 | 1 | 0.025 | 80 | 3795 | 205 | 5 | 52 | 0.0960 | 265,846 | 147,160 | 274,151 | 1.86 | 44.3 | | | | | |
| EP-18 | 1 | 0.025 | 80 | 3795 | 205 | 5 | 58 | 0.1040 | 258,207 | 149,560 | 267,604 | 1.79 | 45.9 | 0.25 | 0 | 16 | 64 | 20 |
| EP-19 | 1 | 0.025 | 80 | 3795 | 205 | 5 | 63 | 0.0990 | 226,286 | 132,841 | 252,290 | 1.90 | 43.6 | | | | | |
| EP-20 | 1 | 0.025 | 80 | 3795 | 205 | 5 | 62 | 0.0920 | 213,677 | 142,941 | 267,803 | 1.87 | 42.6 | | | | | |
| PP-88 | 2 | 0.040 | 0 | 3832 | 268 | 5 | 587 | 0.0490 | 7,513 | 87,995 | 157,653 | 1.79 | | 0.52 | 10 | 13 | 29 | 48 |
| PP-89 | 2 | 0.040 | 0 | 3832 | 268 | 5 | 673 | 0.0620 | 8,291 | 100,826 | 189,737 | 1.88 | | | | | | |
| PP-90 | 2 | 0.040 | 0 | 3832 | 268 | 5 | 693 | 0.0500 | 6,494 | 92,994 | 177,316 | 1.91 | | | | | | |
| PP-91 | 2 | 0.040 | 0 | 3832 | 268 | 5 | 761 | 0.0550 | 6,505 | 76,406 | 164,459 | 2.15 | | | | | | |
| EP-21 | 2 | 0.025 | 10 | 3875 | 205 | 5 | 293 | 0.0540 | 26,539 | 106,172 | 183,474 | 1.73 | 7.2 | | | | | |
| EP-22 | 2 | 0.025 | 10 | 3875 | 205 | 5 | 350 | 0.0650 | 26,743 | 109,365 | 208,164 | 1.90 | 7.3 | | | | | |
| EP-23 | 2 | 0.025 | 10 | 3875 | 205 | 5 | 351 | 0.0680 | 27,897 | 100,899 | 199,855 | 1.98 | 6.4 | 0.72 | 6 | 22 | 24 | 49 |
| EP-24 | 2 | 0.025 | 10 | 3875 | 205 | 5 | 373 | 0.0590 | 22,777 | 100,951 | 187,051 | 1.85 | 6.6 | | | | | |
| EP-25 | 2 | 0.025 | 20 | 3855 | 205 | 5 | 202 | 0.0680 | 48,475 | 104,810 | 188,540 | 1.80 | 10.2 | | | | | |
| EP-26 | 2 | 0.025 | 20 | 3855 | 205 | 5 | 195 | 0.0760 | 56,123 | 111,133 | 194,120 | 1.75 | 9.9 | 0.72 | 6 | 19 | 21 | 54 |
| EP-27 | 2 | 0.025 | 20 | 3855 | 205 | 5 | 196 | 0.0700 | 51,429 | 93,491 | 199,205 | 2.13 | 10.0 | | | | | |
| EP-28 | 2 | 0.025 | 20 | 3855 | 205 | 5 | 210 | 0.0640 | 43,886 | 105,517 | 197,472 | 1.87 | 11.6 | | | | | |
| EP-29 | 2 | 0.025 | 40 | 3835 | 205 | 5 | 135 | 0.0670 | 71,467 | 109,365 | 208,164 | 1.90 | 13.7 | | | | | |
| EP-30 | 2 | 0.025 | 40 | 3835 | 205 | 5 | 134 | 0.0780 | 83,821 | 122,384 | 210,807 | 1.72 | 14.9 | 0.87 | 6 | 18 | 18 | 57 |
| EP-31 | 2 | 0.025 | 40 | 3835 | 205 | 5 | 124 | 0.0760 | 88,258 | 105,028 | 206,212 | 1.96 | 17.5 | | | | | |
| EP-32 | 2 | 0.025 | 40 | 3835 | 205 | 5 | 165 | 0.0590 | 51,491 | 111,398 | 221,924 | 1.90 | 17.5 | | | | | |
| EP-33 | 2 | 0.025 | 60 | 3815 | 205 | 5 | 88 | 0.0790 | 129,273 | 120,766 | 221,480 | 1.83 | 20.5 | | | | | |
| EP-34 | 2 | 0.025 | 60 | 3815 | 205 | 5 | 95 | 0.0880 | 133,389 | 105,233 | 206,245 | 1.96 | 20.7 | | | | | |
| EP-35 | 2 | 0.025 | 60 | 3815 | 205 | 5 | 103 | 0.0880 | 123,029 | 112,463 | 211,076 | 1.88 | 20.5 | 1.03 | 3 | 24 | 20 | 52 |
| EP-36 | 2 | 0.025 | 60 | 3815 | 205 | 5 | 89 | 0.0870 | 140,764 | 103,893 | 210,177 | 2.02 | 20.1 | | | | | |
| EP-37 | 2 | 0.025 | 80 | 3795 | 205 | 5 | 62 | 0.0910 | 211,355 | 130,170 | 235,913 | 1.81 | 26.5 | | | | | |

TABLE 5-continued

Polymerization examples producing polypropylene or ethylene-propylene copolymers

| Ex # | Cat ID | Cat (μmol) | C2 (psig) | Isohexane (uL) | Toluene (uL) | Quench Value (psid) | Quench Time (s) | Yield (g) | Activity (g P/mmol cat · hr) | Mn | Mw | PDI | C2 (wt %) | total unsat/ 1000 C. | % vinylene | % trisub | % vinyl | % vinylidene |
|---|---|---|---|---|---|---|---|---|---|---|---|---|---|---|---|---|---|---|
| EP-38 | 2 | 0.025 | 80 | 3795 | 205 | 5 | 75 | 0.1040 | 199,680 | 120,086 | 233,064 | 1.94 | 24.2 | | | | | |
| EP-39 | 2 | 0.025 | 80 | 3795 | 205 | 5 | 78 | 0.1030 | 190,154 | 107,858 | 227,024 | 2.10 | 24.9 | 1.02 | 9 | 25 | 21 | 45 |
| EP-40 | 2 | 0.025 | 80 | 3795 | 205 | 5 | 74 | 0.1000 | 194,595 | 115,712 | 220,812 | 1.91 | 29.2 | | | | | |
| PP-92 | 3 | 0.040 | 0 | 3832 | 268 | 8 | 710 | 0.0341 | 4,324 | 176,043 | 258,609 | 1.47* | | | | | | |
| PP-93 | 3 | 0.040 | 0 | 3832 | 268 | 8 | 593 | 0.0150 | 2,275 | 119,952 | 175,476 | 1.46* | | | | | | |
| PP-94 | 3 | 0.040 | 0 | 3832 | 268 | 8 | 839 | 0.0716 | 7,677 | 196,848 | 294,867 | 1.50* | | 0.41 | 15 | 17 | 34 | 34 |
| PP-95 | 3 | 0.040 | 0 | 3832 | 268 | 8 | 458 | 0.0260 | 5,111 | 198,851 | 295,870 | 1.49* | | | | | | |
| EP-41 | 3 | 0.025 | 10 | 3875 | 205 | 8 | 628 | 0.0855 | 19,614 | 253,640 | 378,524 | 1.49* | 2.7^ | | | | | |
| EP-42 | 3 | 0.025 | 10 | 3875 | 205 | 8 | 265 | 0.1033 | 56,239 | 241,178 | 364,758 | 1.51* | 7.0 | 0.37 | 3 | 11 | 32 | 54 |
| EP-43 | 3 | 0.025 | 10 | 3875 | 205 | 8 | 411 | 0.0425 | 14,905 | 249,068 | 369,780 | 1.48* | 3.7^ | | | | | |
| EP-44 | 3 | 0.025 | 20 | 3855 | 205 | 8 | 830 | 0.0666 | 11,559 | 252,311 | 378,505 | 1.50* | 2.5^ | | | | | |
| EP-45 | 3 | 0.025 | 40 | 3835 | 205 | 8 | 660 | 0.0300 | 6,541 | 141,949 | 209,884 | 1.48* | 3.3^ | | | | | |
| EP-46 | 3 | 0.025 | 40 | 3835 | 205 | 8 | 324 | 0.1073 | 47,732 | 280,203 | 423,604 | 1.51* | 5.7 | 0.22 | 0 | 9 | 41 | 50 |
| EP-47 | 3 | 0.025 | 40 | 3835 | 205 | 8 | 229 | 0.0985 | 61,939 | 285,692 | 433,261 | 1.52* | 8.6 | | | | | |
| EP-48 | 3 | 0.025 | 60 | 3815 | 205 | 8 | 186 | 0.0866 | 67,153 | 247,802 | 379,087 | 1.53* | 13.3 | | | | | |
| EP-49 | 3 | 0.025 | 60 | 3815 | 205 | 8 | 140 | 0.1236 | 127,041 | 273,686 | 420,459 | 1.54* | 16.5 | 0.62 | 10 | 21 | 26 | 44 |
| EP-50 | 3 | 0.025 | 60 | 3815 | 205 | 8 | 112 | 0.1138 | 146,445 | 277,860 | 433,119 | 1.56* | 17.8 | | | | | |
| PP-96 | 4 | 0.040 | 0 | 3832 | 268 | 5 | 960 | 0.0530 | 4,969 | 118,661 | 221,792 | 1.87 | | 0.45 | 9 | 13 | 42 | 36 |
| PP-97 | 4 | 0.040 | 0 | 3832 | 268 | 5 | 942 | 0.0510 | 4,873 | 117,083 | 225,123 | 1.92 | | | | | | |
| PP-98 | 4 | 0.040 | 0 | 3832 | 268 | 5 | 942 | 0.0490 | 4,682 | 114,986 | 210,574 | 1.83 | | | | | | |
| PP-99 | 4 | 0.040 | 0 | 3832 | 268 | 5 | 985 | 0.0510 | 4,660 | 124,263 | 221,259 | 1.78 | | | | | | |
| EP-51 | 4 | 0.025 | 10 | 3875 | 205 | 5 | 603 | 0.0590 | 14,090 | 133,985 | 247,303 | 1.85 | 7.4 | 0.52 | 4 | 13 | 38 | 44 |
| EP-52 | 4 | 0.025 | 10 | 3875 | 205 | 5 | 534 | 0.0570 | 15,371 | 109,826 | 242,356 | 2.21 | 6.9 | | | | | |
| EP-53 | 4 | 0.025 | 10 | 3875 | 205 | 5 | 564 | 0.0570 | 14,553 | 141,698 | 250,688 | 1.77 | 7.1 | | | | | |
| EP-54 | 4 | 0.025 | 10 | 3875 | 205 | 5 | 520 | 0.0570 | 15,785 | 128,379 | 249,771 | 1.95 | 6.8 | | | | | |
| EP-55 | 4 | 0.025 | 20 | 3855 | 205 | 5 | 299 | 0.0610 | 29,378 | 146,950 | 261,854 | 1.78 | 9.8 | 0.63 | 3 | 19 | 35 | 43 |
| EP-56 | 4 | 0.025 | 20 | 3855 | 205 | 5 | 495 | 0.0540 | 15,709 | 154,351 | 277,773 | 1.80 | 8.5 | | | | | |
| EP-57 | 4 | 0.025 | 20 | 3855 | 205 | 5 | 331 | 0.0600 | 26,103 | 155,459 | 263,645 | 1.70 | 10.1 | | | | | |
| EP-58 | 4 | 0.025 | 20 | 3855 | 205 | 5 | 292 | 0.0490 | 24,164 | 133,630 | 275,629 | 2.06 | 11.5 | | | | | |
| EP-59 | 4 | 0.025 | 40 | 3835 | 205 | 5 | 226 | 0.0720 | 45,876 | 126,287 | 292,588 | 2.32 | 12.3 | | | | | |
| EP-60 | 4 | 0.025 | 40 | 3835 | 205 | 5 | 247 | 0.0690 | 40,227 | 177,839 | 335,565 | 1.89 | 12.3 | 0.69 | 3 | 20 | 35 | 42 |
| EP-61 | 4 | 0.025 | 40 | 3835 | 205 | 5 | 204 | 0.0750 | 52,941 | 174,283 | 311,839 | 1.79 | 12.8 | | | | | |
| EP-62 | 4 | 0.025 | 40 | 3835 | 205 | 5 | 272 | 0.0530 | 28,059 | 168,558 | 320,613 | 1.90 | 12.9 | | | | | |
| EP-63 | 4 | 0.025 | 60 | 3815 | 205 | 5 | 165 | 0.0790 | 68,945 | 165,525 | 322,769 | 1.95 | 17.3 | | | | | |
| EP-64 | 4 | 0.025 | 60 | 3815 | 205 | 5 | 217 | 0.0700 | 46,452 | 199,090 | 372,888 | 1.87 | 16.6 | | | | | |
| EP-65 | 4 | 0.025 | 60 | 3815 | 205 | 5 | 151 | 0.0800 | 76,291 | 151,289 | 336,358 | 2.22 | 17.8 | 0.41 | 5 | 5 | 44 | 46 |
| EP-66 | 4 | 0.025 | 60 | 3815 | 205 | 5 | 168 | 0.0770 | 66,000 | 153,138 | 329,066 | 2.15 | 17.2 | | | | | |
| EP-67 | 4 | 0.025 | 80 | 3795 | 205 | 5 | 119 | 0.0960 | 116,168 | 167,966 | 373,149 | 2.22 | 24.1 | | | | | |
| EP-68 | 4 | 0.025 | 80 | 3795 | 205 | 5 | 129 | 0.0940 | 104,930 | 196,545 | 375,761 | 1.91 | 21.4 | 0.61 | 3 | 48 | 28 | 21 |
| EP-69 | 4 | 0.025 | 80 | 3795 | 205 | 5 | 123 | 0.0960 | 112,390 | 180,501 | 381,542 | 2.11 | 25.9 | | | | | |
| EP-70 | 4 | 0.025 | 80 | 3795 | 205 | 5 | 145 | 0.0760 | 75,476 | 189,308 | 371,595 | 1.96 | 23.5 | | | | | |
| CPP-26 | 5 | 0.030 | 0 | 3874 | 226 | 8 | 524 | 0.1325 | 30,361 | 804,326 | 1,150,173 | 1.43* | | 0.48 | 13 | 25 | 25 | 38 |
| CEP-1 | 5 | 0.025 | 10 | 3875 | 205 | 8 | 268 | 0.3336 | 178,981 | 438,867 | 831,898 | 1.90* | 5.4 | 0.29 | 10 | 28 | 28 | 34 |
| CPP-2 | 5 | 0.025 | 60 | 3815 | 205 | 8 | 118 | 0.1662 | 203,510 | 552,950 | 866,613 | 1.57* | 14.7 | 0.22 | 0 | 27 | 14 | 59 |
| CPP-27 | 7 | 0.015 | 0 | 3843 | 257 | 20 | 2381 | 0.2267 | 22,849 | 792,130 | 1114,738 | 1.41* | | 0.23 | 4 | 30 | 30 | 35 |
| CEP-3 | 7 | 0.015 | 10 | 3823 | 257 | 20 | 669 | 0.3066 | 109,975 | 506,161 | 754,924 | 1.49* | 7.8 | 1.21 | 8 | 40 | 27 | 25 |
| CEP-4 | 7 | 0.015 | 10 | 3823 | 257 | 20 | 677 | 0.3260 | 115,637 | 522,720 | 859,328 | 1.64* | 7.3 | 0.42 | 2 | 40 | 31 | 26 |

TABLE 5-continued

Polymerization examples producing polypropylene or ethylene-propylene copolymers

| Ex # | Cat ID | Cat (μmol) | C2 (psig) | Isohexane (uL) | Toluene (uL) | Quench Value (psid) | Quench Time (s) | Yield (g) | Activity (g P/mmol cat · hr) | Mn | Mw | PDI | C2 (wt %) | total unsat/ 1000 C. | % vinylene | % trisub | % vinyl | % vinylidene |
|---|---|---|---|---|---|---|---|---|---|---|---|---|---|---|---|---|---|---|
| CEP-5 | 7 | 0.015 | 20 | 3803 | 257 | 20 | 607 | 0.3286 | 129,946 | 461,687 | 689,923 | 1.49* | 8.6 | 0.95 | 13 | 34 | 26 | 27 |
| CEP-6 | 7 | 0.015 | 20 | 3803 | 257 | 20 | 634 | 0.2939 | 111,256 | 496,852 | 806,139 | 1.62* | 6.7 | 0.46 | 13 | 46 | 22 | 20 |
| CEP-7 | 7 | 0.015 | 40 | 3783 | 257 | 20 | 322 | 0.2779 | 207,002 | 410,436 | 635,467 | 1.55* | 17.9 | 0.39 | 18 | 38 | 10 | 33 |
| CEP-8 | 7 | 0.015 | 40 | 3783 | 257 | 20 | 480 | 0.3406 | 170,371 | 431,237 | 657,602 | 1.52* | 14.2 | 0.33 | 9 | 33 | 24 | 33 |
| CEP-9 | 7 | 0.015 | 60 | 3763 | 257 | 20 | 363 | 0.3605 | 238,413 | 342,645 | 569,183 | 1.66* | 16.7 | 0.82 | 7 | 46 | 27 | 20 |
| CEP-10 | 7 | 0.015 | 60 | 3763 | 257 | 20 | 382 | 0.3807 | 239,371 | 152,282 | 257,905 | 1.69* | 22.6 | 0.47 | 11 | 34 | 23 | 32 |
| CEP-11 | 7 | 0.015 | 80 | 3743 | 257 | 20 | 281 | 0.3723 | 317,640 | 296,492 | 534,277 | 1.80* | 27.4 | 0.37 | 0 | 41 | 22 | 38 |
| CEP-12 | 7 | 0.015 | 80 | 3743 | 257 | 20 | 276 | 0.3638 | 316,922 | 306,842 | 518,383 | 1.69* | 24.5 | 0.52 | 15 | 48 | 17 | 19 |
| CPP-28 | 8 | 0.04 | 0 | 3832 | 268 | 5 | 2700 | 0.027 | 900 | 117,510 | 193,958 | 1.65 | 0.0 | 0.39 | 3 | 8 | 15 | 74 |
| CPP-29 | 8 | 0.04 | 0 | 3832 | 268 | 5 | 2703 | 0.027 | 899 | 129,832 | 208,244 | 1.60 | 0.0 | 0.39 | 3 | 8 | 15 | 74 |
| CEP-13 | 8 | 0.025 | 10 | 3875 | 205 | 5 | 233 | 0.043 | 26,575 | 125,881 | 216,508 | 1.72 | 29.9 | | | | | |
| CEP-14 | 8 | 0.025 | 10 | 3875 | 205 | 5 | 297 | 0.047 | 22,788 | 125,210 | 219,363 | 1.75 | 25.5 | 0.53 | 9 | 23 | 15 | 53 |
| CEP-15 | 8 | 0.025 | 20 | 3855 | 205 | 5 | 147 | 0.052 | 50,939 | 137,408 | 233,455 | 1.70 | 37.4 | 0.19 | 0 | 0 | 16 | 84 |
| CEP-16 | 8 | 0.025 | 20 | 3855 | 205 | 5 | 131 | 0.045 | 49,466 | 125,693 | 229,397 | 1.83 | 31.8 | | | | | |
| CEP-17 | 8 | 0.025 | 40 | 3835 | 205 | 5 | 66 | 0.066 | 144,000 | 140,920 | 255,436 | 1.81 | 47.4 | 0.16 | 0 | 13 | 25 | 63 |
| CEP-18 | 8 | 0.025 | 40 | 3835 | 205 | 5 | 63 | 0.059 | 134,857 | 156,782 | 265,582 | 1.69 | 42.1 | | | | | |
| CEP-19 | 8 | 0.025 | 60 | 3815 | 205 | 5 | 56 | 0.096 | 246,857 | 149,485 | 269,583 | 1.80 | 53.3 | 0.13 | 0 | 0 | 23 | 77 |
| CEP-20 | 8 | 0.025 | 60 | 3815 | 205 | 5 | 53 | 0.086 | 233,660 | 148,752 | 274,922 | 1.85 | 50.9 | | | | | |
| CEP-21 | 8 | 0.025 | 80 | 3795 | 205 | 5 | 44 | 0.121 | 396,000 | 167,638 | 295,848 | 1.76 | 54.0^ | 0.17 | 0 | 35 | 29 | 35 |
| CEP-22 | 8 | 0.025 | 80 | 3795 | 205 | 5 | 46 | 0.104 | 325,565 | 165,717 | 288,536 | 1.74 | 52.7 | | | | | |

*Rapid GPC system was used.
^Outside FTIR calibration range

FIG. 1 is a graph of vinyl unsaturation (%) in polymers (polypropylene or ethylene-propylene copolymer) produced at a reactor temperature of 70° C. for inventive catalysts, Cat IDs 1-4, versus comparative catalysts, Cat IDS 5, 7, and 8. FIG. 1 shows that the inventive catalysts generally produce polymers with higher amounts of vinyl unsaturation versus the comparative catalysts. The higher vinyl unsaturation for the hafnium based Cat ID 3 [diphenylmethylene(4,5-dimethylfluoren-9-yl)(cyclopentadien-1-yl)hafnium dimethyl] versus comparative zirconium based Cat ID 8 [diphenylmethylene(4,5-dimethylfluoren-9-yl)(cyclopentadien-1-yl) zirconium dimethyl] is notable. Vinyl unsaturation could be further enhanced by increasing the polymerization temperature or by use of a particular activator, such as a larger discrete activator.

Figure 2:
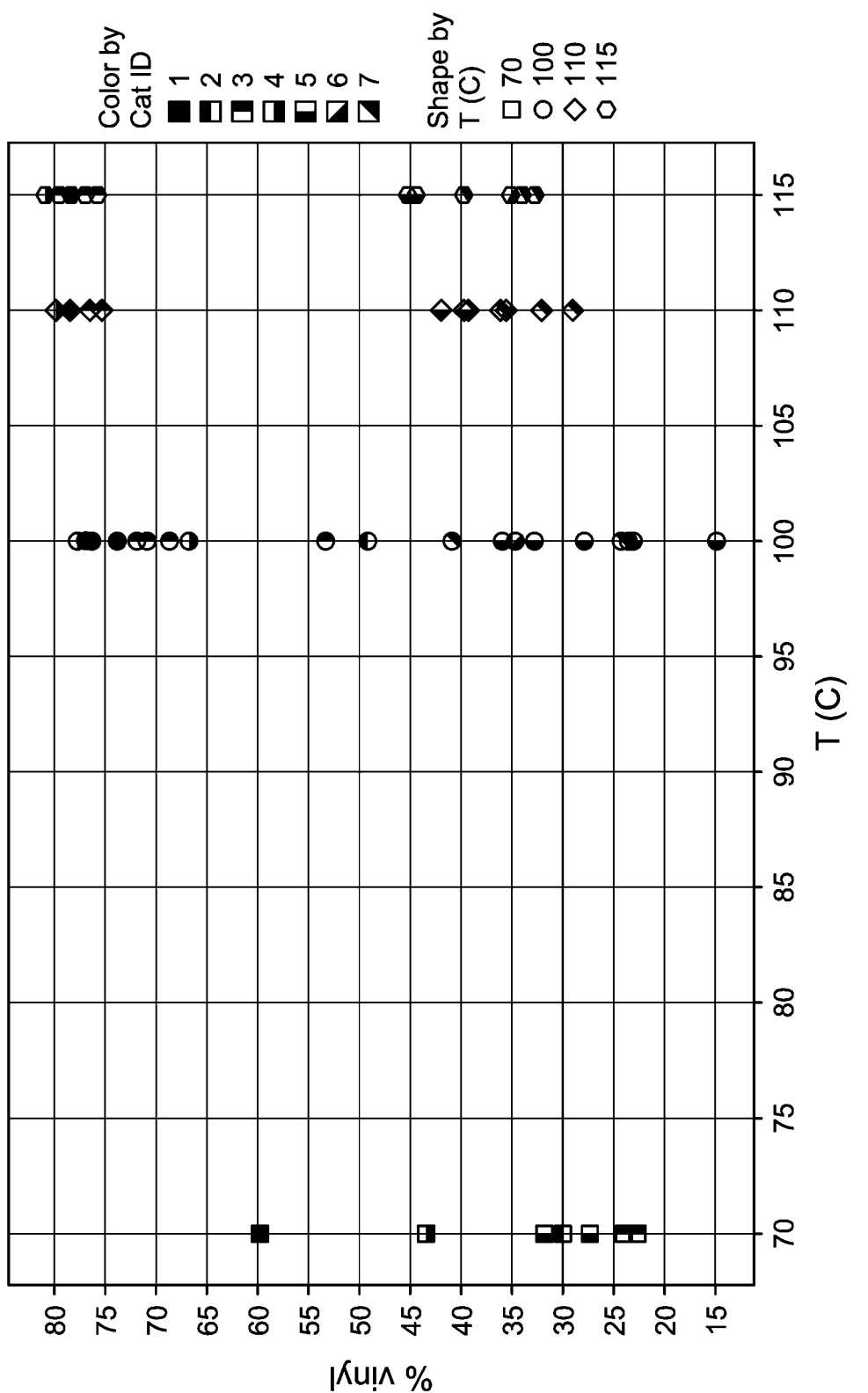
FIG. 2 is a graph of vinyl unsaturation versus reactor temperature at several reactor temperatures for polypropylene polymers produced by inventive and comparative catalysts.

FIG. 2 is a graph of vinyl unsaturation (%) versus reactor temperature in polypropylene produced at various reactor temperatures, including 70° C., 100° C., 110° C., and 115° C. The inventive catalysts, Cat IDs 1-4, clearly show an increase in vinyl unsaturation as the reactor temperature is increased. The increase is substantially less for comparative catalysts, Cat IDs 5, 6, and 7.

Figure 3:
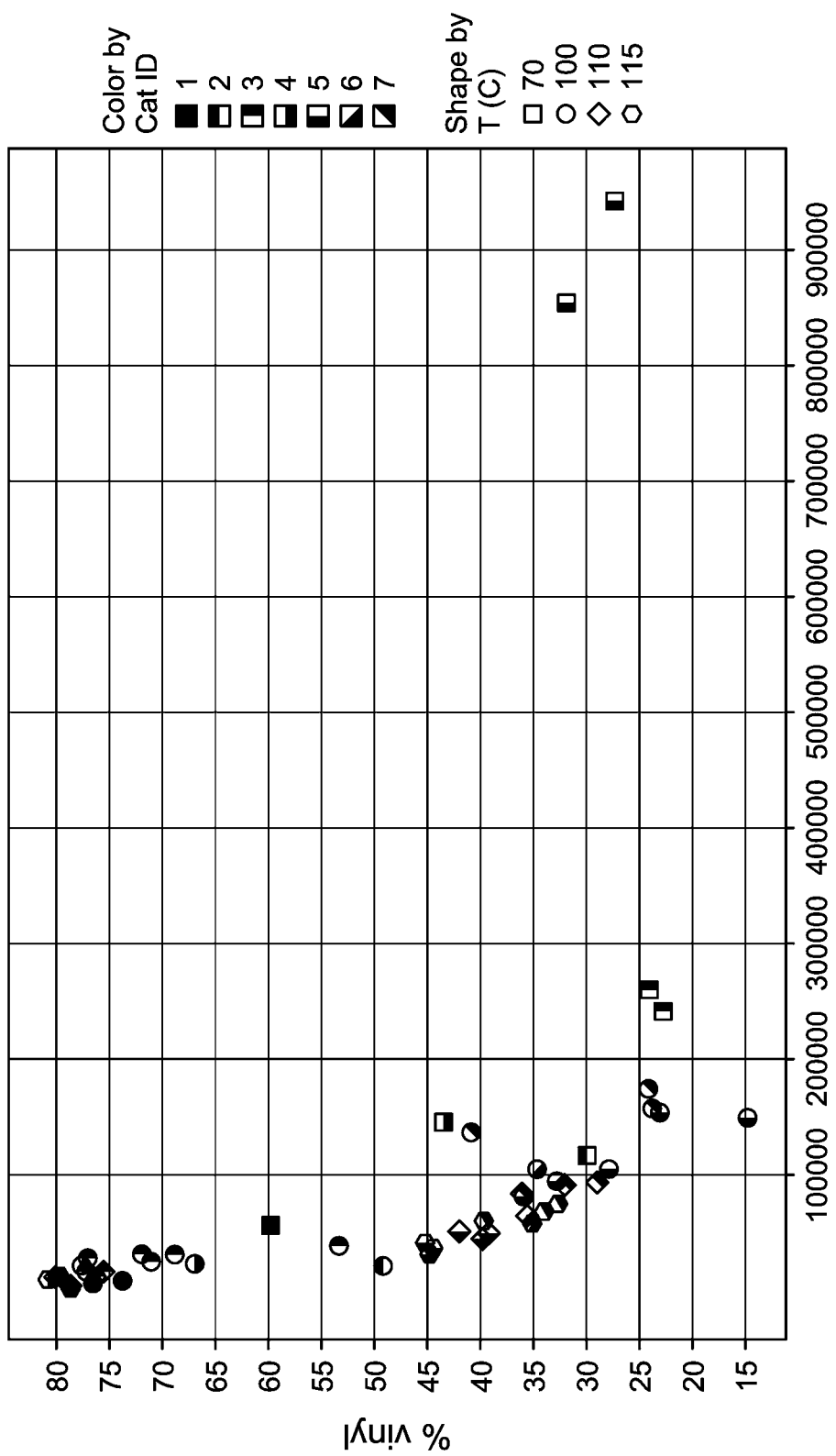
FIG. 3 is a graph of vinyl unsaturation versus polymer Mn for polypropylene polymers produced at various reactor temperatures.

FIG. 3 is a graph of vinyl unsaturation (%) versus polymer Mn for polypropylene polymers at various reactor temperatures, including 70° C., 100° C., 110° C., and 115° C. The inventive catalysts, Cat IDs 1-4, show a higher amount of vinyl unsaturations versus the comparative catalysts, Cat IDs 5, 6, and 7, at each reaction temperature.

Figure 4:
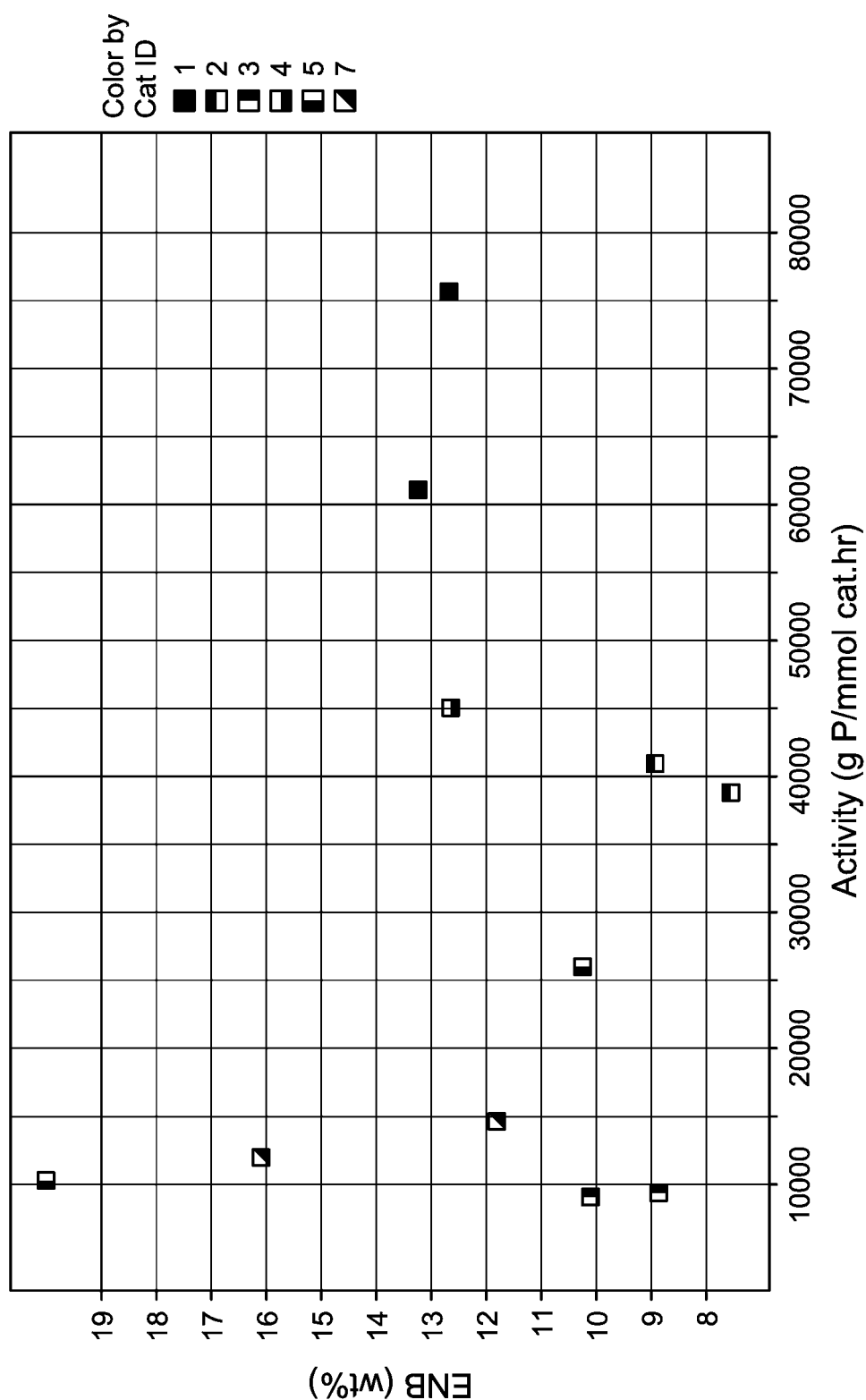
FIG. 4 is a graph of comonomer incorporation versus catalyst activity for ethylene-ENB copolymers produced by inventive and comparative catalysts.
Figure 5:
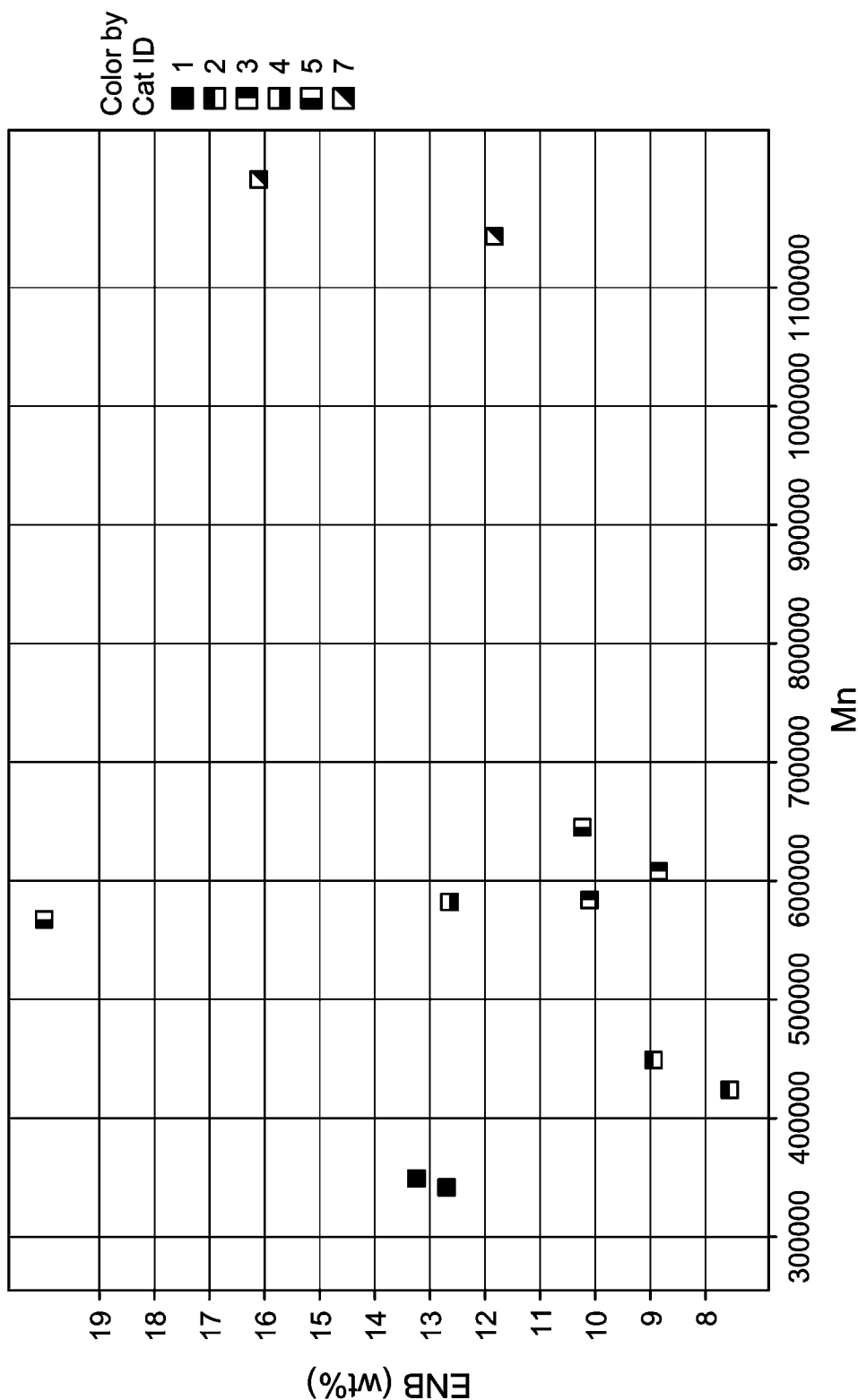
FIG. 5 is a graph of comonomer incorporation versus polymer Mn for the same ethylene-ENB copolymers shown in FIG. 4.

FIG. 4 is a graph of ENB incorporation (%) versus catalyst activity for E-ENB copolymers. FIG. 4 shows that Cat ID 1 incorporates ENB well, and also has very good catalyst activity. FIG. 5 is a graph of ENB incorporation (%) versus polymer Mn for the same polymers shown in FIG. 4. FIG. 5 shows that Cat ID 1 has a slightly lower, but still acceptable Mn versus the other catalysts.

All documents described herein are incorporated by reference herein, including any priority documents and/or testing procedures to the extent they are not inconsistent with this text. As is apparent from the foregoing general description and the specific embodiments, while forms of the invention have been illustrated and described, various modifications can be made without departing from the spirit and scope of the invention. Accordingly, it is not intended that the invention be limited thereby. Likewise, the term "comprising" is considered synonymous with the term "including." Likewise, whenever a composition, an element or a group of elements is preceded with the transitional phrase "comprising", it is understood that we also contemplate the same composition or group of elements with transitional phrases "consisting essentially of," "consisting of," "selected from the group consisting of," or "is" preceding the recitation of the composition, element, or elements and vice versa.

What is claimed is:

1. A syndiotactic propylene polymer having: 1) at least 50% allyl chain ends and/or 3-alkyl chain ends relative to the total number of unsaturated chain ends; 2) an Mw of 10,000 g/mol or more; 3) no detectable melting temperature by DSC; and 4) an Mw/Mn of 1.4 to 10, where the syndiotactic propylene polymer is a homopolymer and is prepared by a process comprising contacting propylene with a catalyst system, the catalyst system comprising an activator and at least one catalyst compound represented by formula (I):

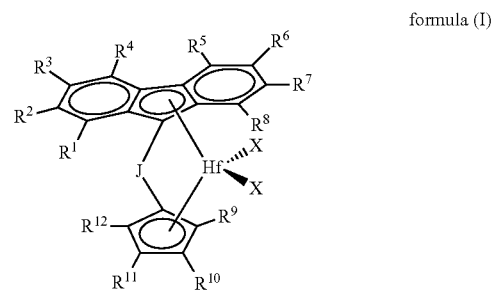

formula (I)

wherein each $R^1$, $R^2$, $R^3$, $R^6$, $R^7$, $R^8$, $R^9$, $R^{10}$, $R^{11}$, and $R^{12}$ is independently hydrogen or a $C_1$ to $C_{10}$ alkyl, and wherein any of $R^1$ and $R^2$, $R^2$ and $R^3$, $R^6$ and $R^7$, and $R^7$ and $R^8$ are optionally bonded together to form a ring structure;

each $R^4$ and $R^5$ is independently a $C_1$ to $C_{10}$ alkyl;

J is $SiR^{13}R^{14}$, $GeR^{13}R^{14}$ or $(CR^{15}R^{16})_x$, where x is 1 or 2; $R^{13}$ and $R^{14}$ are each independently selected from the group consisting of substituted or unsubstituted hydrocarbyl, halocarbyl, and silylcarbyl; $R^{15}$ and $R^{16}$ are each independently selected from the group consisting of hydrogen, substituted or unsubstituted hydrocarbyl, halocarbyl and silylcarbyl; and $R^{13}$ and $R^{14}$, or $R^{15}$ and $R^{16}$, when $R^{15}$ and $R^{16}$ are not hydrogen, are optionally bonded together to form a ring structure; and each X is independently a univalent anionic ligand, or two Xs are joined and bound to the metal atom to form a metallocycle ring, or two Xs are joined to form a chelating ligand, a diene ligand, or an alkylidene ligand.

2. The syndiotactic propylene polymer of claim 1, wherein the catalyst compound is represented by formula (II):

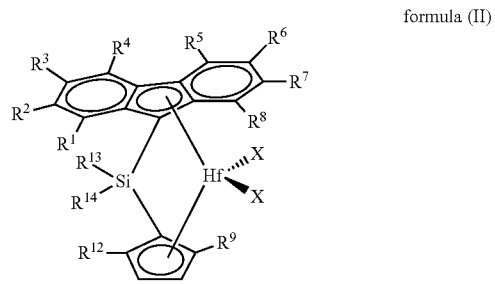

formula (II)

wherein each $R^1$, $R^2$, $R^3$, $R^6$, $R^7$, $R^8$, $R^9$, and $R^{12}$ is independently hydrogen or a $C_1$ to $C_{10}$ alkyl, and wherein any of $R^1$ and $R^2$, $R^2$ and $R^3$, $R^6$ and $R^7$, and $R^7$ and $R^8$ are optionally bonded together to form a ring structure;

each $R^4$ and $R^5$ is independently a $C_1$ to $C_{10}$ alkyl;

each $R^{13}$ and $R^{14}$ is independently selected from the group consisting of substituted or unsubstituted hydrocarbyl, halocarbyl, and silylcarbyl; and each X is independently a univalent anionic ligand, or two Xs are joined and bound to the metal atom to form a metallocycle ring, or two Xs are joined to form a chelating ligand, a diene ligand, or an alkylidene ligand.

3. The syndiotactic propylene polymer of claim 1, wherein the catalyst compound is represented by formula (III):

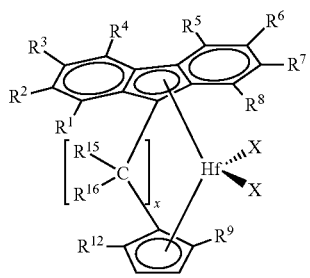

formula (III)

wherein each $R^1$, $R^2$, $R^3$, $R^6$, $R^7$, $R^8$, $R^9$, and $R^{12}$ is independently hydrogen or a $C_1$ to $C_{10}$ alkyl, and wherein any of $R^1$ and $R^2$, $R^2$ and $R^3$, $R^6$ and $R^7$, and $R^7$ and $R^8$ are optionally bonded together to form a ring structure;

each $R^4$ and $R^5$ is independently a $C_1$ to $C_{10}$ alkyl;

x is 1 or 2;

each $R^{15}$ and $R^{16}$ is independently selected from the group consisting of hydrogen, substituted or unsubstituted hydrocarbyl, halocarbyl and silylcarbyl; and $R^{15}$ and $R^{16}$, when $R^{15}$ and $R^{16}$ are not hydrogen, are optionally bonded together to form a ring structure; and each X is independently a univalent anionic ligand, or two Xs are joined and bound to the metal atom to form a metallocycle ring, or two Xs are joined to form a chelating ligand, a diene ligand, or an alkylidene ligand.

4. The syndiotactic propylene polymer of claim 1, wherein each $R^4$ and $R^5$ is independently selected from the group consisting of methyl, ethyl, propyl, butyl, and isomers thereof.

5. The syndiotactic propylene polymer of claim 1, wherein each $R^4$ and $R^5$ is independently selected from the group consisting of n-propyl, isopropyl, methyl, and ethyl.

6. The syndiotactic propylene polymer of claim 1, wherein each $R^1$, $R^2$, $R^3$, $R^6$, $R^7$, and $R^8$ is independently hydrogen or a $C_1$-$C_5$ alkyl.

7. The syndiotactic propylene polymer of claim 1, wherein J is Si or C and each $R^1$, $R^2$, $R^3$, $R^6$, $R^7$, $R^8$, $R^9$, and $R^{12}$ is independently hydrogen or a $C_1$-$C_5$ alkyl.

8. The syndiotactic propylene polymer of claim 1, wherein each $R^9$, $R^{10}$, $R^{11}$, and $R^{12}$ is independently hydrogen or a $C_1$-$C_5$ alkyl.

9. The syndiotactic propylene polymer of claim 1, wherein each $R^9$ and $R^{12}$ is independently hydrogen or a $C_1$-$C_5$ alkyl and $R^{10}$ and $R^{11}$ are hydrogen.

10. The syndiotactic propylene polymer of claim 1, wherein J is $SiR^{13}R^{14}$, and each $R^{13}$ and $R^{14}$ is independently selected from the group consisting of substituted or unsubstituted hydrocarbyl, halocarbyl, and silylcarbyl, and $R^{13}$ and $R^{14}$ are optionally bonded together to form a ring structure.

11. The syndiotactic propylene polymer of claim 1, wherein J is Si and $R^{13}$ and $R^{14}$ are joined together to form a 4, 5, or 6-membered ring structure.

12. The syndiotactic propylene polymer of claim 1, wherein J is Si or C and each $R^{13}$ and $R^{14}$ is independently selected from the group consisting of methyl, ethyl, propyl, butyl, pentyl, hexyl, heptyl, octyl, nonyl, decyl, phenyl, tolyl, benzyl, and isomers thereof.

13. The syndiotactic propylene polymer of claim 1, wherein J is selected from the group consisting of dimethylsilylene, diethylsilylene, methylethylsilylene, methylphenylsilylene, diethylsilylene, methylphenylsilylene, diphenylsilylene, and dipropylsilylene.

14. The syndiotactic propylene polymer of claim 1, wherein J is selected from the group consisting of cyclotrimethylenesilylene, cyclotetramethylenesilylene, and cyclopentamethylenesilylene.

15. The syndiotactic propylene polymer of claim 1, wherein J is $(CR^{15}R^{16})_x$, where x is 1 or 2, each $R^{15}$ and $R^{16}$ is independently selected from the group consisting of hydrogen, substituted or unsubstituted hydrocarbyl, halocarbyl, and silylcarbyl; and $R^{15}$ and $R^{16}$, when $R^{15}$ and $R^{16}$ are not hydrogen, and are optionally bonded together to form a ring structure.

16. The syndiotactic propylene polymer of claim 15, wherein x is 1 and each $R^{15}$ and $R^{16}$ is independently selected from the group consisting of hydrogen, methyl, ethyl, propyl, butyl, pentyl, hexyl, heptyl, octyl, nonyl, decyl, phenyl, tolyl, benzyl, and isomers thereof.

17. The syndiotactic propylene polymer of claim 15, wherein x is 1 and $R^{15}$ and $R^{16}$ are joined together to form a 4, 5, or 6-membered ring structure.

18. The syndiotactic propylene polymer of claim 1, wherein J is selected from the group consisting of dimethyl methylene, diethylmethylene, methylethylmethylene, methylphenylmethylene, diphenylmethylene, and dipropylmethylene.

19. The syndiotactic propylene polymer of claim 1, wherein J is ethylene or methylene.

20. The syndiotactic propylene polymer of claim 1, wherein each X is independently methyl, benzyl, or halo, where halo includes fluoride, chloride, bromide, and iodide.

21. A syndiotactic propylene homopolymer having: 1) at least 50% allyl chain ends and/or 3-alkyl chain ends relative to the total number of unsaturated chain ends; 2) an Mw of 10,000 g/mol or more; 3) no detectable melting temperature by DSC; and 4) an Mw/Mn of 1.4 to 10, where the syndiotactic propylene homopolymer is prepared by a process comprising contacting propylene with a catalyst system, the catalyst system comprising an activator and at least one compound represented by formula (IV):

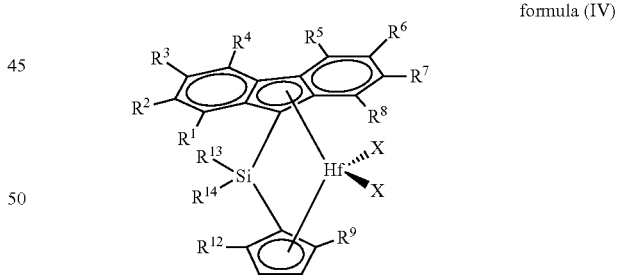

formula (IV)

wherein each $R^1$, $R^2$, $R^3$, $R^6$, $R^7$, $R^8$, $R^9$, and $R^{12}$ is independently hydrogen or a $C_1$ to $C_5$ alkyl, and wherein any of $R^1$ and $R^2$, $R^2$ and $R^3$, $R^6$ and $R^7$, and $R^7$ and $R^8$ are optionally bonded together to form a ring structure;

each $R^4$ and $R^5$ is independently selected from the group consisting of methyl, ethyl, propyl, butyl, and isomers thereof;

each $R^{13}$ and $R^{14}$ is independently selected from the group consisting of substituted or unsubstituted hydrocarbyl, halocarbyl, and silylcarbyl; and each X is independently a univalent anionic ligand, or two Xs are joined and bound to the metal atom to form a metallocycle ring, or two Xs are joined to form a chelating ligand, a diene ligand, or an alkylidene ligand.

22. A syndiotactic propylene homopolymer having: 1) at least 50% allyl chain ends and/or 3-alkyl chain ends relative to the total number of unsaturated chain ends; 2) an Mw of 10,000 g/mol or more; 3) no detectable melting temperature by DSC: and 4) an Mw/Mn of 1.4 to 10.

23. A syndiotactic propylene homopolymer having: 1) at least 50% allyl chain ends and/or 3-alkyl chain ends relative to the total number of unsaturated chain ends; 2) an Mw of 4000 g/mol or more; 3) no detectable melting temperature by DSC: and 4) an Mw/Mn of 1.4 to 10; and a branching index ($g'_{vis}$) of 0.90 or less, as determined by GPC.

24. The syndiotactic propylene homopolymer of claim 22, where the homopolymer has 1) at least 60% allyl chain ends and/or 3-alkyl chain ends relative to the total number of unsaturated chain ends.

25. The syndiotactic propylene homopolymer of claim 22, where the homopolymer has at least 70% allyl chain ends and/or 3-alkyl chain ends relative to the total number of unsaturated chain ends.

26. The syndiotactic propylene homopolymer of claim 22, where the homopolymer has an Mw of 25,000 to 5,000,000 g/mol.

27. The syndiotactic propylene homopolymer of claim 22, where the homopolymer has an Mw of 50,000 to 5,000,000 g/mol.

28. A syndiotactic propylene polymer having: 1) at least 50% allyl chain ends and/or 3-alkyl chain ends relative to the total number of unsaturated chain ends; 2) an Mw of 4,000 g/mol or more; 3) no detectable melting temperature by DSC; and 4) a branching index ($g'_{vis}$) of 0.90 or less, as determined by GPC, where the syndiotactic propylene polymer is a homopolymer and is prepared by a process comprising contacting propylene with a catalyst system, the catalyst system comprising an activator and at least one catalyst compound represented by formula (I):

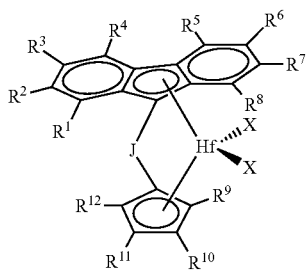

formula (I)

wherein each $R^1$, $R^2$, $R^3$, $R^6$, $R^7$, $R^8$, $R^9$, $R^{10}$, $R^{11}$, and $R^{12}$ is independently hydrogen or a $C_1$ to $C_{10}$ alkyl, and wherein any of $R^1$ and $R^2$, $R^2$ and $R^3$, $R^6$ and $R^7$, and $R^7$ and $R^8$ are optionally bonded together to form a ring structure;

each $R^4$ and $R^5$ is independently a $C_1$ to $C_{10}$ alkyl;

J is $SiR^{13}R^{14}$, $GeR^{13}R^{14}$ or $(CR^{15}R^{16})_x$, where x is 1 or 2; $R^{13}$ and $R^{14}$ are each independently selected from the group consisting of substituted or unsubstituted hydrocarbyl, halocarbyl, and silylcarbyl; $R^{15}$ and $R^{16}$ are each independently selected from the group consisting of hydrogen, substituted or unsubstituted hydrocarbyl, halocarbyl and silylcarbyl; and $R^{13}$ and $R^{14}$, or $R^{15}$ and $R^{16}$, when $R^{15}$ and $R^{16}$ are not hydrogen, are optionally bonded together to form a ring structure; and each X is independently a univalent anionic ligand, or two Xs are joined and bound to the metal atom to form a metallocycle ring, or two Xs are joined to form a chelating ligand, a diene ligand, or an alkylidene ligand.

29. The syndiotactic propylene polymer of claim 1, where the polymer has 1) at least 60% allyl chain ends and/or 3-alkyl chain ends relative to the total number of unsaturated chain ends.

30. The syndiotactic propylene polymer of claim 1, where the polymer has at least 70% allyl chain ends and/or 3-alkyl chain ends relative to the total number of unsaturated chain ends.

31. The syndiotactic propylene polymer of claim 1, where the homopolymer has a Mw of 25,000 to 5,000,000 g/mol.

32. The syndiotactic propylene polymer of claim 1, where the homopolymer has a Mw of 50,000 to 5,000,000 g/mol.

33. A syndiotactic copolymer of ethylene and propylene, wherein the copolymer comprises from 0.1 to 50 wt % ethylene and having: 1) at least 50% allyl chain ends and/or 3-alkyl chain ends relative to the total number of unsaturated chain ends; 2) an Mw of 4,000 g/mol or more; and 3) a $g'_{vis}$ of 0.90 or less.

34. A syndiotactic propylene polymer having: 1) a branching index ($g'_{vis}$) of 0.90 or less, as determined by GPC; 2) at least 50%, allyl chain ends and/or 3-alkyl chain ends; 3) an Mw from 3,000 to 500,000 g/mol.

35. The syndiotactic propylene polymer of claim 1, wherein the syndiotactic propylene polymer has an Mw/Mn of 1.4 to 5.

36. The syndiotactic propylene polymer of claim 22, wherein the syndiotactic propylene polymer has an Mw/Mn of 1.4 to 5.

* * * * *